United States Patent
Santos et al.

(10) Patent No.: US 11,708,376 B2
(45) Date of Patent: Jul. 25, 2023

(54) SUBSTITUTED IMIDAZO[4,5-B]PYRIDINES, IMIDAZO[4,5-B]PYRAZINES, AND OXAZOLO[4,5-B]PYRAZINES AS MITOCHONDRIAL UNCOUPLERS

(71) Applicant: VIRGINIA TECH INTELLECTUAL PROPERTIES, INC., Blacksburg, VA (US)

(72) Inventors: Webster L. Santos, Blacksburg, VA (US); Yumin Dai, Blacksburg, VA (US); Jose A. Santiago-Rivera, Blacksburg, VA (US); Jacob H. Murray, Blacksburg, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 22 days.

(21) Appl. No.: 17/049,232

(22) PCT Filed: Apr. 22, 2019

(86) PCT No.: PCT/US2019/028555
§ 371 (c)(1),
(2) Date: Oct. 20, 2020

(87) PCT Pub. No.: WO2019/204816
PCT Pub. Date: Oct. 24, 2019

(65) Prior Publication Data
US 2021/0238181 A1     Aug. 5, 2021

Related U.S. Application Data

(60) Provisional application No. 62/660,880, filed on Apr. 20, 2018.

(51) Int. Cl.
| | |
|---|---|
| A61K 31/437 | (2006.01) |
| A61K 31/4985 | (2006.01) |
| C07D 471/04 | (2006.01) |
| C07D 487/04 | (2006.01) |
| C07D 498/04 | (2006.01) |
| A61P 3/04 | (2006.01) |
| C07F 5/02 | (2006.01) |

(Continued)

(52) U.S. Cl.
CPC ............ *C07D 498/04* (2013.01); *A61K 45/06* (2013.01); *A61P 3/04* (2018.01); *C07D 241/20* (2013.01); *C07D 471/04* (2013.01); *C07D 487/04* (2013.01); *C07F 5/025* (2013.01)

(58) Field of Classification Search
CPC .............. A61K 31/437; A61K 31/4985; C07D 471/04; C07D 487/04
USPC .................... 514/249, 303; 544/350; 546/118
See application file for complete search history.

(56) References Cited

U.S. PATENT DOCUMENTS

| 4,394,320 A | 7/1983 | Pereyre et al. |
|---|---|---|
| 4,472,840 A | 9/1984 | Jefferies |
| 4,559,157 A | 12/1985 | Smith et al. |

(Continued)

FOREIGN PATENT DOCUMENTS

| EP | 1529531 A1 | 5/2005 |
|---|---|---|
| EP | 2017277 A1 | 1/2009 |

(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
"2-[3-(Trifluoromethyl)anilino]-3-pyridinol"; PubChem; PubChem CID: 902055; Create Date: Jul. 9, 2005; pp. 1-6.
"3-(Octylamino)-1H-pyrazin-2-one"; PubChem; PubChem CID: 115765354; Create Date: Jan. 29, 2016; pp. 1-5.
Alasadi et al.; "Effect of mitochondrial uncouplers niclosamide ethanolamine (NEN) and oxyclozanide on hepatic metastasis of colon cancer"; Cell Death and Disease; vol. 9 (215); 2018; pp. 1-14.

(Continued)

*Primary Examiner* — Douglas M Willis
(74) *Attorney, Agent, or Firm* — Cantor Colburn LLP

(57) ABSTRACT

The disclosure provides compounds of Formula (I-A) and (I-B) and the pharmaceutically acceptable salts thereof. The variables, R, $R^2$, $R^3$, $X^1$, $X^2$, $X^3$, $Y^1$, Y, and Z are defined herein. Certain compounds of Formula (I-A) and (I-B) act as selective mitochondrial protonophore uncouplers that do not affect plasma membrane potential. These compounds are useful for treating or decreasing the risk of conditions responsive to mitochondrial uncoupling, such as cancer, obesity, type II diabetes, fatty liver disease, insulin resistance, Parkinson's disease, ischemia reperfusion injury, heart failure, non-alcoholic fatty liver disease (NALFD), and non-alcoholic steatohepatitis (NASH), Because mitochondrial uncouplers decrease the production of reactive oxygen species (ROS), which are known to contribute to age-related cell damage, the compounds are useful for increasing lifespan. Compounds and salts of Formulae (I-A) and (I-B) are also useful for regulating glucose homeostasis or insulin action in a patient.

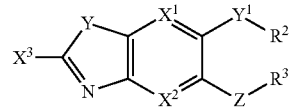

I-A

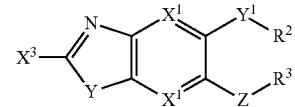

I-B

26 Claims, 1 Drawing Sheet

(51) Int. Cl.
    A61K 45/06     (2006.01)
    C07D 241/20     (2006.01)

(56) References Cited

U.S. PATENT DOCUMENTS

| | | | |
|---|---|---|---|
| 4,608,392 | A | 8/1986 | Jacquet et al. |
| 4,820,508 | A | 4/1989 | Wortzman |
| 4,938,949 | A | 7/1990 | Borch et al. |
| 4,992,478 | A | 2/1991 | Geria |
| 5,366,509 | A | 11/1994 | Ota et al. |
| 5,606,019 | A | 2/1997 | Cappello |
| 5,645,591 | A | 7/1997 | Kuberasampath et al. |
| 5,683,459 | A | 11/1997 | Brekke |
| 9,492,448 | B2 | 11/2016 | Hoehn et al. |
| 2002/0120137 | A1 | 8/2002 | Houze et al. |
| 2009/0131445 | A1 | 5/2009 | Baures et al. |
| 2009/0163545 | A1 | 6/2009 | Goldfarb |
| 2015/0322081 | A1 | 11/2015 | Hoehn et al. |
| 2017/0240563 | A1 | 8/2017 | Hoehn et al. |
| 2017/0319516 | A1 | 11/2017 | Jin et al. |

FOREIGN PATENT DOCUMENTS

| | | | | |
|---|---|---|---|---|
| KR | | 101428622 B1 | 8/2014 | |
| WO | | 2005044270 A1 | 5/2005 | |
| WO | | 2006044402 A1 | 4/2006 | |
| WO | | 2006124874 A2 | 11/2006 | |
| WO | | 2007017096 A1 | 2/2007 | |
| WO | | 2013192388 A1 | 12/2013 | |
| WO | | 2014068171 A1 | 5/2014 | |
| WO | | 2017151063 A1 | 9/2017 | |
| WO | | 2018217757 A1 | 11/2018 | |
| WO | WO-2019204816 A1 | * | 10/2019 | ............. A61K 31/44 |

OTHER PUBLICATIONS

Andrianov et al.; "Chemistry of Furazano[3,4-b]Pyrazines. 2. Nucleophilic Substitution of the Azido Group in Furazano[3,4-b]Pyrazines"; Chemistry of Heterocyclic Compounds; vol. 33, No. 8; 1997; pp. 977-982.
Bi et al.; "Novel syntheses of 3-anilino-pyrazin-2(1H)-ones and 3-anilino-quinoxalin-2-(1H)-ones via microwave-mediated Smiles rearrangement"; Tetrahedron Letters; vol. 49 (11); 2008; pp. 1832-1835; Compounds: 1018672-04-2, 1018672-06-4.
Bisballe et al.; "Functionalization of Oxazolo[4,5-b]pyrazines by Deprotometallation"; European Journal of Organic Chemistry; vol. 2018, Issue 29; 2018; pp. 3904-3913.
Fernandez et al.; "Solid-Phase Versus Solution Synthesis of Asymmetrically Disubstituted Furazano[3,4-b] Pyrazines"; Tetrahedron Letters; vol. 43, No. 27; Jul. 1, 2002; pp. 4741-4745.
International Search Report; International Application No. PCT/US2019/028554; International Filing Date: Apr. 22, 2019; dated Aug. 9, 2019; 7 Pages.
International Search Report; International Application No. PCT/US2019/028555; International Filing Date: Apr. 22, 2019; dated Aug. 2, 2019; 6 Pages.
International Search Report; International Application No. PCT/US2019/028560; International Filing Date: Apr. 22, 2019; dated Aug. 16, 2019; 5 Pages.
Jastroch et al.; "From explosives to physiological combustion: Next generation chemical uncouplers"; Molecular Metabolism; vol. 3; 2014; pp. 86-87.
Karady et al.; "1,2,5-Thiadiazole 1-oxides. V. Ring transformations to pyrazine, 1,2,4-thiadiazole and pyrrole"; Heterocycles; vol. 24, No. 5; 1986; pp. 1193-1196; Compounds: 107836-17-9.

Kenwood et al.; "Structure-Activity Relationships of Furazano[3,4-b]Pyrazines as Mitochondrial Uncouplers"; Bioorganic & Medicinal Chemistry Letters; vol. 25, No. 21; Nov. 1, 2015; pp. 4858-4861.
Kumar et al.; "Mitochondrial uncoupling reveals a novel therapeutic opportunity for p53-defective cancers"; Nature Communications; vol. 9, Article No. 3931; 2018; pp. 1-13.
Paulekuhn; "Trends in Active Pharmaceutical Ingredient Salt Selection based on Analysis of the Orange Book Database"; Journal of Medicinal Chemistry; vol. 50; 2007; pp. 6665-6672.
Saparpakorn et al.; "Use of 3D Qsar to investigate the mode of binding of pyrazinones to HIV-1 RT"; Monatshefte fuer Chemie; vol. 140 (6); 2009; pp. 587-594; Compounds: 467468-96-8.
Satoh et al.; "Identification of Niclosamide as a Novel Anticancer Agent for Adrenocortical Carcinoma"; American Association for Cancer Research; 2017; pp. 1-25.
Serasinghe et al; "Dual Suppression of inner and outer mitchondrial membrane functions augments apoptotic response to oncogenic MAPK inhibitgion"; Cell Death Dis; vol. 9 (2); 2018; pp. 1-22.
Serasinghe et al; "Mitochondrial Division is Requisite to RAS-Induced Transformation and Targeted by Oncogenic MAPK Pathway Inhibitors"; Molecular Cell; vol. 57; 2015; pp. 521-536.
Shikata et al.; "Mitochondrial uncoupler exerts a synthetic lethal effect against β-catenin mutant tumor cells"; Cancer Science; vol. 108; No. 4; 2017; pp. 772-784.
Stahl et al.; "Handbook of Pharmaceutical Salts: Properties, Selection and Use"; Weinheim/Zurich: Wiley-VCH/VHCA; 2002.
Starchenkov et al.; "Chemistry of Furazano[3,4-b]Pyrazines 3. Method for the Synthesis of 5,6-Disubstituted Furazano[3,4-b]Pyrazines"; Chemistry of Heterocyclic Compounds; vol. 33, No. 10; 1997; pp. 1219-1233.
Tarigopula et al.; "Design and structure activity relationship (SAR) of a novel pyrazinone series with non-nucleoside HIV-1 reverse transcriptase inhibitory activity"; International Journal of Plant, Animal and Environmental Sciences; vol. 25, No. 2; 2015; pp. 140-151; Compounds: 196641-00-3, 196642-94-8, 196643-89-4, 1971909-67-7, 1971909-68-8.
Wang et al.; "Uncoupling Hepatic Oxidative Phosphorylation Reduces Tumor Growth in Two Murine Models of Colon Cancer"; Cell Rep; vol. 24, No. 1; 2018; pp. 1-18.
Written Opinion; International Application No. PCT/US2019/028554; International Filing Date: Apr. 22, 2019; dated Aug. 9, 2019; 11 Pages.
Written Opinion; International Application No. PCT/US2019/028555; International Filing Date: Apr. 22, 2019; dated Aug. 2, 2019; 9 Pages.
Written Opinion; International Application No. PCT/US2019/028560; International Filing Date: Apr. 22, 2019; dated Aug. 16, 2019; 5 Pages.
Chemical Abstracts CAS Reg. No. 328268-59-3.
Alexopoulos et al.; "Mitochondrial Uncoupler BAM15 Reverses Diet-Induced Obesity and insulin Resistance in Mice"; Nature Communications; (2020); pp. 1-13.
Childress et al.; "[1,2,5]Oxadiazolo[3,4-b]pyrazine-5,6-diamine Derivatives as Mitochondrial Uncouplers for the Potential Treatment of Nonalcoholic Steatohepatitis"; Journal of Medicinal Chemistry; vol. 63; (2020); pp. 2511-2526.
Murray et al.; "Anilinopyrazines as Potential Mitochondrial Uncouplers"; Bioorganic & Medicinal Chemistry Letters; vol. 30, Issue 127057; (2020); 4 Pages.
Salamoun et al.; "6-Amino[1,2,5]oxadiazolo[3,4-b]pyrazin-5-ol Derivatives as Efficacious Mitochondrial Uncouplers in STAM Mouse Model of Nonalcoholic Steatohepatitis"; Journal of Medicinal Chemistry; vol. 63; (2020); pp. 6203-6224.
Aulinger-Fuchs et al., "Preparation of Oxadiazolopyrezines as Kinase Inhibitors," STN Accession No. 2005:402557, (2005).
STN Registry, Columbus, Ohio, US Registry Online, (2018), 23 pages.

* cited by examiner

SUBSTITUTED IMIDAZO[4,5-B]PYRIDINES, IMIDAZO[4,5-B]PYRAZINES, AND OXAZOLO[4,5- B]PYRAZINES AS MITOCHONDRIAL UNCOUPLERS

CROSS-REFERENCE TO RELATED APPLICATIONS

This application is a National Stage Application of PCT/US2019/028555, filed Apr. 22, 2019, which claims priority of U.S. Provisional Appl. No. 62/660,880, filed Apr. 20, 2018, and all the benefits accruing therefrom under 35 U.S.C. § 119, the content of which is hereby incorporated by reference in its entirety.

BACKGROUND

Cellular respiration is a physiological process with a fundamental goal of producing energy in the form of ATP. During cellular respiration, chemical energy derived from nutrients is converted into ATP. Specifically, the oxidation of nutrients in the mitochondrial matrix generates high-energy electron carriers nicotinamide adenine dinucleotide (NADH) and flavin adenine dinucleotide ($FADH_2$) that are oxidized by the mitochondrial electron transport chain (ETC) located in the mitochondrial inner-membrane (MIM). Electron flow through the ETC is an exergonic process that drives a series of proton pumps to efflux protons from the matrix into the inter-membrane space (IMS) against their concentration gradient. The resulting proton concentration ($\Delta pH$) and electrical ($\Delta \Psi$) gradient is known as the proton-motive force (pmf). Protons that re-enter the mitochondrial matrix via ATP synthase drive endergonic production of ATP. Thus, mitochondrial ATP production involves the coupling of electron transport to phosphorylation reactions via a proton gradient across the MIM.

Mitochondrial uncoupling describes processes that uncouple nutrient oxidation from ATP production. Mitochondrial uncoupling is a normal physiological process that occurs as either basal or inducible proton leak from the intermembrane space. Basal proton leak accounts for ~20-25% of the basal metabolic rate of mammals. The reason for such metabolic inefficiency is not entirely understood; however, membrane lipid composition and abundance of the adenine nucleotide translocase (ANT) are factors that contribute to basal rates of proton leak. Induced proton leak is driven by reactive species and fatty acids that activate uncoupling proteins (UCPs). UCPs are located in the MIM and facilitate the transfer protons into the matrix independent of ATP synthase.

There are five known UCPs in mammals, UCP1-5, that have distinct tissue localization. The best-characterized UCPs are UCP1 and UCP2. UCP1 is expressed in brown and beige adipose tissue and has a role in non-shivering thermogenesis. UCP1 is unlikely to operate as a simple proton channel, but instead transfers protons via a mechanism that requires long-chain fatty acids. In contrast, UCP2 has a broad tissue distribution and no role in thermogenesis. UCP2 uncouples mitochondria to prevent hyperpolarization and decrease mitochondrial superoxide production.

Small molecule mitochondrial uncouplers either act directly as protonophores by transporting protons into the matrix independently of protein complexes or, alternatively, mediate uncoupling via proteins such as ANT. Protonophoric uncouplers are lipophilic enough to enable passage through the MIM and weakly acidic to enable partial and reversible pH-dependent ionization. Mitochondrial uncoupling has two major phenotypes of therapeutic relevance including increased nutrient oxidation to compensate for lack of efficiency in ATP production and decreasing superoxide production from the ETC. The ETC is a primary source of reactive oxygen species (ROS) in most tissues. ETC-derived superoxide formation occurs via a non-enzymatic process when single electrons on co-enzymes or prosthetic groups in redox centers interact with molecular oxygen. Single electrons in the ETC only transiently exist in redox centers and the dwell time for single electrons in an unstable state increases the likelihood of superoxide production. Mitochondrial uncouplers decrease mitochondrial superoxide production by stimulating faster electron transfer that decreases the dwell time for single electrons in the ETC.

The therapeutic potential of mitochondrial uncouplers is related to their dual roles in increasing nutrient oxidation and decreasing ROS production from the ETC. On the one hand, increased nutrient oxidation promotes leanness and is a therapeutic strategy to treat obesity and related metabolic diseases. On the other hand, mitochondrial ROS are linked to numerous pathologies including ischemia-reperfusion injury, inflammation, insulin resistance, neurodegeneration, and many other pathologies. Importantly, mitochondrial uncouplers prevent ROS production, which is advantageous compared to antioxidants that scavenge ROS that has already been produced. As such, decreasing mitochondrial ROS production has significant therapeutic potential with advantages over antioxidant scavengers.

Mitochondria regulate cellular metabolism and play an important role in the pathogenesis of some of the most prevalent human diseases including obesity, cancer, diabetes, neurodegeneration, and heart disease. Many of these diseases can be improved by the use of pharmacological agents like mitochondrial uncouplers that lessen mitochondrial oxidative damage and increase energy expenditure. Genetic and pharmacologic uncoupling have beneficial effects on disorders that are linked to mitochondrial oxidative stress, such as ischemic-reperfusion injury, Parkinson's disease, insulin resistance, aging, and heart failure, and disorders that stand to benefit from increased energy expenditure such as obesity.

Mitochondrial uncouplers are known and have been shown to be effective for treating obesity. For example, 2,4-dinitrophenol (DNP) is a well-known small molecule mitochondrial protonophore that results in weight loss in humans. Patients consuming ~300 mg/d steadily shed an average of 1.3 pounds per week over the course of several months without changes in food intake. Similarly, mice treated with DNP demonstrate improved serological glucose, triglyceride, and insulin levels, as well as decreased oxidative damage, reduced body weight, and increased longevity. However, DNP has off-target effects on other cellular membranes resulting in a narrow therapeutic index. DNP was subsequently withdrawn from the North American market by the US Food and Drug Administration in 1938. Currently, there are no uncoupler drugs that are safe enough for use in humans.

The development of a selective mitochondrial protonophore uncoupler that does not affect the plasma membrane potential would broaden the safety margin of mitochondrial uncouplers and provide renewed hope that mitochondrial uncoupling can be targeted for the treatment of obesity, type II diabetes, and other diseases, disorders, and conditions related to mitochondrial function. There is a long felt need in the art for compositions and methods useful for preventing and treating obesity, diabetes, regulating glucose homeostasis, reducing adiposity, protecting from ischemic-reperfusion injury, and regulating insulin action using mitochondrial uncouplers as well as for compounds useful as mitochondrial uncouplers. The present disclosure satisfies these needs.

SUMMARY

This disclosure provides compounds of Formula I-A and I-B

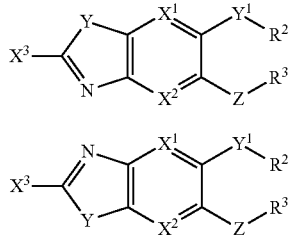

Formula I-A

Formula I-B or a pharmaceutically acceptable salts thereof. Within Formula I-A and I-B the variables, e.g. $X^1$, $X^2$, $X^3$, Y, $Y^1$, $R^2$, and $R^3$ carry the following definitions.

$X^1$ and $X^2$ are C or N, with at least one of $X^1$ and $X^2$ being N.

$X^3$ is H, $C_1$-$C_4$alkyl, $C_1$-$C_2$haloalkyl, phenyl, or halogen substituted phenyl.

Y is O or NR.

$Y^1$ is O or $NR^1$.

Z is O or S.

R is H or methyl.

$R^1$ is hydrogen or $C_1$-$C_8$alkyl, $C_2$-$C_8$alkenyl, or $C_2$-$C_8$alkynyl.

$R^2$ is $C_1$-$C_8$alkyl, $C_2$-$C_8$alkenyl, or $C_2$-$C_8$alkynyl; or $R^2$ is —$C_0$-$C_4$alkyl($C_3$-$C_7$cycloalkyl), —$C_0$-$C_4$alkyl (bridged $C_7$-$C_{12}$cycloalkyl), —$C_0$-$C_4$alkyl(aryl), —$C_0$-$C_4$alkyl(mono- or bi-cyclic heteroaryl), or —$C_0$-$C_4$alkyl(4- to 7-membered heterocycloalkyl), each of which is optionally substituted with one or more substituents independently chosen from $R^{11}$ and 0 or 1 substituents $R^{12}$; or $R^1$ and $R^2$ are joined to form a 3-7 membered cyclic ring in which one carbon is optionally replaced by N, S, or O.

$R^3$ is H or $C_1$-$C_8$alkyl, $C_2$-$C_8$alkenyl, or $C_2$-$C_8$alkynyl, or $R^3$ is —$C_0$-$C_4$alkyl($C_3$-$C_7$cycloalkyl), —$C_0$-$C_4$alkyl (aryl), or —$C_0$-$C_4$alkyl(heteroaryl), each of which is optionally substituted with one or more independently chosen $R^{11}$ substituents.

Wherein in each $C_0$-$C_4$alkyl, $C_1$-$C_8$alkyl, $C_2$-$C_8$alkenyl, or $C_2$-$C_8$alkynyl in the definitions of $R^1$, $R^2$, and $R^3$ one or more carbon atoms is optionally replaced by O, $NR^{10}$, —C(O)—, —C(O)O—, —OC(O), —S(O)n-, —S(O)n$NR^{10}$, —$NR^{10}$S(O)n-, —$NR^{10}$C(O)$NR^{10}$, —C(O)$NR^{10}$—, or —$NR^{10}$C(O)— where n is 0, 1, or 2, and in which the $C_0$-$C_4$alkyl, $C_1$-$C_8$ alkyl, $C_2$-$C_8$alkenyl, or $C_2$-$C_8$alkynyl is optionally substituted with one or more substituents $R^{13}$.

$R^{10}$ is independently chosen at each occurrence from hydrogen, $C_1$-$C_6$alkyl, and —$C_0$-$C_2$alkyl($C_3$-$C_7$cycloalkyl).

$R^{11}$ is independently selected at each occurrence from halogen, hydroxyl, amino, nitro, cyano, —CHO, —COOH, oxo, halosulfanyl, and $C_1$-$C_8$alkyl, $C_2$-$C_8$alkenyl, and $C_2$-$C_8$alkynyl, wherein in each $C_1$-$C_8$alkyl, $C_2$-$C_8$alkenyl, and $C_2$-$C_8$alkynyl, in the definition of $R^{11}$ one or more carbon atoms is optionally replaced by O, $NR^{10}$, —C(O)—, —C(O)O—, —OC(O), —S(O)n-, —C(O)$NR^{10}$—, or —$NR^{10}$C(O)— where n is 0, 1, or 2, and in which each $C_0$-$C_4$alkyl, $C_1$-$C_8$alkyl, $C_2$-$C_8$alkenyl, or $C_2$-$C_8$alkynyl is optionally substituted with one or more substituents $R^{13}$.

$R^{12}$ is selected from —$C_0$-$C_4$alkyl($C_3$-$C_7$cycloalkyl), —O—$C_0$-$C_4$alkyl($C_3$-$C_7$cycloalkyl), —$C_0$-$C_4$alkyl(aryl), —O—$C_0$-$C_4$alkyl(aryl), —$C_0$-$C_4$alkyl(5- to 6-membered heteroaryl), —O—$C_0$-$C_4$alkyl(5- to 6-membered heteroaryl), —$C_0$-$C_4$alkyl(5- to 6-membered heterocycloalkyl), and —O—$C_0$-$C_4$alkyl(5- to 6-membered heterocycloalkyl), each of which is optionally substituted with one or more substituents independently chosen from halogen, hydroxyl, amino, nitro, cyano, —CHO, —COOH, oxo, $C_1$-$C_2$haloalkyl, $C_1$-$C_2$haloalkoxy, $C_1$-$C_6$alkyl, $C_1$-$C_6$alkoxy, $C_1$-$C_6$alkylester, —$C_0$-$C_4$alkyl(mono- or di-$C_1$-$C_6$alkylamino), $C_2$-$C_6$alkanoyl, $C_2$-$C_6$alkenyl, and $C_2$-$C_6$alkynyl.

$R^{13}$ is independently chosen at each occurrence from halogen, hydroxyl, amino, nitro, cyano, —CHO, —COOH, oxo, $C_3$-$C_7$cycloalkyl, and phenyl.

The disclosure includes a pharmaceutical composition, comprising a compound or salt of Formula I-A or I-B, together with a pharmaceutically acceptable excipient.

The disclosure includes a method of treating or preventing a condition responsive to mitochondrial uncoupling, comprising administering a therapeutically effective amount of a compound or salt of Formula I-A or I-B to a patient in need of such treatment. Conditions responsive to mitochondrial uncoupling include obesity, type II diabetes, fatty liver disease, insulin resistance, Parkinson's disease, ischemia reperfusion injury, heart failure, non-alcoholic fatty liver disease (NALFD), and non-alcoholic steatohepatitis (NASH).

The disclosure includes a method of regulating glucose homeostasis or insulin action in a patient comprising administering a therapeutically effective amount of a compound or salt of Formula I-A or I-B to a patient in need thereof.

The disclosure also includes a method of treating hyperlipidemia, glycemia, glucose tolerance, insulin sensitivity, adiposity, insulin resistance, obesity, or diabetes in a patient comprising administering a therapeutically effective amount of a compound of any one of claims 1 to 30 to the patient.

BRIEF DESCRIPTION OF THE DRAWINGS

FIG. 1. Diet induced obesity reversal data, for mice given a regular chow diet, a Western diet, or a Western diet plus compound 2-21.

DETAILED DESCRIPTION

Figure 1A:
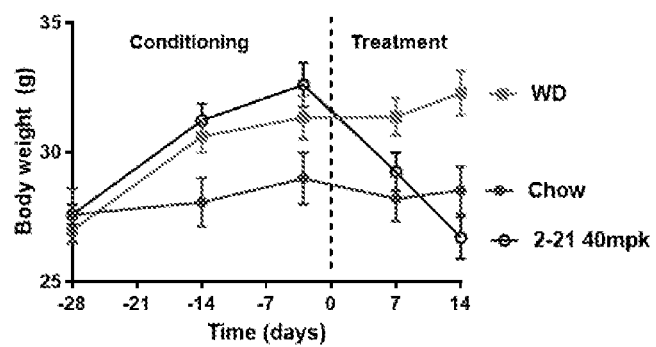
FIG. 1A, Body mass versus time.
Figure 1B:
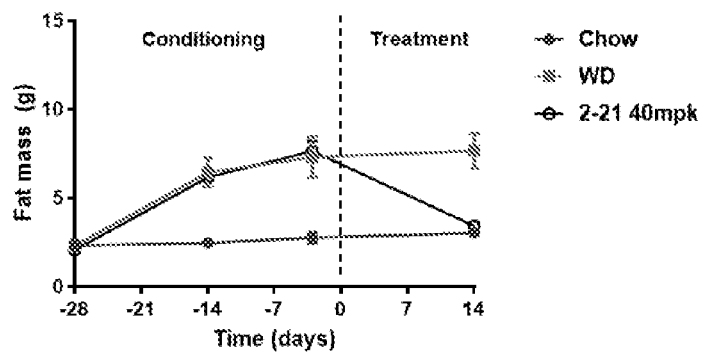
FIG. 1B, fat mass (measured by EchoMRI) versus time.
Figure 1C:
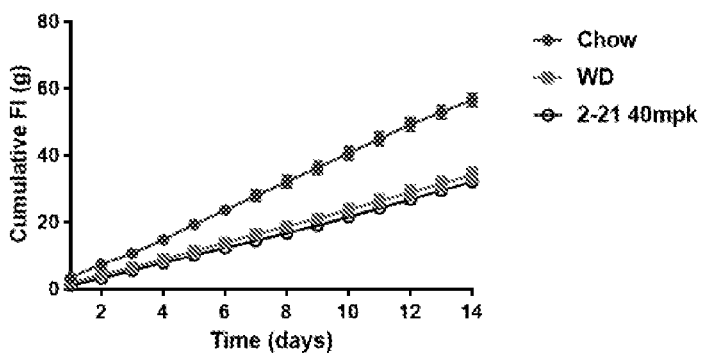
FIG. 1C, food intake (last 14 days) versus time.

In the description and claims, terms will carry the definitions set forth in this section unless the stated otherwise or contrary to the context. Unless defined otherwise, all technical and scientific terms used herein have the commonly understood by one of ordinary skill in the art to which the disclosure pertains. Although any methods and materials similar or equivalent to those described herein may be useful in the practice or testing of the embodiments of this disclosure; preferred methods and materials are described below.

The terms "a" and "an" do not denote a limitation of quantity, but rather denote the presence of at least one of the referenced item. The term "or" means "and/or". The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 30% means in the range of 45%-55%.

Numerical ranges recited herein by endpoints include all numbers and fractions subsumed within that range (e.g. 1 to 5 includes 1, 1.5, 2, 2.75, 3, 3.90, 4, and 5).

The terms "additional therapeutically active compound" or "additional therapeutic agent," refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the terms "administration of" and or "administering" a compound should be understood to mean providing a compound of the disclosure to a subject in need of treatment.

An "agonist" is a composition of matter which, when administered to a mammal such as a human, enhances or extends a biological activity attributable to the level or presence of a target compound or molecule of interest in the subject.

"Alleviating a disease or disorder symptom," means reducing the severity of the symptom or the frequency with which such a symptom is experienced by a subject, or both.

An "antagonist" is a composition of matter which when administered to a mammal such as a human, inhibits a biological activity attributable to the level or presence of a compound or molecule of interest in the subject.

A "Compound of Formula I-A or I-B" as used herein, refers to any compound within the scope of Formula I-A or I-B and, unless the context indicates otherwise, includes the pharmaceutically acceptable salts of Formula I-A and I-B.

The terms "comprises," "comprising," and the alternate transitional phrases "includes," "including," "contain," and "containing" are open ended transitional phrases having the meaning ascribed to them in U.S. Patent Law. "Comprises" and the other open-ended terms encompass the intermediate term "consisting essentially of" and the closed ended terms "consisting of" and "consists of." Claims reciting one of the open-ended transitional phrases can be written with any other transitional phrase, which may be more limiting, unless clearly precluded by the context or art.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary.

As used in the specification and the appended claims, the terms "for example," "for instance," "such as," "including" and the like are meant to introduce examples that further clarify more general subject matter. Unless otherwise specified, these examples are provided only as an aid for understanding the disclosure and are not meant to be limiting in any fashion.

The terms "formula" and "structure" are used interchangeably herein.

The term "inhibit," as used herein, refers to the ability of a compound of the disclosure to reduce or impede a described function, such as having inhibitory sodium channel activity. Preferably, inhibition is by at least 10%, more preferably by at least 23%, even more preferably by at least 30%, and most preferably, the function is inhibited by at least 73%. The terms "inhibit", "reduce", and "block" are used interchangeably herein.

As used herein "injecting or applying" includes administration of a compound of the disclosure by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of compound of the disclosure in the kit for effecting alleviation of the various diseases or disorders recited herein. Optionally, or alternately, the instructional material may describe one or more methods of alleviating the diseases or disorders in a cell or a tissue of a mammal. The instructional material of the kit of the disclosure may, for example, be affixed to a container which contains the identified disclosure compound or be shipped together with a container which contains the identified compound.

Alternatively, the instructional material may be shipped separately from the container with the intention that the instructional material and the compound be used cooperatively by the recipient.

The term, "mitochondrial uncoupling," also referred to as "uncoupling," refers to the process whereby protons enter the mitochondrial matrix via a pathway independent of ATP synthase and thereby uncouple nutrient oxidation from ATP production. This process can be pharmacologically induced by small molecule mitochondrial protonophores, which directly shuttle protons across the mitochondrial inner membrane into the matrix. The primary pathway for energy production in aerobic cells involves the oxidation of nutrients (including fats, carbohydrates, and amino acids) in mitochondria, which promotes the efflux of protons out of the mitochondrial matrix. This process creates a pH and electrochemical gradient across the mitochondrial inner membrane. Protons normally re-enter the mitochondrial matrix via ATP synthase, which results in ATP production. Protons can also re-enter the mitochondrial matrix via pathways independent of ATP synthase, which 'uncouples' nutrient oxidation and proton efflux from ATP production.

The term "modulate," means changing the level of an activity, function, or process. The term "modulate" encompasses both inhibiting and stimulating an activity, function, or process.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "per application" as used herein refers to administration of a compositions, drug, or compound to a subject.

The term "pharmaceutical composition" shall mean a composition comprising at least one active ingredient and a pharmaceutically acceptable carrier, such as a pharmaceutically acceptable excipient.

A "pharmaceutically acceptable excipient" means an excipient that is useful in preparing a pharmaceutical composition/combination that is generally safe, non-toxic and neither biologically nor otherwise undesirable, and includes an excipient that is acceptable for veterinary use as well as human pharmaceutical use. The term also encompasses any of the inactive agents approved for use pharmaceutical compositions in by a regulatory agency of the US Federal government or listed in the US Pharmacopeia for use in animals, including humans.

The term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

"Pharmaceutically acceptable" means physiologically tolerable, for either human or veterinary application. As used herein, "pharmaceutical compositions" include formulations for human and veterinary use.

"Plurality" means at least two.

The term "prevent," as used herein, means to stop something from happening or to significantly reduce the likelihood of something happening, such as by taking advance measures against something possible or probable outcome. In the context of medicine, "prevention" includes an action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

A "subject" of analysis, diagnosis, or treatment is an animal. Such animals include mammals, preferably a human. As used herein, a "subject in need thereof" is a patient, animal, mammal, or human, who will benefit from the method of this disclosure.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, "treat," "treating", or "treatment" includes treating, ameliorating, or inhibiting an injury or disease related condition or a symptom of an injury or disease related condition. In one embodiment the disease, injury or disease related condition or a symptom of an injury or disease related condition is prevented; while another embodiment provides prophylactic treatment of the injury or disease related condition or a symptom of an injury or disease related condition.

Chemical Definitions

"Alkyl" is a branched or straight chain saturated aliphatic hydrocarbon group, having the specified number of carbon atoms, generally from 1 to about 8 carbon atoms. The term $C_1$-$C_6$-alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. $C_1$-$C_8$-alkyl, $C_1$-$C_4$-alkyl, and $C_1$-$C_2$-alkyl. Examples of alkyl include, but are not limited to, methyl, ethyl, n-propyl, isopropyl, n-butyl, 3-methylbutyl, t-butyl, n-pentyl, sec-pentyl, heptyl, and octyl. "$C_0$-$C_n$ alkyl" is used together with another group, e.g. $C_0$-$C_4$alkyl($C_3$-$C_7$cycloalkyl), to indicate the other group, in this case $C_3$-$C_7$cycloalkyl, is bound to the group it substitutes either by a single covalent bond ($C_0$) or attached through an alkylene linker having the indicated number of carbon atoms.

"Alkenyl" is a branched or straight chain aliphatic hydrocarbon group having one or more double carbon-carbon bonds that may occur at any stable point along the chain, having the specified number of carbon atoms. Examples of alkenyl include, but are not limited to, ethenyl, propenyl, 1,3-butadienyl, 1-butenyl, hexenyl, and pentenyl.

"Alkynyl" is a branched or straight chain aliphatic hydrocarbon group having one or more triple carbon-carbon bonds that may occur at any stable point along the chain, having the specified number of carbon atoms. Examples of alkynyl include, but are not limited to, ethynyl, propynyl, 1-butynyl, 2-butynyl, and 1-pentynyl.

"Alkanoyl" is an alkyl group as defined above covalently bound to the group it substitutes by an carbonyl bridge (—C(=O)—). The carbonoyl oxygen is included in the count of carbons in the substituted group. A $C_2$alkanoyl is —C(=O)$CH_3$.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkylamino" is an alkyl group as defined herein covalently bound to the group it substitutes by an amino linkage. An alkylamino group can be a mono-alkyl group in which the amino is a secondary amino (alkylNH—) or a di-alkyl group in which the amino is a tertiary amino (alkyl1)(alkyl2) N—. The alkyl groups of a di-alkylamino are the same or different.

"Alkylester" is an alkyl group as defined herein covalently bound to the group it substitutes by an ester linkage. The ester linkage may be in either orientation, e.g., a group of the formula —OC(O)-alkyl or a group of the formula —C(O)O-alkyl.

"Aryl" indicates a mono-, bi- or tri-cyclic ring system having at least one aromatic ring. Aryl groups contain only carbon in the aromatic ring or rings. An aryl group may be fused to a non aromatic ring containing N, O, or S heteroatoms. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Example include phenyl, naphthyl, biphenyl, tetrahydronaphthyl, indanyl, and indenyl group.

"Cycloalkyl" is a saturated hydrocarbon ring group, having the specified number of carbon atoms. Monocyclic cycloalkyl groups typically have from 3 to about 8 carbon ring atoms, from 3 to 7 ring atoms, or from 3 to 6 (3, 4, 3, or 6) carbon ring atoms. Cycloalkyl substituents may be pendant from a substituted nitrogen, oxygen, or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

A "bridged cycloalkyl" is a cycloalkyl group that has two or more rings containing only carbon ring atoms, and one of the carbon rings contains a "bridge" of 1 carbon atom or 2-3 unbranched carbon atoms connected to two "bridgehead" atoms in the carbon ring. The bridgehead atoms are usually non-adjacent carbon ring atoms. Examples of bridge cycloalkyl groups include, but are not limited to, bicyclo [2.2.2]octanyl, bicyclo[3.3.1]nonanyl, adamantanyl, and and bicyclo[3.3.3]undecanyl groups.

"Halogen" or "halo" includes bromo, chloro, fluoro, and iodo.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, 2,2,2-trifluoroethyl, and penta-fluoroethyl.

"Haloalkoxy" indicates a haloalkyl group as defined herein attached through an oxygen bridge (oxygen of an alcohol radical).

"Halosulfanyl" is a sulfur substituted with one or more halogen atoms, up to the maximum allowable number of halogen atoms.

"Heteroaryl" is a ring or ring system having at least one aromatic ring containing a heteroatom independently chosen from N, O, and S with remaining ring atoms being carbon. Fused rings may or may not contain heteroatoms and need not be aromatic. It is preferred that the total number of heteroatoms in a heteroaryl ring system is not more than 4 and that the total number of S and O atoms in a heteroaryl ring system is not more than 2. Monocyclic heteroaryl groups typically have from 3 to 7 ring atoms. In some embodiments bicyclic heteroaryl groups are 9- to 10-membered heteroaryl groups, that is, groups containing 9 or 10 ring atoms in which one 3- to 7-member aromatic ring is fused to a second aromatic or non-aromatic ring. When the total number of S and O atoms in an aromatic ring of the heteroaryl group exceeds 1, these heteroatoms are not adjacent to one another. Examples of heteroaryl groups include, but are not limited to, oxazolyl, pyranyl, pyrazinyl, pyrazolopyrimidinyl, pyrazolyl, pyridazinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

"Heterocycloalkyl" is a saturated cyclic group containing 1 or more ring atoms independently chosen from N, O, and S with remaining ring atoms being carbon. Examples of heterocycloalkyls include tetrahydropyranyl, tetrahydrofuranyl, piperidinyl, piperazinyl, morpholinyl, thiomorpholinyl, oxazolidinyl, tetrahydrothiophenyl, tetrahydrothiopyranyl, thiazolidinyl, and pyrrolidinyl.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Alkali metal (for example, sodium, potassium or lithium) or alkaline earth metal (for example calcium) salts of organic (e.g., carboxylic) acids can also be made.

Such reactions are typically carried out in water or in an organic solvent, or in a mixture of the two.

Examples of pharmaceutically acceptable salts include, but are not limited to, mineral or organic acid salts of basic residues such as amines or nitrogen-containing heteroaryl rings (e.g. pyridine, quinoline, isoquinoline); alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, phosphoric, nitric and the like; and the salts prepared from organic acids such as acetic, propionic, succinic, glycolic, stearic, lactic, malic, malonic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, succinic, toluenesulfonic, methanesulfonic, ethane disulfonic, oxalic, α-ketoglutarate, α-glycerophosphate, isethionic, $HO_2C—(CH_2)_n—CO_2H$ where n is 0-4, and the like.

Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, Nalkylglucamines, theobromine, purines, piperazine, piperidine, morpholine, Nethylpiperidine, and the like. It should also be understood that other carboxylic acid derivatives would be useful in the practice of this disclosure, for example, carboxylic acid amides, including carboxamides, lower alkyl carboxamides, dialkyl carboxamides, and the like.

Lists of additional suitable salts may be found, e.g., in G. Steffen Paulekuhn, et al., *Journal of Medicinal Chemistry* 2007, 50, 6665 and *Handbook of Pharmaceutical Salts: Properties, Selection and Use*, P. Heinrich Stahl and Camille G. Wermuth Editors, Wiley-VCH, 2002.

The term "substituted" means that any one or more hydrogens on the designated atom or group is replaced with a selection from the indicated group, provided that the designated atom's normal valence is not exceeded. Unless otherwise specified, each substituent is selected independently of other substituents. "Optionally substituted" means that 0 to the maximum allowable number of substituents are present. When the substituent is oxo (i.e., =O) then 2 hydrogens on the atom are replaced. When an oxo group substitutes a heteroaromatic moiety, the resulting molecule can sometimes adopt tautomeric forms. For example a pyridyl group substituted by oxo at the 2- or 4-position can sometimes be written as a pyridine or hydroxypyridine. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group. However, a dash ("-") indicates a point of attachment for a substituent. —$C_1$-$C_4$alkyl(cycloalkyl) is attached at the 1 to 4 carbon alkylene tinker.

The disclosure includes deuterated compounds of Formula I-A and I-B in which any hydrogen is replaced by a deuterium. "Deuterated" mean that a hydrogen at the specified position is replaced by deuterium. In any sample of a compound of Formula I-A or I-B in which a position is deuterated some discrete molecules of the compound of Formula I-A or I-B will likely have hydrogen, rather than deuterium, at the specified position. However, the percent of molecules of the compound of Formula I-A or I-B in the sample which have deuterium at the specified position will be much greater than would naturally occur. The deuterium at the deuterated position is enriched. The term "enriched" as used herein, refers to the percentage of deuterium versus other hydrogen species at that location. As an example, if it is said that a position in the compound of Formula I contains 50% deuterium enrichment, that means that rather than hydrogen at the specified position the deuterium content is 50%. For clarity, it is confirmed that the term "enriched" as used herein does not mean percentage enriched over natural abundance. In one embodiment, deuterated compounds of Formula I-A or I-B will have at least 10% deuterium enrichment at any deuterated position. In other embodiments, there will be at least 50%, at least 90%, or at least 95% deuterium enrichment at the specified deuterated position or positions. A "deuterated substituent" is a substituent in which at least one hydrogen is replaced by deuterium at the specified percent enrichment.—"Optionally deuterated" means that the position may be either hydrogen and the amount of deuterium at the position is only the naturally occurring level of deuterium or the position is enriched with deuterium above the naturally occurring deuterium level.

Certain compounds of the disclosure may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column. In addition, compounds with carbon-carbon double bonds may occur in Z- and E-forms, with all isomeric forms of the compounds being included in the present disclosure.

Where a compound exists in various tautomeric forms, the disclosure is not limited to any one of the specific tautomers, but rather includes all tautomeric forms. The compounds of the disclosure may exist in tautomeric forms. Both mixtures and separate individual tautomers are included. For example

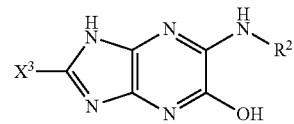

also includes

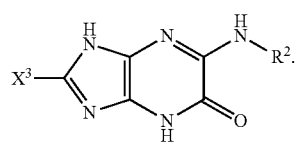

Chemical Description

The disclosure provides compounds of Formula I-A and I-B, and the pharmaceutically acceptable salts thereof:

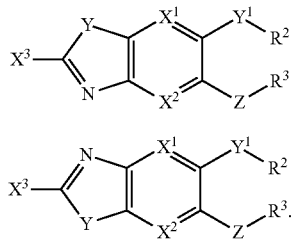

Formula I-A

Formula I-B

The variables, e. g., R, $R^2$, $R^2$, $X^1$, $X^2$, $X^3$, Y, $Y^1$, or Z in Formula I-A and I-B may carry any of the definitions set forth in the SUMMARY section, or may carry any of the values set forth below.

Formula I also includes subformulae in which the variables carry any of the following definitions. Any of the variable definitions below can be combined so long as a stable compound results.

Y can be N—R.
Y ean be O.
$X^1$ and $X^2$ can both be nitrogen.
Z can be O; and $X^1$ and $X^2$ can both be nitrogen.
One of $X^1$ and $X^2$ can be nitrogen and the other can be carbon.
Z can be O and one of $X^1$ and $X^2$ can be nitrogen and the other can be carbon.

The $X^3$ Variable
$X^3$ may carry the following definitions.
(i) $X^3$ is hydrogen.
(ii) $X^3$ is methyl, trifluoromethyl, pentafluoroethyl, phenyl, or fluoro-substituted phenyl.
(ii) $X^3$ is trifluoromethyl.

The R and $R^1$ Variables
R and $R^1$ may carry the following definitions.
(i) R is hydrogen.
(ii) Y is $NR^1$ and $R^1$ is hydrogen or unsubstituted $C_1$-$C_6$alkyl.
(iii) Y is $NR^1$ and $R^1$ is $R^1$ is hydrogen.

The $R^2$ Variable
$R^2$ may carry the following definitions
(i) $R^2$ is —$C_0$-$C_4$alkyl($C_3$-$C_7$cycloalkyl), —$C_0$-$C_4$alkyl(bridged $C_7$-$C_{12}$cycloalkyl), —$C_0$-$C_4$alkyl(aryl), —$C_0$-$C_4$alkyl(mono- or bi-cyclic heteroaryl), or —$C_0$-$C_4$alkyl(4- to 7-membered heterocycloalkyl), each of which is optionally substituted with one or more substituents independently chosen from $R^{11}$ and 0 or 1 substituents $R^{12}$;

in each $C_0$-$C_4$alkyl one or more carbon atoms is optionally replaced by O, $NR^{10}$, —C(O)—, —C(O)O—, —OC(O), —S(O)n-, —C(O)$NR^{10}$—, or —$NR^{10}$C(O)— where n is 0, 1, or 2, and in which the $C_0$-$C_4$alkyl, $C_1$-$C_8$ alkyl, $C_2$-$C_8$alkenyl, or $C_2$-$C_8$alkynyl is optionally substituted with one or more substituents $R^{13}$.

(ii) $R^2$ is $C_1$-$C_8$alkyl, optionally substituted with one or more substituents independently chosen from halogen, hydroxyl, amino, nitro, cyano, and oxo.

(iii) $R^2$ is —$C_0$-$C_4$alkyl(bridged $C_7$-$C_{12}$cycloalkyl) or —$C_0$-$C_4$alkyl(aryl), each of which is optionally substituted with one or more substituents independently chosen from $R^{11}$ and 0 or 1 substituents $R^{12}$; in $C_0$-$C_4$alkyl one or more carbon atoms is optionally replaced by O, $NR^{10}$, —C(O)—, —C(O)O—, —OC(O), —S(O)n-, —C(O)$NR^{10}$—, or —$NR^{10}$C(O)— where n is 0, 1, or 2, and in which the $C_0$-$C_4$alkyl is optionally substituted by $R^{13}$.

(iv) $R^2$ is —$C_0$-$C_4$alkyl(bridged $C_7$-$C_{12}$cycloalkyl) or —$C_0$-$C_4$alkyl(aryl), each of which is optionally substituted with one or more substituents independently chosen from $R^{11}$ and 0 or 1 substituents $R^{12}$; in $C_0$-$C_4$alkyl one or more carbon atoms is optionally replaced by O, $NR^{10}$, —C(O)—, —C(O)O—, —OC(O), —S(O)n-, —C(O)$NR^{10}$—, or —$NR^{10}$C(O)— where n is 0, 1, or 2, and in which the $C_0$-$C_4$alkyl is optionally substituted by $R^{13}$.

(v) $R^2$ is $C_0$-$C_2$alkyl(bridged $C_7$-$C_{12}$cycloalkyl), which is optionally substituted with one or more substituents independently chosen from $R^{11}$.

(vi) $R^2$ is adamantan-1-yl or —$CH_2$(adamantan-1-yl), each of which is unsubstituted or substituted with halogen, hydroxyl, amino, nitro, cyano, $C_1$-$C_4$alkyl, $C_1$-$C_4$alkoxy, —$C_0$-$C_2$alkyl(mono- or di-$C_1$-$C_4$alkylamino), $C_1$-$C_2$haloalkyl, and $C_1$-$C_2$haloalkoxy.

(vii) $R^2$ is —$C_0$-$C_4$alkyl(phenyl), naphthyl, or fluorenyl, each of which is optionally substituted with one or more substituents independently chosen from $R^{11}$ and 0 or 1 substituents $R^{12}$; in $C_0$-$C_4$alkyl one or more carbon atoms is optionally replaced by O, $NR^{10}$, —C(O)—, —C(O)O—, —OC(O), —S(O)n-, —C(O)$NR^{10}$—, or —$NR^{10}$C(O)— where n is 0, 1, or 2, and in which the $C_0$-$C_4$alkyl is optionally substituted by $R^{13}$.

(viii) $R^2$ is phenyl, which is optionally substituted by one or more substituents independently chosen from $R^{11}$.

(ix) $R^2$ is phenyl, which is optionally substituted by one or more substituents independently chosen from halogen, hydroxyl, amino, nitro, cyano, oxo, halosulfanyl, and $C_1$-$C_8$alkyl, $C_2$-$C_8$alkenyl, and $C_2$-$C_8$alkynyl, wherein in each $C_1$-$C_8$alkyl, $C_2$-$C_8$alkenyl, and $C_2$-$C_8$alkynyl, in the definition of $R^{11}$ one or more carbon atoms is optionally replaced by O, $NR^{10}$, —C(O)O—, —OC(O), or —S(O)n-, where n is 0, 1, or 2, and in which each $C_1$-$C_8$alkyl, $C_2$-$C_8$alkenyl, or $C_2$-$C_8$alkynyl is optionally substituted with one or more substituents $R^{13}$.

(x) $R^2$ is —$C_0$-$C_4$alkyl(phenyl), which is optionally substituted with one or more substituents independently chosen from $R^{11}$ and 0 or 1 substituents $R^{12}$; in $C_0$-$C_4$alkyl one or more carbon atoms is optionally replaced by O, $NR^{10}$, —C(O)—, —C(O)O—, —OC(O), —S(O)n-, —C(O)$NR^{10}$—, or —$NR^{10}$C(O)— where n is 0, 1, or 2, and in which the $C_0$-$C_4$alkyl is optionally substituted by $R^{13}$;

$R^{12}$ is selected from —$C_0$-$C_4$alkyl($C_3$-$C_7$cycloalkyl), —O—$C_0$-$C_4$alkyl($C_3$-$C_7$cycloalkyl), —$C_0$-$C_4$alkyl(phenyl), —O—$C_0$-$C_4$alkyl(phenyl), —$C_0$-$C_4$alkyl(5- to 6-membered heteroaryl), —O—$C_0$-$C_4$alkyl(5- to 6-membered heteroaryl), each of which is optionally substituted with one or more substituents independently chosen from halogen, hydroxyl, amino, nitro, cyano, —CHO, —COOH, oxo, $C_1$-$C_2$haloalkyl, $C_1$-$C_2$haloalkoxy, $C_1$-$C_6$alkyl, $C_1$-$C_6$alkoxy, $C_1$-$C_6$alkylester, —$C_0$-$C_4$alkyl(mono- or di-$C_1$-$C_6$alkylamino), $C_2$-$C_6$alkanoyl, $C_2$-$C_6$alkenyl, and $C_2$-$C_6$alkynyl.

(xi) $R^2$ is naphthyl, or
$R^2$ is phenyl, which is substituted with 1, 2, or 3 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy, or $R^2$ is phenyl, which is optionally substituted with 1 or 2 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy, and which is substituted with one phenyl substituent, which phenyl substituent is optionally substituted with 1, 2, or 3 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy.

The $R^3$ Variable $R^3$ may carry any of the following definitions.
(i) $R^3$ is hydrogen.
(ii) $R^3$ is $C_1$-$C_8$alkyl, $C_2$-$C_8$alkenyl, or $C_2$-$C_8$alkynyl, In the $C_1$-$C_8$alkyl, $C_2$-$C_8$alkenyl, or $C_2$-$C_8$alkynyl one or more carbon atoms is optionally replaced by O, $NR^{10}$, C(O)O—, —OC(O), or —S(O)n-, where n is 0, 1, or 2, and in which the $C_1$-$C_8$ alkyl, $C_2$-$C_8$alkenyl, or $C_2$-$C_8$alkynyl is optionally substituted with one or more substituents $R^{13}$.
(iii) $R^3$ is $C_1$-$C_6$alkyl optionally substituted with hydroxyl, halogen, trifluoromethyl, or trifluoromethoxy.
(iv) $R^3$ is —$C_0$-$C_4$alkyl($C_3$-$C_7$cycloalkyl) or —$C_0$-$C_4$alkyl(aryl), which is optionally substituted with one or more independently chosen $R^{11}$ substituents.

In an embodiment, the disclosure includes a compounds and the salts thereof of Formula I-A and I-B in which the variables carry the following definitions.

$Y^1$ is $NR^1$ and $R^1$ is hydrogen or methyl; and
$R^2$ is naphthyl, or
$R^2$ is phenyl, which is substituted with 1, 2, or 3 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy, or
$R^2$ is phenyl, which is optionally substituted with 1 or 2 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy, and which is substituted with one phenyl substituent, which phenyl substituent is optionally substituted with 1, 2, or 3 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy.

In another embodiment the disclosure includes a compound of Formula I-A or I-B, wherein the variables carry the following definitions.

$X^1$ and $X^2$ are both N;
$X^3$ is hydrogen, methyl, trifluoromethyl, pentafluoroethyl, phenyl, or 3-fluorophenyl;
Y is $NR^1$ and $R^1$ is hydrogen or methyl;
Z is O;
R is hydrogen or methyl;
$R^1$ is hydrogen or $C_1$-$C_2$alkyl;
$R^2$ is naphthyl, or
$R^2$ is phenyl, which is substituted with 1, 2, or 3 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy, or
$R^2$ is phenyl, which is optionally substituted with 1 or 2 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy, and which is substituted with one phenyl substituent, which phenyl substituent is optionally substituted with 1, 2, or 3 substituents independently chosen from halogen, hydroxyl, $C_1$-$C_6$alkyl, $C_1$-$C_6$alkoxy, $C_1$-$C_2$haloalkyl, and $C_1$-$C_2$haloalkoxy; and
$R^3$ is H or $C_1$-$C_6$alkyl optionally substituted with hydroxyl or trifluoromethyl.

Processes for preparing compounds of a formula of the disclosure, such as a generic of the disclosure, or for preparing intermediates useful for preparing compounds of Formula I-A or I-B or other formulas of the disclosure are provided as further embodiments. Intermediates useful for preparing compounds of Formula I-A or I-B or other formulas are also provided as further embodiments of the disclosure.

Pharmaceutical Compositions

The disclosure includes a pharmaceutical composition comprising a compound or salt thereof of the disclosure, together with a pharmaceutically acceptable excipient.

This disclosure provides pharmaceutical compositions comprising compounds of the Formula I-A or I-B. The pharmaceutical composition may comprise one or more compounds of the disclosure and pharmaceutically acceptable salts thereof, and a pharmaceutically acceptable carrier. In one embodiment, the compounds are administered as a pharmaceutical composition.

The route of administration can vary depending on the type of compound being administered. In one aspect, the compounds are administered via routes such as oral, topical, rectal, intramuscular, intramucosal, intranasal, inhalation, ophthalmic, and intravenous.

The present disclosure further provides for administration of a compound of Formula I-A or I-B as an immediate release or as a controlled-release formulation.

The dosage of the active compound(s) being administered will depend on the condition being treated, the particular compound, and other clinical factors such as age, sex, weight, and health of the subject being treated, the route of administration of the compound(s), and the type of composition being administered (tablet, gel cap, capsule, solution, suspension, inhaler, aerosol, elixir, lozenge, injection, patch, ointment, cream, etc.). It is to be understood that the present disclosure has application for both human and veterinary use.

Processes for preparing compounds of any of the formulas of the disclosure or for preparing intermediates useful for preparing compounds of any of the formulas of the disclosure are provided as further embodiments. Intermediates useful for preparing compounds of Formula I-A and I-B are also provided as further embodiments of the disclosure.

Processes for preparing compounds of any of the formulas of the disclosure are provided as further embodiments of the disclosure and are illustrated by the following procedures in which the meanings of the generic radicals are as given above unless otherwise qualified.

In one embodiment, compounds of the disclosure may be systemically administered, e.g., orally, in combination with a pharmaceutically acceptable carrier such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula I-A and I-B to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the disclosure can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the disclosure in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%. The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

For example, in one embodiment relating to oral administration to humans, a dosage of between approximately 0.1 and 300 mg/kg/day, or between approximately 0.5 and 50 mg/kg/day, or between approximately 1 and 10 mg/kg/day, is generally sufficient, but will vary depending on such things as the disorder being treated, the length of treatment, the age, sex, weight, and/or health of the subject, etc. In one aspect, a unit dose is used. In one aspect, the unit dose is supplied in a syringe. The combinations of drugs can be administered in formulations that contain all drugs being used, or the drugs can be administered separately. In some cases, it is anticipated that multiple doses/times of administration will be required or useful. Additionally, for some treatment regimens, at least two compounds will be used. In one aspect, at least three compounds will be administered. The present disclosure further provides for varying the length of time of treatment.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, when the active ingredient needs to enter circulation and be delivered via blood, the active ingredient, in one embodiment, should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Pharmaceutical compositions of the disclosure can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof. Non-synthetic matrix proteins like collagen, glycosaminoglycans, and hyaluronic acid, which are enzymatically digested in the body, are useful for delivery (see U.S. Pat. Nos. 4,394,320; 4,472,840; 5,366,509; 5,606,019; 5,645,591; and 5,683,459) and are suitable for use with the present disclosure. Other implantable media and devices can be used for delivery of the compounds of the disclosure in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The compounds of the present disclosure can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of this disclosure can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

Examples of other antimicrobial agents that can be used in the present disclosure include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

In one embodiment, the compounds of the disclosure can first be encapsulated into microcapsules, microspheres, microparticles, microfibers, reinforcing fibers and the like to facilitate mixing and achieving controlled, extended, delayed and/or sustained release and combined other agents or drugs. Encapsulating the biologically active agent can also protect the agent against degradation during formation of the composite of the disclosure.

In another embodiment of the disclosure, the compound is controllably released into a subject when the composition of the disclosure is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

As used herein, an "instructional material" includes a publication, a recording, a diagram, or any other medium of expression which can be used to communicate the usefulness of the composition of the disclosure for its designated use. The instructional material of the kit of the disclosure may, for example, be affixed to a container which contains the composition or be shipped together with a container which contains the composition. Alternatively, the instructional material may be shipped separately from the container with the intention that the instructional material and the composition be used cooperatively by the recipient.

The method of the disclosure includes a kit comprising a compound identified in the disclosure and an instructional material which describes administering the compound or a composition comprising the compound to a a subject. This should be construed to include other embodiments of kits that are known to those skilled in the art, such as a kit comprising a (preferably sterile) solvent suitable for dissolving or suspending the composition of the disclosure prior to administering the compound to a subject. Preferably the subject is a human.

In accordance with the present disclosure, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present disclosure.

Methods of Treatment

Mitochondria regulate cellular metabolism and play an important role in the pathogenesis of some of the most prevalent human diseases including obesity, cancer, diabetes, neurodegeneration, and heart disease. The compounds of the disclosure, including are useful for treating and preventing these diseases and disorders and others described herein, as well as others where a mitochondrial uncoupler is useful.

Many anti-diabetes drugs such as insulin-sensitizers promote glucose clearance from the blood by effectively 'pushing' glucose into nutrient overloaded tissues; however, in contrast to this approach our strategy is aimed at reducing cellular nutrient stores so that tissues will 'pull' glucose from the circulation. The present method is modeled after exercise and calorie restriction interventions which also reduce cellular nutrient stores to improve glycemia and insulin sensitivity. The proof of principle is validated in humans treated with the mitochondrial uncoupler 2,4-dinitrophenol (DNP). DNP decreases adiposity and improves metabolism in humans; however, it also has a very narrow therapeutic window and was removed from FDA approval in 1938. Other anti-diabetes drugs including agonists of thyroid hormone and inhibitors of 11-β hydroxysteroid dehydrogenase type 1 have off-target effects of increased energy expenditure that may mediate some of the protective effects of these compounds. Nevertheless, there are no drugs have been specifically targeted for increased energy expenditure.

In one embodiment, a compound of the disclosure is useful for treating disease, disorders, and conditions which are associated with defects in mitochondrial function or which can be treated with drugs or agents that act as uncoupling agents. The methods can comprise administering to a subject in need thereof a pharmaceutical composition comprising an effective amount of compound of Formula I-A or I-B, or a salt thereof as a first therapeutic agent, together with a pharmaceutically acceptable carrier, and optionally with at least one additional therapeutic agent.

In one embodiment, the present disclosure provides compositions and methods for increasing oxygen consumption, decreasing cellular reactive oxygen species, depolarizing a mitochondrial inner membrane, and increasing oxygen consumption rate without donating electrons to the electron transport chain using a mitochondrial uncoupler, said method comprising contacting a cell or mitochondria with a composition comprising at least one compound of the disclosure and optionally an additional therapeutic agent.

For example, it is disclosed herein that the mitochondrial uncoupling agents of this disclosure both prevent and reverse body fat mass increases in mice fed a high fat and high sugar Western diet. Apart from body fat, the mitochondrial uncoupling agents decrease insulin levels, which is important because it corrects hyperinsulinemia, improves glucose tolerance, and protect against diet-induced glucose tolerance. It is also disclosed herein that administration of the mitochondrial uncoupling agents reverses insulin resistance, including diet-induced insulin resistance, and restores insulin sensitivity index. Therefore, the compounds of the disclosure are useful for preventing and treating diabetes. It is also disclosed that compounds of the disclosure decrease liver fat, thus providing a treatment for fatty liver disease. It is disclosed herein that a compound of the disclosure can prevent weight gain without altering food intake and can prevent di-t-induced fat accumulation. Compounds of the disclosure are also useful for reversing diet-induced weight or fat gain and can reverse diet-induced fat gain and fatty liver.

Reactive oxygen species generated during respiration contribute to biological damage over time, causing mutations and other biological changes that lead to cancer, aging, and decreased lifespan. Mitochondrial uncoupling decreases the production of reactive oxygen species, potentially lowering the risk of cancer, decreasing the effects of aging, and increasing lifespan. Mitochondrial uncouplers reverse or interfere with many aspects of cancer metabolism and are therefore effective in a broad range of cancer types. For example, mitochondrial uncouplers are effective in treatment of cancers with impaired p53 expression or activity (https://www.nature.com/articles/s41467-018-05805-1) such as certain breast and ovarian cancers, Ras mutant cancers (https://www.cell.com/molecular-cell/pdf/S1097-2763(13)00004-0.pdf), and/or beta-catenin mutant cancers (https://www.ncbi.nlm.nih.gov/pubmed/28107388). Mitochondrial uncouplers are demonstrated to treat adrenocortical carcinoma (http://clincancerres.aacrjournals.org/content/clincanres/early/2016/02/12/1078-0432.CCR-15-2256.full.pdf) melanoma (https://www.ncbi.nlm.nih.gov/pmc/articles/PMC5833689/), primary colon cancer (https://www.ncbi.nlm.nih.gov/pmc/articles/PMC6056247/) and metastasis to distant organs including the liver (https://www.nature.com/articles/s41419-017-0092-6).

A compound of the disclosure may exhibit at least one of the following properties or activities: energy expenditure agonist, mitochondrial uncoupler, antioxidant, increases oxygen consumption, depolarizes the mitochondrial inner membrane, stimulates respiration in isolated mitochondria, increases or stimulates oxygen consumption without donating electrons to the electron transport chain, lacks protonophore activity at the plasma membrane, decreases reperfusion-induced mitochondrial oxidative stress, decreases cellular reactive oxygen species, improves glucose tolerance, provides protection from high fat induce glucose tolerance, activates AMPK without depletion of ATP, prevents, reverses or treats insulin resistance, prevents, reverses or treats hyperinsulinemia, prevents, reverses or treats hyperlipidemia, improves blood lipid profiles, improves leanness, improves insulin sensitivity, protects from ischemic-reperfusion injury, and is less toxic than other mitochondrial inhibitors. In one embodiment, a compound of the disclosure has two or more of these properties. In one embodiment, a compound of the disclosure has three or more of these properties. In one embodiment, a compound of the disclosure has four, five, six, seven, eight, nine, ten, eleven, twelve, or more of these properties. In one embodiment, a compound of the disclosure has one, two, three, four, five, six, seven, eight, nine, or ten of these properties.

Compounds of the disclosure can be administered to a subject at various times, dosages, and more than once, depending on, for example, the age, sex, health, and weight of the subject, as well as on the particular disease, disorder, or condition to be treated or prevented. In one aspect, a compound is administered at a dosage ranging from about 0.1 mg/kg to about 500 mg/kg body weight. In another aspect, the compound is administered at a dosage ranging from about 0.5 mg/kg to about 100 mg/kg body weight or about 0.5 mg/kg to about 25 mg/kg body weight. In yet another aspect, the compound is administered at a dosage ranging from about 1.0 mg/kg to about 50 mg/kg body weight. In one aspect, about 3.0 mg/kg is administered. In another aspect, about 5.0 mg/kg is administered. In one aspect, the dose is selected from 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 300, 400, and 500 mg/kg body weight, as well as all fractions, decimals, and integers in the range of numbers listed. In another aspect, the compound is administered as a unit dose ranging from about 10 mg to about 500 mg/unit dose.

In one aspect, a compound is administered to a subject more than once. In one aspect, the compound is a mitochondrial protonophore uncoupler lacking protonophore activity at the plasma membrane.

In one aspect the disclosure provides a method of treating or preventing a condition responsive to mitochondrial uncoupling, comprising administering a therapeutically effective amount of a compound Formula I-A or I-B I or salt thereof to a patient in need of such treatment.

In one aspect, the disease, disorder or condition associated with a defect in mitochondria function is selected from the group consisting of obesity, ischemia reperfusion injury, hyperinsulinemia, hyperlipidemia, glycemia, glucose tolerance, insulin sensitivity, adiposity, insulin resistance, obesity, diabetes, cancer, neurodegeneration, heart disease, renal disease, heart failure, Parkinson's disease, traumatic brain injury, stroke, aging, and disorders standing to benefit from increased energy expenditure. In one aspect, the compound is a mitochondrial uncoupler.

In one aspect the condition responsive to mitochondrial uncoupling is obesity, type II diabetes, fatty liver disease, insulin resistance, cancer, multiple sclerosis, Huntington's disease, Alzheimer's dementia, Parkinson's disease, ischemia reperfusion injury, heart failure, non-alcoholic fatty liver disease (NALFD), or non-alcoholic steatohepatitis (NASH).

The disclosure also includes a method of increasing lifespan comprising administering an effective amount of a compound of Formula I, or salt thereof, to a human or non-human animal. Increasing lifespan can be via delaying aging by delaying the onset of age-related disease, or age related changes, including neurodegenerative diseases, an age related cognitive decline, or an age-related decrease in motorneuron responses. The disclosure includes a method of increasing lifespan by delaying the onset of diseases associated with aging, comprising administering an effective amount of a compound of Formula I, or salt thereof, to a human or non-human animal.

The disclosure includes a method of regulating glucose homeostasis or insulin action in a patient comprising administering a therapeutically effective amount of a compound or salt of any one of Formula I-A or I-B to the patient.

The disclosure includes a method of treating hyperlipidemia, glycemia, glucose tolerance, insulin sensitivity, adiposity, insulin resistance, obesity, or diabetes in a patient comprising administering a therapeutically effective amount of a compound of Formula I-A or I-B to the patient.

One of ordinary skill in the art will appreciate that not all configurations need to be effective or as effective as other compounds of the genus based on the teachings disclosed herein.

The disclosure is now described with reference to the following Examples and Embodiments. Without further description, it is believed that one of ordinary skill in the art can, using the preceding description and the following illustrative examples, make and utilize the present disclosure and practice the claimed methods. The following working examples therefore, are provided for the purpose of illustration only and specifically point out the preferred embodiments of the present disclosure, and are not to be construed as limiting in any way the remainder of the disclosure. Therefore, the examples should be construed to encompass any and all variations which become evident as a result of the teaching provided herein.

EXAMPLES

General Methods

The following starting materials and general procedures are used in synthetic examples that follow.

In all synthetic examples room temperature (rt) is about 21° C.

NMR Solvent Reference: $(CD_3)_2CO$ (2.05/29.84 ppm); $(CD_3)_2SO$ (2.50/39.52 ppm).

NMR Abbreviations: aq.=aqueous, app=apparent, br=broad, s=singlet, d=doublet, t=triplet, q=quartet, p=pentet. * means rotamers.

IMIDAZOLE-PYRAZINE SERIES

General Procedure A. For Preparation of 5-Methoxy Compounds

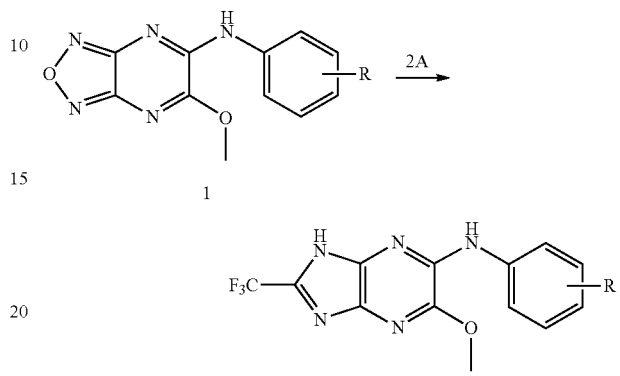

In a six dram vial, the desired oxadiazole-pyrazine 1 (0.2 mmol), iron (1 mmol), ytterbium (III)triflate (0.02 mmol) were dissolved in glacial acetic acid (0.45 mL) and the desired fluorinated ester (ethyl trifluoroacetate or methyl pentafluoropropionate) (2 mL); the mixture was stirred vigorously at 95° C. for 4 hours. After cooling down to rt, 5 mL $H_2O$ and 5 mL EtOAc were added to the reaction mixture and it was filtered through Celite pad. The organic layer was separated, and the aqueous layer was extracted with EtOAc three times. The organic layers were combined, washed with a saturated $NaHCO_3$ aqueous solution, dried over $Na_2SO_4$, and concentrated under reduced pressure. The residue was purified by silica gel column chromatography (0-20% EtOAc/hexanes) to yield the desired 5-methoxy-2-trifluoromethyl-N-phenyl-1H-imidazo[4,5-b]pyrazin-6-amine as a light yellow solid.

General Procedure 2B. For Preparation of 5-Hydroxy-Substituted Compounds

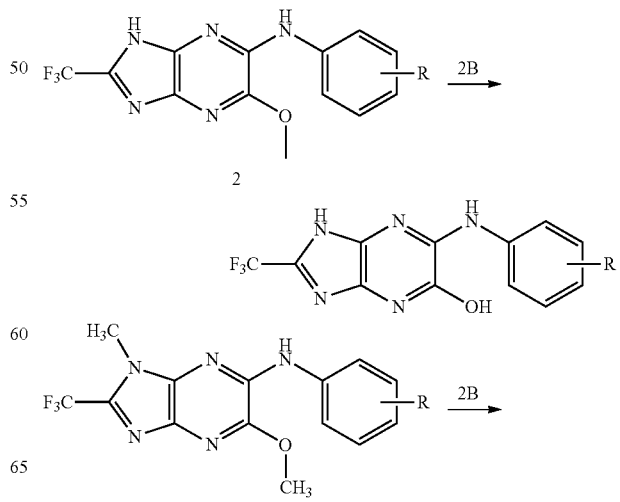

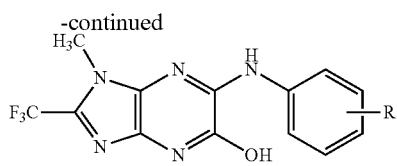

In a sealed tube, the desired methoxy substituted imidazole-pyrazine (0.05 mmol) and sodium iodide (0.15 mmol) were dissolved in glacial acetic acid (0.2 mL) and 48% Hydrobromic acid solution (1 mL); the mixture was stirred vigorously at 90° C. for 2 hours. After cooling to rt, the reaction mixture was quenched with a saturated NaHCO₃ aqueous solution and extracted with EtOAc three times. The organic layers were combined, washed with a saturated NaHCO₃ aqueous solution, dried over Na₂SO₄, and concentrated under reduced pressure. The residue was purified by silica gel column chromatography (10%-30% EtOAc/hexanes) to yield the desired 5-hydroxy-2-trifluoromethyl-N-phenyl-1H-imidazo[4,5-b]pyrazin-6-amine as a yellow solid.

General Procedure 2C. For Preparation of N-Methyl Compounds

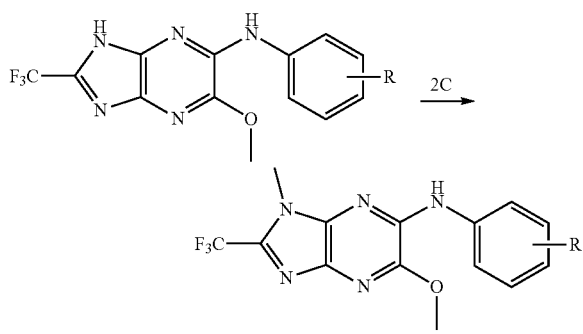

In a one dram vial, the requisite imidazole-pyrazine (1 equiv.) was dissolved in 2 mL of dichloromethane, followed by addition of methyl iodide (20 equiv.) and trimethylamine (1.5 equiv.), dropwise. The resulting mixture was stirred in the dark at room temperature. After 16 hours, the solvent was evaporated under reduced pressure, and purified by the silica gel column chromatography (0%-20% EtOAc/hexanes) to yield the desired 5-methoxy-1-methyl-N-phenyl-2-(trifluoromethyl)-1H-imidazo[4,5-b]pyrazin-6-amine as a yellow solid.

General Procedure 2D. Preparation of a 5-methoxy-2-substituted-N-phenyl-1H-imidazo[4,5-b]pyrazin-6-amine

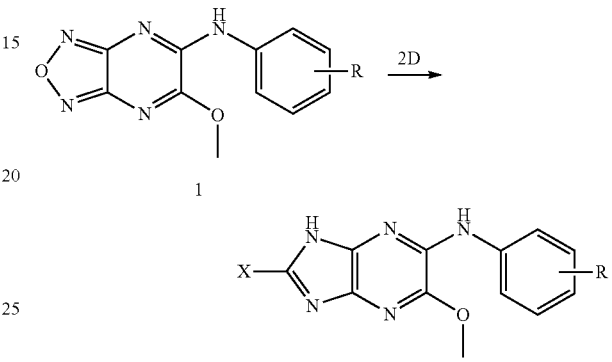

In a six dram vial, the desired oxadiazole-pyrazine 1 (1 mmol), iron (10 mmol), and ytterbium (III)triflate (0.1 mmol) were dissolved in glacial acetic acid (5.0 mL), followed by the addition of the desired orthoester (10 mmol). The mixture was vigorously stirred for 3 hours at 95° C. After cooling to rt, 20 mL H₂O and 20 mL EtOAc were added to the reaction mixture and it was filtered through a celite pad. The organic layer was separated, and the aqueous layer was extracted with EtOAc three times. The organic layers were combined, washed with a saturated NaHCO₃ aqueous solution, dried over Na₂SO₄, and concentrated under reduced pressure. The residue was purified by silica gel column chromatography to yield 5-methoxy-2-substituted-N-phenyl-1H-imidazo[4,5-b]pyrazin-6-amine as a light yellow solid.

Scheme 1, below, shows the relationship between General Procedures 2A, 2B, 2C, and 2D.

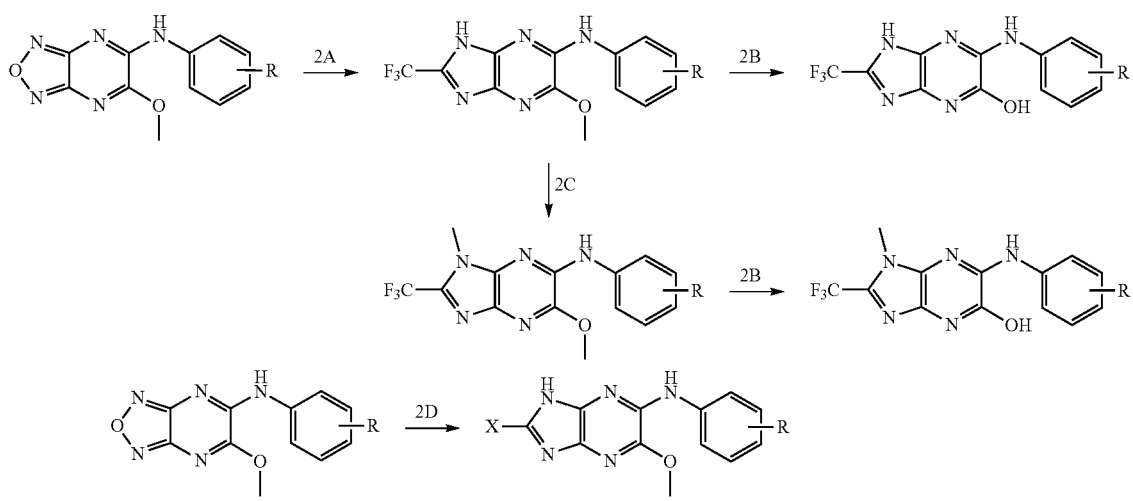

Examples 1-60, which follow, disclose compounds of Formula I-A and I-B. Some compounds of Example 1-60 are made using starting materials that are not commercially available. Procedures for making these starting materials follow in Example 61.

Example 1. Synthesis of 6-methoxy-N-(4-(trifluoromethoxy)phenyl)-2-(trifluoromethyl)-1H-imidazo[4,5-b]pyrazin-5-amine (2-1)

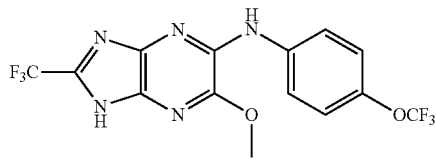 [SMILES: COc1nc2[nH]c(C(F)(F)F)nc2nc1Nc1ccc(OC(F)(F)F)cc1]

Compound 2-1 was synthesized by procedure 2A with 6-Methoxy-N-(4-(trifluoromethoxy) phenyl)-[1,2,5]oxadiazolo[3,4-b]pyrazin-5-amine (1-156) to yield 2-1 in 70% as a light yellow solid. $^1$H NMR (500 MHz, Acetone-$d_6$) δ 13.06 (brs, 1H), 8.65 (brs, 1H), 8.11 (d, 2H, J=9.1 Hz), 7.33 (d, 2H, J=8.6 Hz), 4.11 (s, 3H); $^{13}$C NMR (125 MHz, Acetone-$d_6$) δ 148.1, 143.6, 140.8, 139.2, 135.2 (d, J=40.7 Hz), 121.5, 120.7 (q, J=254.6 Hz), 120.6, 119.3 (q, J=268.4 Hz), 53.9; $^{19}$F NMR (376 MHz, Acetone-$d_6$) δ −58.88 (s, 3F), −64.41 (s, 3F); HRMS (ESI): Calc'd. for $C_{14}H_{10}F_6N_5C_2^+$ [M+H]$^+$: 394.0733, Observed: 394.0714.

Example 2. Synthesis of 6-methoxy-N-(4-(N-butyl)phenyl)-2-(trifluoromethyl)-1H-imidazo[4,5-b]pyrazin-5-amine (2-2)

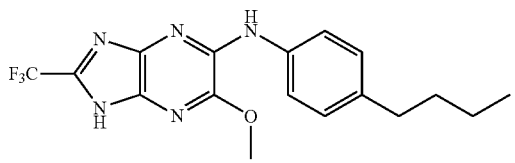 [SMILES: CCCCc1ccc(Nc2nc3nc(C(F)(F)F)[nH]c3nc2OC)cc1]

Compound 2-2 was synthesized by procedure 2A with N-(4-Butylphenyl)-6-methoxy-[1,2,5]oxadiazolo[3,4-b]pyrazin-5-amine (1-157) to yield 2-2 in 63% as a light yellow solid. $^1$H NMR (500 MHz, Acetone-$d_6$) δ 8.35 (brs, 1H), 7.86 (d, 2H, J=8.5 Hz), 7.20 (d, 2H, J=8.5 Hz), 4.10 (s, 3H), 2.61 (t, 2H, J=7.7 Hz), 1.62 (m, 2H), 1.38 (h, 2H, J=7.4 Hz), 0.94 (t, 3H, J=7.4 Hz); $^{13}$C NMR (125 MHz, Acetone-$d_6$) δ 148.0, 141.3, 137.6, 137.0, 134.6 (d, J=41.0 Hz), 128.4, 119.3 (q, J=268.2 Hz), 119.6, 53.8, 34.7, 33.8, 22.1, 13.3; $^{19}$F NMR (376 MHz, Acetone-$d_6$) δ −64.30 (s, 3F); HRMS (ESI): Calc'd. for $C_{17}H_{19}F_3N_5O^+$ [M+H]$^+$: 366.1536, Observed: 366.1531.

Example 3. Synthesis of 6-methoxy-N-(2-fluoro-5-(trifluoromethyl)phenyl)-2-(trifluoromethyl)-1H-imidazo[4,5-b]pyrazin-5-amine (2-3)

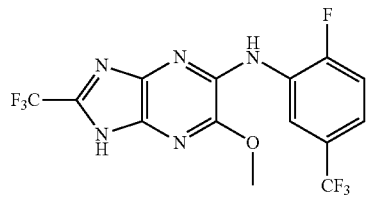 [SMILES: COc1nc2[nH]c(C(F)(F)F)nc2nc1Nc1cc(C(F)(F)F)ccc1F]

Compound 2-3 was synthesized by procedure 2A with N-(-Fluoro-5-(trifluoromethyl)phenyl)-6-methoxy-[1,2,5]oxadiazolo[3,4-b]pyrazin-5-amine (1-158) to yield 2-3 in 62% as a light yellow solid. $^1$H NMR (500 MHz, Acetone-$d_6$) δ 9.05 (d, 1H, J=7.0 Hz), 8.08 (brs, 1H), 7.51 (t, 1H, J=7.6 Hz), 7.49 (s, 1H) 4.19 (s, 3H); $^{13}$C NMR (125 MHz, Acetone-$d_6$) δ 154.9 (d, J=248.4 Hz), 148.2, 140.0, 136.1 (q, J=41.1 Hz), 128.8 (d, J=10.9 Hz), 126.3 (qd, J=32.6, 3.6 Hz), 124.2 (q, J=271.3 Hz), 120.1 (dd, J=8.4, 3.9 Hz), 119.2 (q, J=268.7 Hz), 117.7, 115.7 (d, J=21.1 Hz), 54.3; $^{19}$F NMR (376 MHz, Acetone-$d_6$) δ −62.49 (d, 3F, J=1.6 Hz), −64.56 (s, 3F), −125.47 (m, 1F); HRMS (ESI): Calc'd. for $C_{14}H_9F_7N_5O^+$ [M+H]$^+$: 396.0690, Observed: 396.0705.

Example 4. Synthesis of 6-methoxy-N-(3-(trifluoromethoxy)phenyl)-2-(trifluoromethyl)-1H-imidazo[4,5-b]pyrazin-5-amine (2-4)

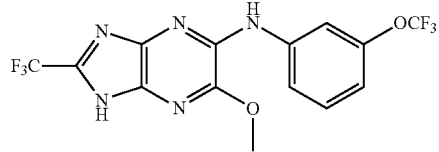 [SMILES: COc1nc2[nH]c(C(F)(F)F)nc2nc1Nc1cccc(OC(F)(F)F)c1]

Compound 2-4 was synthesized by procedure 2A using 6-Methoxy-N-(3-(trifluoromethoxy)phenyl)-[1,2,5]oxadiazolo[3,4-b]pyrazin-5-amine (1-141) to yield 2-4 in 38% as a light yellow solid. $^1$H NMR (500 MHz, Acetone-$d_6$) δ 13.06 (brs, 1H), 8.72 (brs, 1H), 8.22 (brs, 1H), 7.89 (d, 1H, J=8.2 Hz), 7.45 (t, 1H, J=8.2 Hz), 6.99 (d, 1H, J=8.2 Hz), 4.10 (s, 3H); $^{13}$C NMR (125 MHz, Acetone-$d_6$) δ 150.2 (q, J=1.7 Hz), 149.1, 142.7, 141.5, 136.3 (q, J=41.1 Hz), 130.8, 121.5 (q, J=255.4 Hz), 120.2 (q, J=268.6 Hz), 118.8, 114.9, 112.4, 54.9; $^{19}$F NMR (376 MHz, Acetone-$d_6$) δ −57.87 (s, 3F), −64.00 (s, 3F); HRMS (ESI): Calc'd. for $C_{14}H_9F_6N_5NaO_2^+$ [M+Na]$^+$: 416.0553, Observed: 416.0537.

Example 5. Synthesis of 6-methoxy-N-(2-methyl-5-(trifluoromethyl)phenyl)-2-(trifluoromethyl)-1H-imidazo[4,5-b]pyrazin-5-amine (2-5)

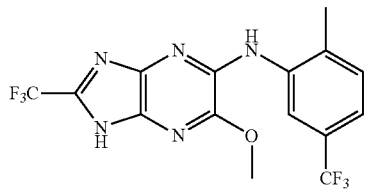 [SMILES: COc1nc2[nH]c(C(F)(F)F)nc2nc1Nc1cc(C(F)(F)F)ccc1C]

Compound 2-5 was synthesized by procedure 2A with 6-Methoxy-N-(2-methyl-5-(trifluoromethyl)phenyl)-[1,2,5]oxadiazolo[3,4-b]pyrazin-5-amine (1-142) to yield 2-5 in 58% as a light yellow solid. $^1$H NMR (500 MHz, Acetone-$d_6$) δ 12.97 (brs, 1H), 8.61 (brs, 1H), 7.91 (brs, 1H), 7.50 (d, 1H, J=7.9 Hz), 7.37 (d, 1H, J=7.9 Hz), 4.17 (s, 3H), 2.45 (s, 3H); $^{13}$C NMR (125 MHz, Acetone-$d_6$) δ 149.1, 142.1, 139.3, 136.2 (q, J=41.0 Hz), 134.6, 131.9, 129.1 (q, J=31.8 Hz), 125.4 (q, J=271.2 Hz), 120.7, 120.2 (q, J=268.5 Hz), 118.7, 55.1, 18.0; $^{19}$F NMR (376 MHz, Acetone-$d_6$) δ −62.71 (s, 3F), −64.45 (s, 3F); HRMS (ESI): Calc'd. for $C_{15}H_{12}F_6N_5O^+$ [M+H]$^+$: 392.0941, Observed: 392.0953.

Example 6. Synthesis of 6-methoxy-N-(2-fluoro-3-(trifluoromethyl)phenyl)-2-(trifluoromethyl)-1H-imidazo[4,5-b]pyrazin-5-amine (2-6)

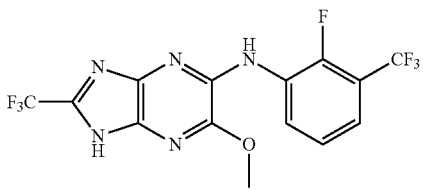 [SMILES: COc1nc2[nH]c(C(F)(F)F)nc2nc1Nc1cccc(C(F)(F)F)c1F]

Compound 2-6 was synthesized by procedure 2A with N-(2-Fluoro-3-(trifluoromethyl)phenyl)-6-methoxy-[1,2,5]oxadiazolo[3,4-b]pyrazin-5-amine (1-140) to yield 2-6 in 65% as a light yellow solid. $^1$H NMR (500 MHz, Acetone-$d_6$) δ 13.06 (brs, 1H), 8.78 (brs, 1H), 8.09 (brs, 1H), 7.45 (m, 2H), 4.17 (s, 3H); $^{13}$C NMR (125 MHz, Acetone-$d_6$) δ 151.5 (d, J=254.5 Hz), 149.1, 141.2, 136.9 (q, J=40.9 Hz), 130.0 (d, J=9.4 Hz), 126.8, 125.5 (d, J=4.6 Hz), 123.8 (q, J=271.5 Hz), 120.8, 120.1 (q, J=268.8 Hz), 118.5 (dd, J=32.8, 10.7 Hz), 55.2; $^{19}$F NMR (376 MHz, Acetone-$d_6$) δ −61.72 (d, 3F, J=12.9 Hz), −64.59 (s, 3F), −132.21 (s, 1F); HRMS (ESI): Calc'd. for $C_{14}H_8F_7N_5NaO^+$ [M+Na]$^+$: 418.0509, Observed: 418.0516.

Example 7. Synthesis of 6-methoxy-N-(3-fluorophenyl)-2-(trifluoromethyl)-1H-imidazo[4,5-b]pyrazin-5-amine (2-7)

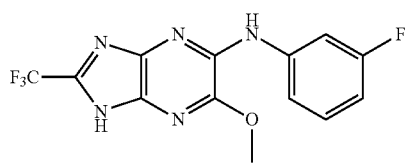 [SMILES: COc1nc2[nH]c(C(F)(F)F)nc2nc1Nc1cccc(F)c1]

Compound 2-7 was synthesized by procedure 2A with 1-143 to yield 2-7 in 55% as a light yellow solid. $^1$H NMR (500 MHz, Acetone-$d_6$) δ 13.00 (brs, 1H), 8.62 (brs, 1H), 8.08 (dt, 1H, J=12.2, 2.3 Hz), 7.63 (d, 1H, J=8.2 Hz), 7.35 (td, 1H, J=8.2, 6.8 Hz), 6.79 (td, 1H, J=8.2, 2.6 Hz), 4.09 (s, 3H); $^{13}$C NMR (125 MHz, Acetone-$d_6$) δ 163.9 (d, J=240.8 Hz), 149.0, 142.7 (d, J=11.4 Hz), 141.6, 136.2 (q, J=41.1 Hz), 130.8 (d, J=9.8 Hz), 120.2 (q, J=268.5 Hz), 116.0, 109.4 (d, J=21.6 Hz), 106.9 (d, J=27.2 Hz), 54.8; $^{19}$F NMR (376 MHz, Acetone-$d_6$) δ −64.46 (s, 3F), −113.8 (m, 1F); HRMS (ESI): Calc'd. for $C_{13}H_{10}F_4N_5O^+$ [M+H]$^+$: 328.0816, Observed: 328.0838.

Example 8. Synthesis of 6-methoxy-(3,5-bis(trifluoromethyl)phenyl)-2-(trifluoromethyl)-1H-imidazo[4,5-b]pyrazin-5-amine (2-8)

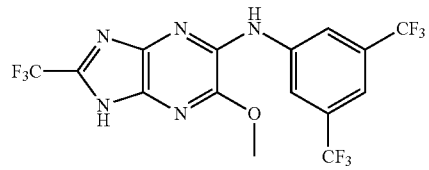

Compound 2-8 was synthesized by procedure 2A with N-(3,5-Bis(trifluoromethyl)phenyl)-6-methoxy-[1,2,5]oxadiazolo[3,4-b]pyrazin-5-amine (1-139) to yield 2-8 in 50% as a light yellow solid. $^1$H NMR (500 MHz, Acetone-$d_6$) δ 9.10 (brs, 1H), 8.74 (s, 2H), 7.64 (s, 1H), 4.13 (s, 3H); $^{13}$C NMR (125 MHz, Acetone-$d_6$) δ 149.2, 143.0, 141.0, 137.1 (q, J=40.9 Hz), 132.4 (q, J=32.8 Hz), 124.6 (q, J=271.9 Hz), 120.1 (q, J=268.7 Hz), 119.6, 115.4 (dt, J=7.4, 3.8 Hz), 55.0; $^{19}$F NMR (376 MHz, Acetone-$d_6$) δ −63.51 (s, 6F), −64.54 (s, 3F); HRMS (ESI): Calc'd. for $C_{15}H_9F_9N_5O^+$ [M+H]$^+$: 446.0658, Observed: 446.0680.

Example 9. Synthesis of 6-methoxy-(2-fluorophenyl)-2-(trifluoromethyl)-1H-imidazo[4,5-b]pyrazin-5-amine (2-9)

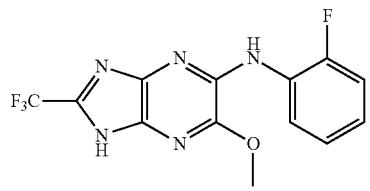 [SMILES: COc1nc2[nH]c(C(F)(F)F)nc2nc1Nc1ccccc1F]

Compound 2-9 was synthesized by procedure 2A with N-(2-Fluorophenyl)-6-methoxy-[1,2,5]oxadiazolo[3,4-b]pyrazin-5-amine (1-159) to yield 2-9 in 53% as a light yellow solid. $^1$H NMR (500 MHz, Acetone-$d_6$) δ 8.52 (t, 1H, J=8.2 Hz), 7.89 (brs, 1H), 7.24 (m, 2H), 7.11 (m, 1H), 4.16 (s, 3H); $^{13}$C NMR (125 MHz, Acetone-$d_6$) δ 153.5 (d, J=242.9 Hz), 148.1, 140.6, 135.4 (q, J=41.0 Hz), 127.7 (d, J=10.2 Hz), 127.7 (d, J=10.2 Hz), 124.7 (d, J=3.5 Hz), 124.4 (d, J=3.7 Hz), 123.4 (d, J=7.8 Hz), 121.5, 119.2 (q, J=268.5 Hz), 114.8 (d, J=19.5 Hz), 54.2; $^{19}$F NMR (376 MHz, Acetone-$d_6$) δ −64.47 (s, 3F), −130.86 (m, 1F); HRMS (ESI): Calc'd. for $C_{13}H_{10}F_4N_5O^+$ [M+H]$^+$: 328.0816, Observed: 328.0824.

Example 10. Synthesis of 6-methoxy-N-(p-tolyl)-2-(trifluoromethyl)-1H-imidazo[4,5-b]pyrazin-5-amine (2-10)

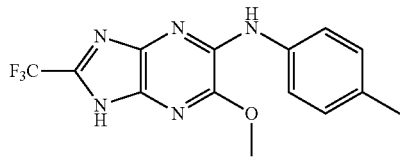 [SMILES: COc1nc2[nH]c(C(F)(F)F)nc2nc1Nc1ccc(C)cc1]

Compound 2-10 was synthesized by procedure 2A with 6-Methoxy-N-(p-tolyl)-[1,2,5]oxadiazolo[3,4-b]pyrazin-5-amine (1-144) to yield 2-10 in 49% as a light yellow solid. $^1$H NMR (500 MHz, Acetone-$d_6$) δ 8.31 (brs, 1H), 7.83 (d, 2H, J=8.1 Hz), 7.16 (d, 2H, J=8.1 Hz), 4.08 (s, 3H), 2.30 (s, 3H); $^{13}$C NMR (125 MHz, Acetone-$d_6$) δ 148.9, 142.2, 138.3, 135.5 (d, J=40.7 Hz), 132.7, 129.9, 120.5, 120.2 (q, J=268.3 Hz), 54.7, 20.8; $^{19}$F NMR (376 MHz, Acetone-$d_6$) δ −64.30 (s, 3F); HRMS (ESI): Calc'd. for $C_{14}H_{13}F_3N_5O^+$ [M+H]$^+$: 324.1067, Observed: 324.1079.

Example 11. Synthesis of 6-methoxy-N-phenyl-2-(trifluoromethyl)-1H-imidazo[4,5-b]pyrazin-5-amine (2-11)

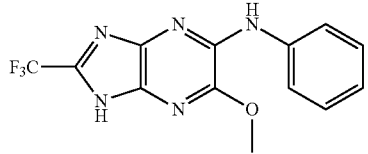 [SMILES: COc1nc2[nH]c(C(F)(F)F)nc2nc1Nc1ccccc1]

Compound 2-11 was synthesized by procedure 2A with 6-Methoxy-N-phenyl-[1,2,5]oxadiazolo[3,4-b]pyrazin-5-amine (1-146) to yield 2-11 in 56% as a light yellow solid. $^1$H NMR (500 MHz, Acetone-$d_6$) δ 8.39 (brs, 1H), 7.96 (d, 2H, J=7.9 Hz), 7.34 (t, 2H, J=7.9 Hz), 7.04 (t, 1H, J=7.4 Hz), 4.09 (s, 3H); $^{13}$C NMR (125 MHz, Acetone-$d_6$) δ 149.0, 142.0, 140.8, 135.7 (d, J=41.1 Hz), 129.4, 123.3, 120.4, 120.2 (q, J=268.4 Hz), 54.8; $^{19}$F NMR (376 MHz, Acetone-$d_6$) δ −64.36 (s, 3F); HRMS (ESI): Calc'd. for $C_{13}H_{11}F_3N_6O^+$ [M+H]$^+$: 310.0910, Observed: 310.0918.

Example 12. Synthesis of 6-methoxy-N-(4-methoxyphenyl)-2-(trifluoromethyl)-1H-imidazo[4,5-b]pyrazin-5-amine (2-12)

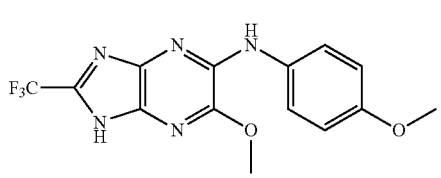 [SMILES: COc1ccc(Nc2nc3nc(C(F)(F)F)[nH]c3nc2OC)cc1]

Compound 2-12 was synthesized by procedure 2A with 6-Methoxy-N-(4-methoxyphenyl)-[1,2,5]oxadiazolo[3,4-b]pyrazin-5-amine (1-145) to yield 2-12 in 45% as a light yellow solid. $^1$H NMR (500 MHz, Acetone-$d_6$) δ 7.84 (brs, 1H), 7.83 (d, 2H, J=9.1 Hz), 6.93 (d, 2H, J=9.1 Hz), 4.08 (s, 3H); 3.80 (s, 3H); $^{13}$C NMR (125 MHz, Acetone-$d_6$) δ 155.6, 148.0, 141.5, 134.2 (d, J=41.3 Hz), 132.8, 121.5, 119.4 (q, J=268.2 Hz), 113.7, 54.8, 53.8; $^{19}$F NMR (376 MHz, Acetone-$d_6$) δ −64.26 (s, 3F); HRMS (ESI): Calc'd. for $C_{14}H_{12}F_3N_5O_2^+$[M+H]$^+$: 340.1016, Observed: 340.1032.

Example 13. Synthesis of 6-methoxy-N-(3-fluoro-4-(trifluoromethoxy)phenyl)-2-(trifluoromethyl)-1H-imidazo[4,5-b]pyrazin-5-amine (2-13)

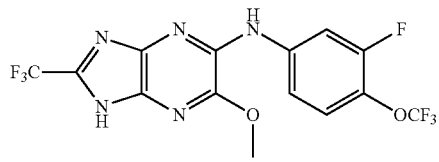 [SMILES: COc1nc2[nH]c(C(F)(F)F)nc2nc1Nc1ccc(OC(F)(F)F)c(F)c1]

Compound 2-13 was synthesized by procedure 2A with N-(3-Fluoro-4-(trifluoromethoxy)phenyl)-6-methoxy-[1,2,5]oxadiazolo[3,4-b]pyrazin-5-amine (1-151) to yield 2-13 in 63% as a light yellow solid. $^1$H NMR (500 MHz, Acetone-$d_6$) δ 8.81 (brs, 1H), 8.33 (dd, 1H, J=13.5, 2.6 Hz), 7.74 (ddd, 1H, J=9.0, 2.6, 1.5 Hz), 7.44 (td, 1H, J=9.0, 1.5 Hz), 4.10 (s, 3H); $^{13}$C NMR (125 MHz, Acetone-$d_6$) δ 155.1 (d, J=246.8 Hz), 149.1, 141.7 (d, J=10.4 Hz), 141.2, 136.7 (q, J=40.7 Hz), 130.8 (d, J=12.6 Hz), 124.9, 121.6 (q, J=256.3 Hz), 120.2 (q, J=268.6 Hz), 116.3 (d, J=3.3 Hz), 108.3 (d, J=24.3 Hz), 54.9; $^{19}$F NMR (376 MHz, Acetone-$d_6$) δ −60.04 (dd, 3F, J=14.2, 5.1 Hz), −64.51 (s, 3F), −129.63 (m, 1F); HRMS (ESI): Calc'd. for $C_{14}H_9F_7N_5O_2^+$ [M+H]$^+$: 412.0639, Observed: 412.0652.

Example 14. Synthesis of 6-methoxy-N-(2-fluoro-4-(trifluoromethyl)phenyl)-2-(trifluoromethyl)-1H-imidazo[4,5-b]pyrazin-5-amine (2-14)

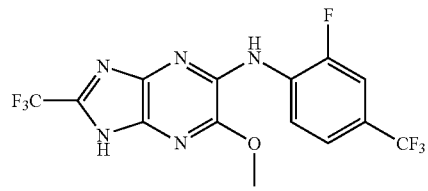 [SMILES: COc1nc2[nH]c(C(F)(F)F)nc2nc1Nc1ccc(C(F)(F)F)cc1F]

Compound 2-14 was synthesized by procedure 2A with N-(2-fluoro-4-(trifluoromethyl)phenyl)-6-methoxy-[1,2,5]oxadiazolo[3,4-b]pyrazin-5-amine (1-202) to yield 2-14 in 53% as a light yellow solid. $^1$H NMR (500 MHz, Acetone-$d_6$) δ 8.87 (t, 1H, J=8.4 Hz), 8.06 (brs, 1H), 7.60 (m, 2H), 4.17 (s, 3H); $^{13}$C NMR (125 MHz, Acetone-$d_6$) δ 153.1 (d, J=244.9 Hz), 149.2, 140.5, 137.3 (q, J=41.0 Hz), 132.5 (d, J=9.6 Hz), 131.0 (d, J=10.8 Hz), 124.8 (qd, J=270.6, 2.6 Hz), 124.5 (qd, J=33.2, 7.3 Hz), 122.7 (p, J=4.0 Hz), 121.2, 120.1 (q, J=268.8 Hz), 113.2 (dq, J=23.0, 3.8 Hz), 55.2; $^{19}$F NMR (376 MHz, Acetone-$d_6$) δ −62.35 (s, 3F), −64.62 (s, 3F), −129.81 (m, 1F); HRMS (ESI): Calc'd. for $C_{14}H_9F_7N_5O^+$[M+H]$^+$: 396.0690, Observed: 396.0704.

Example 15. Synthesis of 6-methoxy-N-(3,5-difluorophenyl)-2-(trifluoromethyl)-1H-imidazo[4,5-b]pyrazin-5-amine (2-15)

Compound 2-15 was synthesized by procedure 2A with N-(2,3-Difluorophenyl)-6-methoxy-[1,2,5]oxadiazolo[3,4-b]pyrazin-5-amine (1-147) to yield 2-15 in 60% as a light yellow solid. $^1$H NMR (500 MHz, Acetone-$d_6$) δ 8.80 (brs, 1H), 7.76 (dd, 2H, J=10.3, 2.3 Hz), 6.65 (tt, 1H, J=10.3, 2.3 Hz), 4.09 (s, 3H); $^{13}$C NMR (125 MHz, Acetone-$d_6$) δ 164.1 (d, J=242.3 Hz), 164.0 (d, J=242.3 Hz), 149.0, 143.6 (t, J=14.0 Hz), 141.4, 136.8 (q, J=41.3 Hz), 120.1 (q, J=268.7 Hz), 102.7 (dd, J=30.3, 15.0 Hz), 97.6 (d, J=26.3 Hz), 54.9; $^{19}$F NMR (376 MHz, Acetone-$d_6$) δ −64.53 (s, 3F), −111.35 (t, 2F, J=9.6 Hz); HRMS (ESI): Calc'd. for $C_{13}H_9F_5N_5O^+$ [M+H]$^+$: 346.0722, Observed: 346.0723.

Example 16. Synthesis of 6-methoxy-N-(2,3-difluorophenyl)-2-(trifluoromethyl)-1H-imidazo[4,5-b]pyrazin-5-amine (2-16)

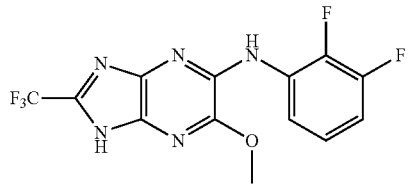 [SMILES: COc1nc2[nH]c(C(F)(F)F)nc2nc1Nc1cccc(F)c1F]

Compound 2-16 was synthesized by procedure 2A with N-(3,5-Difluorophenyl)-6-methoxy-[1,2,5]oxadiazolo[3,4-b]pyrazin-5-amine (1-148) to yield 2-16 in 62% as a light yellow solid. $^1$H NMR (500 MHz, Acetone-$d_6$) δ 8.24 (ddt, 1H, J=8.5, 6.9, 1.6 Hz), 8.01 (brs, 1H), 7.21 (tdd, 1H, J=8.3, 5.8, 2.1 Hz), 7.05 (dddd, 1H, J=10.1, 8.7, 7.5, 1.5 Hz), 4.15 (s, 3H); $^{13}$C NMR (125 MHz, Acetone-$d_6$) δ 151.4 (d, J=244.2 Hz), 151.3 (d, J=244.2 Hz), 149.0, 143.2 (d, J=244.9 Hz), 143.1 (d, J=244.9 Hz), 141.3, 136.8 (q, J=41.0 Hz), 130.5 (dd, J=7.6, 2.1 Hz), 125.0 (d, J=8.2, 4.9 Hz), 120.1 (q, J=268.5 Hz), 118.1, 111.8 (d, J=17.2 Hz), 55.1; $^{19}$F NMR (376 MHz, Acetone-$d_6$) δ −64.35 (s, 3F), −140.58 (m, 1F), −154.27 (m, 1F); HRMS (ESI): Calc'd. for $C_{13}H_9F_5N_5O^+$ [M+H]$^+$: 346.0722, Observed: 346.0717.

Example 17. Synthesis of 6-methoxy-N-(2-fluorophenyl)-2-(trifluoromethyl)-1H-imidazo[4,5-b]pyrazin-5-amine (2-17)

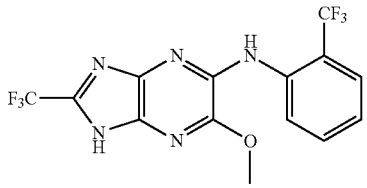 [SMILES: COc1nc2[nH]c(C(F)(F)F)nc2nc1Nc1ccccc1C(F)(F)F]

Compound 2-17 was synthesized by procedure 2A with 6-Methoxy-N-(2-(trifluoromethyl)phenyl)-[1,2,5]oxadiazolo[3,4-b]pyrazin-5-amine (1-160) to yield 2-17 in 40% as a light yellow solid. $^1$H NMR (500 MHz, Acetone-$d_6$) δ 8.60 (d, 2H, J=8.3 Hz), 7.97 (brs, 1H), 7.75 (d, 2H, J=7.9 Hz), 7.71 (t, 2H, J=7.9 Hz), 7.32 (t, 1H, J=7.6 Hz), 4.18 (s, 3H); $^{13}$C NMR (125 MHz, Acetone-$d_6$) δ 149.0, 141.5, 138.1 (d, J=1.6 Hz), 136.8 (q, J=40.9 Hz), 133.9. 127.2 (q, J=5.5 Hz), 125.5 (q, J=272.2 Hz), 124.3, 120.7 (q, J=29.3 Hz), 120.1 (q, J=268.6 Hz), 55.3; $^{19}$F NMR (376 MHz, Acetone-$d_6$) δ −61.55 (s, 3F), −64.56 (s, 3F); HRMS (ESI): Calc'd. for $C_{14}H_9F_6N_5O^+$ [M+H]$^+$: 378.0784, Observed: 378.0791.

Example 18. Synthesis of N-([1,1'-biphenyl]-4-yl)-6-methoxy-2-(trifluoromethyl)-1H-imidazo[4,5-b]pyrazin-5-amine (2-18)

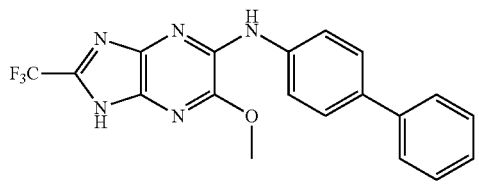 [SMILES: COc1nc2[nH]c(C(F)(F)F)nc2nc1Nc1ccc(-c2ccccc2)cc1]

Compound 2-18 was synthesized by procedure 2A with N-([1,1'-Biphenyl]-4-yl)-6-methoxy-[1,2,5]oxadiazolo[3,4-b]pyrazin-5-amine (1-161) to yield 2-18 in 50% as a light yellow solid. $^1$H NMR (500 MHz, Acetone-$d_6$) δ 8.53 (brs, 1H), 8.08 (d, 2H, J=8.7 Hz), 7.66 (m, 4H), 7.45 (t, 2H, J=7.7 Hz), 7.32 (t, 1H, J=7.6 Hz), 4.11 (s, 3H); $^{13}$C NMR (125 MHz, Acetone-$d_6$) δ 149.1, 141.9, 141.5, 140.3, 135.9 (d, J=40.9 Hz), 135.8, 129.7, 127.9, 127.7, 127.3, 120.7, 120.2 (q, J=268.4 Hz), 54.8; $^{19}$F NMR (376 MHz, Acetone-$d_6$) δ −64.33 (s, 3F); HRMS (ESI): Calc'd. for $C_{19}H_{15}F_3N_5O^+$ [M+H]$^+$: 386.1223, Observed: 386.1222.

Example 19. Synthesis of 6-methoxy-N-(4-(tert-butyl)phenyl)-2-(trifluoromethyl)-1H-imidazo[4,5-b]pyrazin-5-amine (2-19)

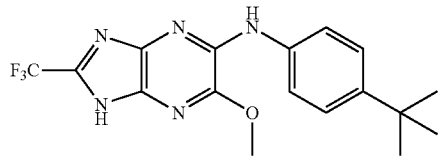 [SMILES: COc1nc2[nH]c(C(F)(F)F)nc2nc1Nc1ccc(C(C)(C)C)cc1]

Compound 2-19 was synthesized by procedure 2A with N-(4-(tert-Butyl)phenyl)-6-methoxy-[1,2,5]oxadiazolo[3,4-b]pyrazin-5-amine (1-162) to yield 2-19 in 45% as a light yellow solid. $^1$H NMR (500 MHz, Acetone-d$_6$) δ 8.34 (brs, 1H), 7.86 (d, 2H, J=8.8 Hz), 7.39 (d, 2H, J=8.8 Hz), 4.09 (s, 3H), 1.32 (s, 9H); $^{13}$C NMR (125 MHz, Acetone-d$_6$) δ 148.9, 146.1, 142.2, 138.2, 135.6 (d, J=40.4 Hz), 126.2, 120.4, 120.3 (q, J=268.3 Hz), 54.7, 34.8, 31.7; $^{19}$F NMR (376 MHz, Acetone-d$_6$) δ −64.29 (s, 3F); HRMS (ESI): Calc'd. for C$_{17}$H$_{19}$F$_3$N$_5$O$^+$ [M+H]$^+$: 366.1536, Observed: 366.1541.

Example 20. Synthesis of 6-methoxy-N-(naphthalen-2-yl)-2-(trifluoromethyl)-1H-imidazo[4,5-b]pyrazin-5-amine (2-20)

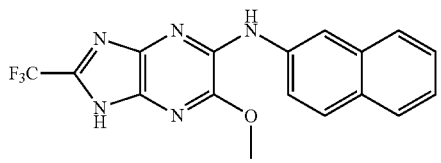 [SMILES: COc1nc2[nH]c(C(F)(F)F)nc2nc1Nc1ccc2ccccc2c1]

Compound 2-20 was synthesized by procedure 2A with 6-Methoxy-N-(naphthalen-2-yl)-[1,2,5]oxadiazolo[3,4-b]pyrazin-5-amine (1-152) to yield 2-20 in 40% as a light yellow solid. $^1$H NMR (500 MHz, Acetone-d$_6$) δ 8.74 (brs, 1H), 8.59 (brs, 1H), 7.87 (m, 2H), 7.82 (dd, 2H, J=12.7, 8.2 Hz), 7.47 (ddd, 1H, J=8.1, 6.8, 1.3 Hz), 7.38 (ddd, 1H, J=8.1, 6.8, 1.3 Hz), 4.12 (s, 3H); $^{13}$C NMR (125 MHz, Acetone-d$_6$) δ 149.1, 141.9, 138.4, 136.0 (d, J=41.1 Hz), 135.1, 130.9, 129.1, 128.4, 128.1, 127.2, 125.1, 121.7, 120.3 (q, J=268.5 Hz), 115.7, 54.8; $^{19}$F NMR (376 MHz, Acetone-d$_6$) δ −64.30 (s, 3F); HRMS (ESI): Calc'd. for C$_{17}$H$_{13}$F$_3$N$_5$O$^+$ [M+H]$^+$: 360.1067, Observed: 360.1074.

Example 21. Synthesis of 6-methoxy-N-(2-fluoro-4-(trifluoromethoxy)phenyl)-2-(trifluoromethyl)-1H-imidazo[4,5-b]pyrazin-5-amine (2-21)

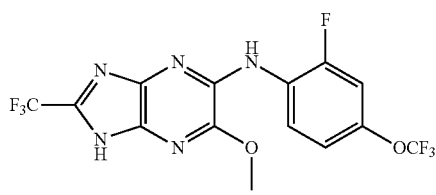 [SMILES: COc1nc2[nH]c(C(F)(F)F)nc2nc1Nc1ccc(OC(F)(F)F)cc1F]

Compound 2-21 was synthesized by procedure 2A with N-(2-Fluoro-4-(trifluoromethoxy)phenyl)-6-methoxy-[1,2,5]oxadiazolo[3,4-b]pyrazin-5-amine (1-163) to yield 2-21 in 62% as a light yellow solid. $^1$H NMR (500 MHz, Acetone-d$_6$) δ 8.59 (t, 1H, J=9.1 Hz), 7.98 (brs, 1H), 7.34 (dd, 1H, J=11.3, 2.7 Hz), 7.26 (d, 1H, J=9.1 Hz), 4.16 (s, 3H); $^{13}$C NMR (125 MHz, Acetone-d$_6$) δ 154.2 (d, J=246.9 Hz), 149.0, 144.5 (d, J=10.7 Hz), 141.3, 136.8 (q, J=40.9 Hz), 128.1 (d, J=10.4 Hz), 123.3, 121.4 (q, J=255.8 Hz), 120.1 (q, J=268.7 Hz), 118.1 (q, J=3.6 Hz), 110.2 (d, J=23.6 Hz), 55.1; $^{19}$F NMR (376 MHz, Acetone-d$_6$) δ −59.10 (s, 3F), −64.55 (s, 3F), −125.5 (m, 1F); HRMS (ESI): Calc'd. for C$_{14}$H$_9$F$_7$N$_5$O$_2$$^+$ [M+H]$^+$: 412.0639, Observed: 412.0646.

Example 22. Synthesis of 6-methoxy-N-(4-(trifluoromethyl)phenyl)-2-(trifluoromethyl)-1H-imidazo[4,5-b]pyrazin-5-amine (2-22)

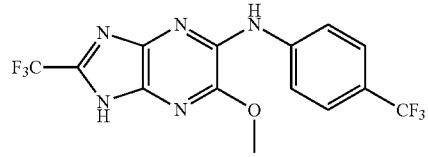 [SMILES: COc1nc2[nH]c(C(F)(F)F)nc2nc1Nc1ccc(C(F)(F)F)cc1]

Compound 2-22 was synthesized by procedure 2A with 6-Methoxy-N-(4-(trifluoromethyl)phenyl)-[1,2,5]oxadiazolo[3,4-b]pyrazin-5-amine (1-165) to yield 2-22 in 70% as a light yellow solid. $^1$H NMR (500 MHz, Acetone-d$_6$) δ 8.77 (brs, 1H), 8.21 (d, 2H, J=8.7 Hz), 7.67 (d, 2H, J=8.7 Hz), 4.10 (s, 3H); $^{13}$C NMR (125 MHz, Acetone-d$_6$) δ 149.2, 144.5, 141.2, 136.7 (q, J=40.9 Hz), 126.7 (q, J=3.7 Hz), 125.3 (q, J=271.8 Hz), 123.9 (q, J=32.4 Hz), 120.2 (q, J=268.6 Hz), 119.8, 54.9; $^{19}$F NMR (376 MHz, Acetone-d$_6$) δ −62.17 (s, 3F), −64.50 (s, 3F); HRMS (ESI): Calc'd. for C$_{14}$H$_{10}$F$_6$N$_5$O$^+$ [M+H]$^+$: 378.0784, Observed: 378.0789.

Example 23. Synthesis of 6-methoxy-N-(3-fluoro-4-(trifluoromethyl)phenyl)-2-(trifluoromethyl)-1H-imidazo[4,5-b]pyrazin-5-amine (2-23)

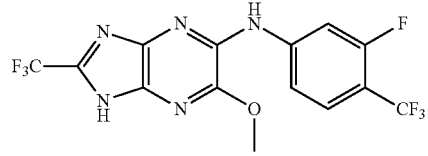 [SMILES: COc1nc2[nH]c(C(F)(F)F)nc2nc1Nc1ccc(C(F)(F)F)c(F)c1]

Compound 2-23 was synthesized by procedure 2A with N-(3-Fluoro-4-(trifluoromethyl)phenyl)-6-methoxy-[1,2,5] oxadiazolo[3,4-b]pyrazin-5-amine (1-178) to yield 2-23 in 63% as a light yellow solid. $^1$H NMR (500 MHz, Acetone-d$_6$) δ 8.99 (brs, 1H), 8.34 (dd, 1H, J=14.2, 2.0 Hz), 7.82 (d, 1H, J=8.6 Hz), 7.66 (t, 1H, J=8.6 Hz), 4.10 (s, 3H); $^{13}$C NMR (125 MHz, Acetone-d$_6$) δ 160.9 (d, J=250.4 Hz), 149.2, 146.7 (d, J=11.7 Hz), 140.7, 137.3 (q, J=40.9 Hz), 128.1, 124.2 (q, J=270.9 Hz), 120.1 (q, J=268.7 Hz), 115.3, 110.9 (d, J=32.9, 12.8 Hz), 107.1 (d, J=26.4 Hz), 55.0; $^{19}$F NMR (376 MHz, Acetone-d$_6$) δ −60.78 (d, 3F, J=12.2 Hz), −64.58 (s, 3F), −115.26 (m, 1F); HRMS (ESI): Calc'd. for C$_{28}$H$_{17}$F$_{14}$N$_{10}$O$_2$$^+$ [2M+H]$^+$: 791.1307, Observed: 791.1286.

Example 24. Synthesis of 6-methoxy-N-(4-ethylphenyl)-2-(trifluoromethyl)-1H-imidazo[4,5-b]pyrazin-5-amine (2-24)

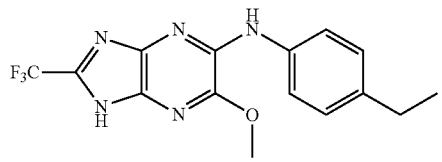 [SMILES: CCc1ccc(Nc2nc3nc(C(F)(F)F)[nH]c3nc2OC)cc1]

Compound 2-24 was synthesized by procedure 2A with N-(4-Ethylphenyl)-6-methoxy-[1,2,5]oxadiazolo[3,4-b]pyrazin-5-amine (1-153) to yield 2-24 in 58% as a light yellow solid. $^1$H NMR (500 MHz, Acetone-d$_6$) δ 8.33 (brs, 1H), 7.85 (d, 2H, J=8.5 Hz), 7.19 (d, 2H, J=8.5 Hz), 4.09 (s, 3H), 2.62 (q, 2H, J=7.6 Hz), 1.21 (t, 3H, J=7.6 Hz); $^{13}$C NMR (125 MHz, Acetone-d$_6$) δ 148.9, 142.2, 139.3, 138.5, 135.6 (d, J=40.7 Hz), 133.0, 128.7, 120.5, 120.3 (q, J=268.3 Hz), 54.7, 28.9, 16.3; $^{19}$F NMR (376 MHz, Acetone-d$_6$) δ −64.31 (s, 3F); HRMS (ESI): Calc'd. for $C_{15}H_{15}F_3N_5O^+$ [M+H]$^+$: 338.1223, Observed: 338.1225.

Example 25. Synthesis of 6-methoxy-N-(4-isopropylphenyl)-2-(trifluoromethyl)-1H-imidazo[4,5-b]pyrazin-5-amine (2-25)

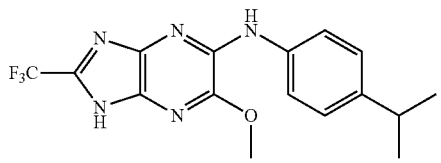 [SMILES: COc1nc2[nH]c(C(F)(F)F)nc2nc1Nc1ccc(C(C)C)cc1]

Compound 2-25 was synthesized by procedure 2A with N-(4-Isopropylphenyl)-6-methoxy-[1,2,5]oxadiazolo[3,4-b]pyrazin-5-amine (1-164) to yield 2-25 in 60% as a light yellow solid. $^1$H NMR (500 MHz, Acetone-d$_6$) δ 8.40 (brs, 1H), 7.87 (d, 2H, J=8.5 Hz), 7.23 (d, 2H, J=8.5 Hz), 4.08 (s, 3H), 2.90 (h, 1H, J=7.0 Hz), 1.24 (t, 6H, J=7.0 Hz); $^{13}$C NMR (125 MHz, Acetone-d$_6$) δ 148.9, 143.9, 142.2, 138.5, 135.4 (d, J=41.3 Hz), 127.2, 123.4, 120.6, 120.2 (q, J=268.3 Hz), 54.7, 34.2, 24.4; $^{19}$F NMR (376 MHz, Acetone-d$_6$) δ −64.31 (s, 3F); HRMS (ESI): Calc'd. for $C_{16}H_{17}F_3N_5O^+$ [M+H]$^+$: 352.1380, Observed: 352.1380.

Example 26. Synthesis of 6-methoxy-N-(4-chlorophenyl)-2-(trifluoromethyl)-1H-imidazo[4,5-b]pyrazin-5-amine (2-26)

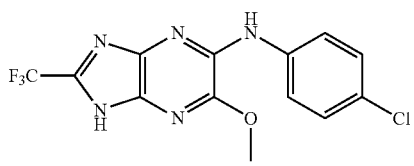 [SMILES: COc1nc2[nH]c(C(F)(F)F)nc2nc1Nc1ccc(Cl)cc1]

Compound 2-26 was synthesized by procedure 2A with N-(4-Chlorophenyl)-6-methoxy-[1,2,5]oxadiazolo[3,4-b]pyrazin-5-amine (1-149) to yield 2-26 in 53% as a light yellow solid. $^1$H NMR (500 MHz, Acetone-d$_6$) δ 8.55 (brs, 1H), 8.01 (d, 2H, J=9.0 Hz), 7.35 (d, 2H, J=9.0 Hz), 4.09 (s, 3H); $^{13}$C NMR (125 MHz, Acetone-d$_6$) δ 149.0, 141.7, 139.8, 136.1 (q, J=41.0 Hz), 129.3, 127.4, 123.4, 121.7, 120.2 (q, J=268.4 Hz), 54.8; $^{19}$F NMR (376 MHz, Acetone-d$_6$) δ −64.37 (s, 3F); HRMS (ESI): Calc'd. for $C_{13}H_{10}ClF_3N_5O^+$ [M+H]$^+$: 352.0520, Observed: 344.0519.

Example 27. Synthesis of 6-methoxy-N-(2-fluoro-4-pentylphenyl)-2-(trifluoromethyl)-1H-imidazo[4,5-b]pyrazin-5-amine (2-27)

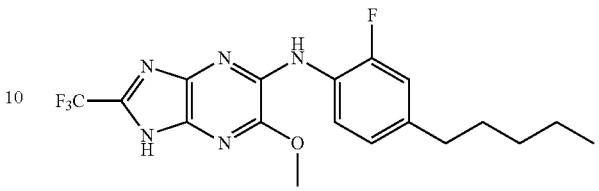

Compound 2-27 was synthesized by procedure 2A with N-(2-Fluoro-4-pentylphenyl)-6-methoxy-[1,2,5]oxadiazolo[3,4-b]pyrazin-5-amine (1-155) to yield 2-27 in 56% as a light yellow solid. $^1$H NMR (500 MHz, Acetone-d$_6$) δ 8.34 (t, 1H, J=8.4 Hz), 7.82 (brs, 1H), 7.07 (m, 2H), 4.16 (s, 3H), 2.62 (t, 2H, J=7.7 Hz), 1.64 (m, 2H), 1.34 (m, 4H), 0.90 (t, 3H, J=7.0 Hz); $^{13}$C NMR (125 MHz, Acetone-d$_6$) δ 154.5 (d, J=242.9 Hz), 148.9, 141.8, 140.0 (d, J=6.6 Hz), 136.1 (q, J=41.0 Hz), 126.0 (d, J=10.6 Hz), 124.9 (d, J=3.1 Hz), 122.7, 120.2 (q, J=268.5 Hz), 115.6 (d, J=19.1 Hz), 55.0, 35.7, 32.1, 31.9, 23.2, 14.3; $^{19}$F NMR (376 MHz, Acetone-d$_6$) δ −64.44 (s, 3F), −130.75 (m, 1F); HRMS (ESI): Calc'd. for $C_{36}H_{39}F_8N_{10}C_2^+$ [2M+H]$^+$: 795.3124, Observed: 795.3098.

Example 28. Synthesis of 6-methoxy-N-(3-fluoro-4-pentylphenyl)-2-(trifluoromethyl)-1H-imidazo[4,5-b]pyrazin-5-amine (2-28)

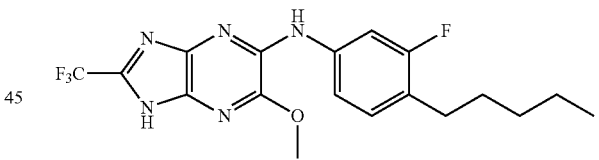

Compound 2-28 was synthesized by procedure 2A with N-(3-Fluoro-4-pentylphenyl)-6-methoxy-[1,2,5]oxadiazolo[3,4-b]pyrazin-5-amine (1-154) to yield 2-28 in 58% as a light yellow solid. $^1$H NMR (500 MHz, Acetone-d$_6$) δ 8.53 (brs, 1H), 8.01 (dd, 1H, J=13.0, 2.2 Hz), 7.54 (dd, 1H, J=8.3, 2.2 Hz), 7.21 (t, 1H, J=8.3 Hz), 4.09 (s, 3H), 2.62 (t, 2H, J=7.7 Hz), 1.62 (m, 2H), 1.35 (m, 4H), 0.90 (t, 3H, J=7.0 Hz); $^{13}$C NMR (125 MHz, Acetone-d$_6$) δ 161.7 (d, J=240.3 Hz), 148.9, 141.7, 140.3 (d, J=11.5 Hz), 136.1 (q, J=41.0 Hz), 131.3 (d, J=6.8 Hz), 123.7 (d, J=16.8 Hz), 120.2 (q, J=268.4 Hz), 116.0, 107.0 (d, J=28.5 Hz), 54.8, 32.1, 30.9, 23.1, 14.3; $^{19}$F NMR (376 MHz, Acetone-d$_6$) δ −64.39 (s, 3F), −119.31 (m, 1F); HRMS (ESI): Calc'd. for $C_{18}H_{20}F_4N_5O^+$ [M+H]$^+$: 398.1598, Observed: 398.1594.

Example 29. Synthesis of 6-methoxy-N-(4-pentylphenyl)-2-(trifluoromethyl)-1H-imidazo[4,5-b]pyrazin-5-amine (2-29)

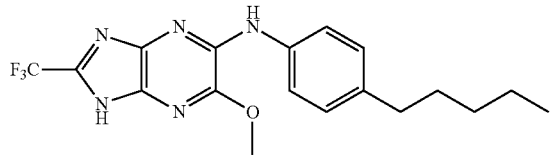 [SMILES: CCCCCc1ccc(Nc2nc3nc(C(F)(F)F)[nH]c3nc2OC)cc1]

Compound 2-29 was synthesized by procedure 2A with 6-Methoxy-N-(4-pentylphenyl)-[1,2,5]oxadiazolo[3,4-b]pyrazin-5-amine (1-167) to yield 2-29 in 51% as a light yellow solid. $^1$H NMR (500 MHz, Acetone-$d_6$) δ 8.32 (brs, 1H), 7.85 (d, 1H, J=8.5 Hz), 7.18 (d, 1H, J=8.5 Hz), 4.09 (s, 3H), 2.59 (t, 2H, J=7.7 Hz), 1.62 (m, 2H), 1.34 (m, 4H), 0.89 (t, 3H, J=7.0 Hz); $^{13}$C NMR (125 MHz, Acetone-$d_6$) δ 148.9, 142.2, 138.4, 137.9, 135.5 (q, J=41.1 Hz), 129.3, 120.5, 120.3 (q, J=268.3 Hz), 54.7, 35.9, 32.2, 23.2, 14.3; $^{19}$F NMR (376 MHz, Acetone-$d_6$) δ −64.29 (s, 3F); HRMS (ESI): Calc'd. for $C_{36}H_{41}F_6N_{10}O_2^+$ [2M+H]$^+$: 759.3313, Observed: 759.3290.

Example 30. Synthesis of 6-methoxy-N-(4-iodophenyl)-2-(trifluoromethyl)-1H-imidazo[4,5-b]pyrazin-5-amine (2-30)

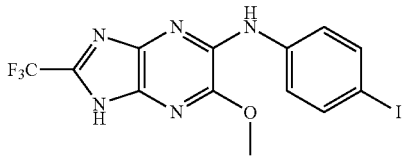 [SMILES: COc1nc2[nH]c(C(F)(F)F)nc2nc1Nc1ccc(I)cc1]

Compound 2-30 was synthesized by procedure 2A with N-(4-Iodophenyl)-6-methoxy-[1,2,5]oxadiazolo[3,4-b]pyrazin-5-amine (1-169) to yield 2-30 in 54% as a light yellow solid. $^1$H NMR (500 MHz, Acetone-$d_6$) δ 8.58 (brs, 1H), 7.86 (d, 2H, J=8.9 Hz), 7.67 (d, 2H, J=8.9 Hz), 4.08 (s, 3H); $^{13}$C NMR (125 MHz, Acetone-$d_6$) δ 149.0, 141.5, 140.9, 138.3, 136.2 (q, J=40.5 Hz), 122.3, 120.2 (q, J=268.4 Hz), 85.1, 54.8; $^{19}$F NMR (376 MHz, Acetone-$d_6$) δ −64.41 (s, 3F); HRMS (ESI): Calc'd. for $C_{26}H_{19}F_6I_2N_{12}O_2^+$ [2M+H]$^+$: 870.9681, Observed: 870.9661.

Example 31. Synthesis of 6-methoxy-N-(3-iodophenyl)-2-(trifluoromethyl)-1H-imidazo[4,5-b]pyrazin-5-amine (2-31)

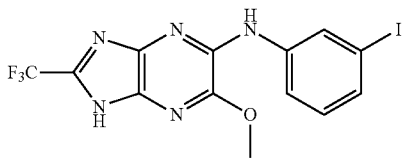 [SMILES: COc1nc2[nH]c(C(F)(F)F)nc2nc1Nc1cccc(I)c1]

Compound 2-31 was synthesized by procedure 2A with N-(3-Iodophenyl)-6-methoxy-[1,2,5]oxadiazolo[3,4-b]pyrazin-5-amine (1-170) to yield 2-31 in 52% as a light yellow solid. $^1$H NMR (500 MHz, Acetone-$d_6$) δ 8.53 (d, 1H, J=1.9 Hz), 8.51 (brs, 1H), 7.93 (ddd, H, J=8.2, 2.2, 0.9 Hz), 7.41 (ddd, H, J=8.2, 2.2, 0.9 Hz), 7.13 (t, 2H, J=8.2 Hz), 4.09 (s, 3H); $^{13}$C NMR (125 MHz, Acetone-$d_6$) δ 148.1, 141.4, 140.6, 135.4 (q, J=40.8 Hz), 131.1, 130.4, 127.6, 119.3 (q, J=268.5 Hz), 118.7, 93.6, 53.9; $^{19}$F NMR (376 MHz, Acetone-$d_6$) δ −64.42 (s, 3F); HRMS (ESI): Calc'd. for $C_{26}H_{19}F_6I_2N_{12}O_2^+$ [2M+H]$^+$: 870.9681, Observed: 870.9663.

Example 32. Synthesis of 6-methoxy-N-(3-(trifluoromethyl)phenyl)-2-(trifluoromethyl)-1H-imidazo[4,5-b]pyrazin-5-amine (2-32)

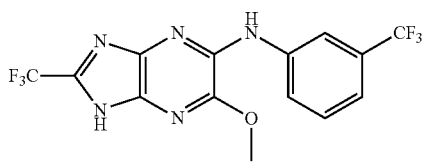 [SMILES: COc1nc2[nH]c(C(F)(F)F)nc2nc1Nc1cccc(C(F)(F)F)c1]

Compound 2-32 was synthesized by procedure 2A with 6-Methoxy-N-(3-(trifluoromethyl)phenyl)-[1,2,5]oxadiazolo[3,4-b]pyrazin-5-amine (1-166) to yield 2-32 in 65% as a light yellow solid. $^1$H NMR (500 MHz, Acetone-$d_6$) δ 8.75 (brs, 1H), 8.49 (brs, 1H), 8.21 (d, 1H, J=8.2 Hz), 7.57 (t, 1H, J=8.2 Hz), 7.36 (d, 1H, J=8.2 Hz), 4.11 (s, 3H); $^{13}$C NMR (125 MHz, Acetone-$d_6$) δ 150.2 (q, J=1.7 Hz), 148.2, 140.9, 140.6, 135.7 (q, J=40.8 Hz), 130.4 (q, J=31.7 Hz), 130.0, 124.5 (q, J=271.5 Hz), 122.7, 119.3 (q, J=268.5 Hz), 118.4 (q, J=3.8 Hz), 115.5 (q, J=4.0 Hz), 54.0; $^{19}$F NMR (376 MHz, Acetone-$d_6$) δ −63.15 (s, 3F), −64.43 (s, 3F); HRMS (ESI): Calc'd. for $C_{14}H_{10}F_6N_5O^+$ [M+H]$^+$: 378.0784, Observed: 378.0794.

Example 33. Synthesis of 6-methoxy-N-(2-fluoro-4-(tert-butyl)phenyl)-2-(trifluoromethyl)-1H-imidazo[4,5-b]pyrazin-5-amine (2-33)

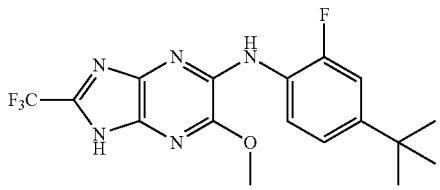 [SMILES: COc1nc2[nH]c(C(F)(F)F)nc2nc1Nc1ccc(C(C)(C)C)cc1F]

Compound 2-33 was synthesized by procedure 2A with N-(4-(tert-Butyl)-2-fluorophenyl)-6-methoxy-[1,2,5]oxadiazolo[3,4-b]pyrazin-5-amine (1-168) to yield 2-33 in 57% as a light yellow solid. $^1$H NMR (500 MHz, Acetone-$d_6$) δ 8.63 (d, 1H, J=8.1 Hz), 7.91 (brs, 1H), 7.14 (dd, 2H, J=8.7, 1.1 Hz), 4.16 (s, 3H), 1.34 (s, 9H); $^{13}$C NMR (125 MHz, Acetone-$d_6$) δ 152.5 (d, J=241.5 Hz), 151.6, 148.9, 148.2 (d, J=3.5 Hz), 141.7, 136.1 (q, J=41.0 Hz), 127.7 (d, J=10.3 Hz), 121.7 (d, J=3.1 Hz), 121.1 (d, J=8.5 Hz), 120.2 (q, J=268.4 Hz), 120.0, 114.3 (d, J=19.0 Hz), 55.0, 35.2, 31.8; $^{19}$F NMR (376 MHz, Acetone-$d_6$) δ −64.37 (s, 3F), −135.04 (s, 1F); HRMS (ESI): Calc'd. for $C_{17}H_{18}F_4N_5O^+$[M+H]$^+$: 384.1442, Observed: 384.1443.

Example 34. Synthesis of 6-methoxy-2-(perfluoroethyl)-N-(4-(trifluoromethoxy)phenyl)-1H-imidazo[4,5-b]pyrazin-5-amine (2-34)

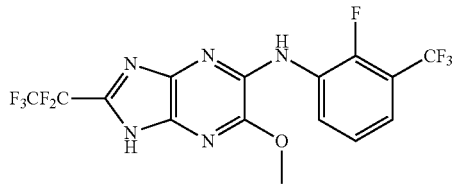

Compound 2-34 was synthesized by procedure 2A with N-(2-Fluoro-3-(trifluoromethyl)phenyl)-6-methoxy-[1,2,5]oxadiazolo[3,4-b]pyrazin-5-amine (1-140) to yield 2-34 in 65% as a light yellow solid. $^1$H NMR (500 MHz, Acetone-$d_6$) δ 8.78 (brs, 1H), 8.11 (brs, 1H), 7.44 (m, 2H), 4.17 (s, 3H); $^{13}$C NMR (125 MHz, Acetone-$d_6$) δ 151.5 (d, J=254.1 Hz), 150.5, 149.2, 141.2, 135.8 (t, J=29.9 Hz), 130.0 (d, J=9.3 Hz), 126.9, 125.5 (d, J=4.6 Hz), 123.8 (q, J=271.6 Hz), 120.9 (q, J=4.6 Hz), 120.1 (q, J=268.8 Hz), 118.5 (dd, J=32.8, 10.7 Hz), 55.2; $^{19}$F NMR (376 MHz, Acetone-$d_6$) δ −61.71 (d, 3F, J=13.0 Hz), −84.23 (d, 3F, J=3.0 Hz), −114.17 (d, 3F, J=3.1 Hz) −132.12 (s, 1F); HRMS (ESI): Calc'd. for $C_{15}H_9F_9N_5O^+$ [M+H]$^+$: 446.0658, Observed: 446.0661.

Example 35. Synthesis of 6-butoxy-N-(4-(trifluoromethoxy)phenyl)-2-(trifluoromethyl)-1H-imidazo[4,5-b]pyrazin-5-amine (2-35)

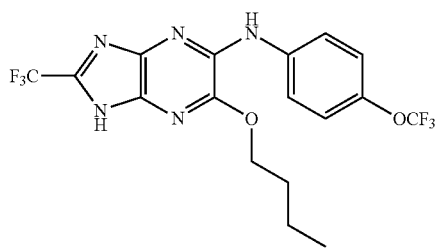 [SMILES: CCCCOc1nc2[nH]c(C(F)(F)F)nc2nc1Nc1ccc(OC(F)(F)F)cc1]

Compound 2-35 was synthesized by procedure 2A with 6-Butoxy-N-(4-(trifluoromethoxy)phenyl)-[1,2,5]oxadiazolo[3,4-b]pyrazin-5-amine (1-181) to yield 2-35 in 53% as a light yellow solid. $^1$H NMR (500 MHz, Acetone-$d_6$) δ 8.59 (brs, 1H), 8.05 (d, 2H, J=9.1 Hz), 7.32 (d, 2H, J=8.5 Hz), 4.51 (t, 2H, J=6.7 Hz), 1.86 (m, 2H), 1.53 (m, 2H), 0.99 (t, 3H, J=7.4 Hz); $^{13}$C NMR (125 MHz, Acetone-$d_6$) δ 148.6, 144.4 (d, J=1.7 Hz), 141.6, 140.0, 136.1 (q, J=40.9 Hz), 122.4, 121.7, 121.5 (q, J=254.5 Hz), 120.2 (q, J=268.5 Hz), 68.0, 31.4, 19.8, 14.1; $^{19}$F NMR (376 MHz, Acetone-$d_6$) δ −58.91 (s, 3F), −64.42 (s, 3F); HRMS (ESI): Calc'd. for $C_{17}H_{16}F_6N_5O_2^+$ [M+H]$^+$: 436.1203, Observed: 436.1180.

Example 36. Synthesis of 6-(2,2,2-trifluoroethoxy)-N-(4-(trifluoromethoxy)phenyl)-2-(trifluoromethyl)-1H-imidazo[4,5-b]pyrazin-5-amine (2-36)

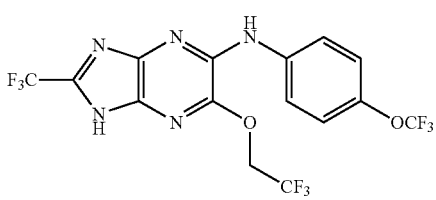 [SMILES: FC(F)(F)COc1nc2[nH]c(C(F)(F)F)nc2nc1Nc1ccc(OC(F)(F)F)cc1]

Compound 2-36 was synthesized by procedure 2A with N-(2-Fluorophenyl)-6-(2,2,2-trifluoroethoxy)-[1,2,5]oxadiazolo[3,4-b]pyrazin-5-amine (1-187) to yield 2-36 in 59% as a light yellow solid. $^1$H NMR (500 MHz, Acetone-$d_6$) δ 8.77 (brs, 1H), 8.02 (d, 2H, J=9.1 Hz), 7.32 (d, 2H, J=8.6 Hz), 5.15 (q, 2H, J=8.7 Hz); $^{13}$C NMR (125 MHz, Acetone-$d_6$) δ 146.4, 144.9 (d, J=1.9 Hz), 141.4, 139.7, 137.4 (q, J=41.1 Hz), 124.7 (q, J=277.0 Hz), 122.3, 121.6 (q, J=254.7 Hz), 120.1 (q, J=268.7 Hz), 63.5 (q, J=36.3 Hz); $^{19}$F NMR (376 MHz, Acetone-$d_6$) δ −58.88 (s, 3F), −64.62 (s, 3F), −73.82 (t, 3F, J=8.8 Hz); HRMS (ESI): Calc'd. for $C_{15}H_9F_9N_5O_2^+$ [M+H]$^+$: 462.0607, Observed: 462.0586.

Example 37. Synthesis of 6-ethoxy-N-(4-(trifluoromethoxy)phenyl)-2-(trifluoromethyl)-1H-imidazo[4,5-b]pyrazin-5-amine (2-37)

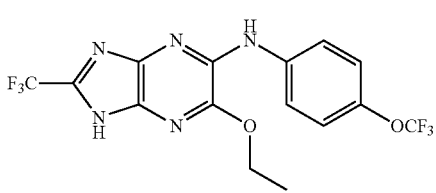 [SMILES: CCOc1nc2[nH]c(C(F)(F)F)nc2nc1Nc1ccc(OC(F)(F)F)cc1]

Compound 2-37 was synthesized by procedure 2A with 6-ethoxy-N-(4-(trifluoromethoxy)phenyl)-[1,2,5]oxadiazolo[3,4-b]pyrazin-5-amine (1-203) to yield 2-37 in 68% as a light yellow solid. $^1$H NMR (500 MHz, Acetone-$d_6$) δ 8.58 (brs, 1H), 8.06 (d, 2H, J=9.1 Hz), 7.31 (d, 2H, J=8.7 Hz), 4.56 (q, 2H, J=7.1 Hz), 1.46 (t, 3H, J=7.1 Hz); $^{13}$C NMR (125 MHz, Acetone-$d_6$) δ 148.5, 144.5 (q, J=1.7 Hz), 141.7, 140.1, 136.3 (q, J=41.0 Hz), 122.3, 121.60, 121.57 (q, J=254.5 Hz), 120.2 (q, J=268.5 Hz), 64.1, 14.6; $^{19}$F NMR (376 MHz, Acetone-$d_6$) δ −58.89 (s, 3F), −64.40 (s, 3F); HRMS (ESI): Calc'd. for $C_{15}H_{11}F_6N_5NaO_2^+$ [M+Na]$^+$: 430.0709, Observed: 430.0701.

Example 38. Synthesis of 6-ethoxy-N-(2-fluoro-4-(trifluoromethoxy)phenyl)-2-(trifluoromethyl)-1H-imidazo[4,5-b]pyrazin-5-amine (2-38)

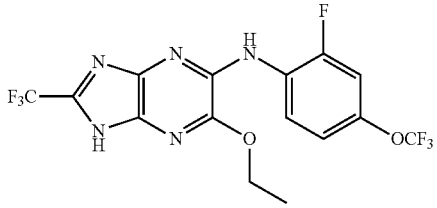 [SMILES: CCOc1nc2[nH]c(C(F)(F)F)nc2nc1Nc1ccc(OC(F)(F)F)cc1F]

Compound 2-38 was synthesized by procedure 2A with 6-ethoxy-N-(2-fluoro-4-(trifluoromethoxy)phenyl)-[1,2,5]oxadiazolo[3,4-b]pyrazin-5-amine (1-200) to yield 2-38 in 65% as a light yellow solid. $^1$H NMR (500 MHz, Acetone-$d_6$) δ 8.57 (t, 1H, J=9.0 Hz), 8.03 (brs, 1H), 7.36 (dd, 1H, J=11.3, 2.3 Hz), 7.26 (d, 1H, J=9.0 Hz), 4.59 (q, 2H, J=7.1 Hz), 1.50 (t, 3H, J=7.1 Hz); $^{13}$C NMR (125 MHz, Acetone-$d_6$) δ 154.2 (d, J=247.0 Hz), 148.5, 144.4 (d, J=11.0 Hz), 141.2, 136.5 (q, J=40.7 Hz), 128.1 (d, J=10.3 Hz), 123.3, 121.4 (q, J=255.8 Hz), 120.1 (q, J=268.6 Hz), 118.2 (q, J=3.8 Hz), 110.2 (d, J=23.6 Hz), 64.4, 14.5; $^{19}$F NMR (376 MHz, Acetone-$d_6$) δ −59.13 (s, 3F), −64.53 (s, 3F), −125.60 (s, 1F); HRMS (ESI): Calc'd. for $C_{15}H_{11}F_7N_5O_2^+$ [M+H]$^+$: 426.0795, Observed: 426.0799.

Example 39. Synthesis of 6-propoxy-N-(2-fluoro-4-(trifluoromethoxy)phenyl)-2-(trifluoromethyl)-1H-imidazo[4,5-b]pyrazin-5-amine (2-39)

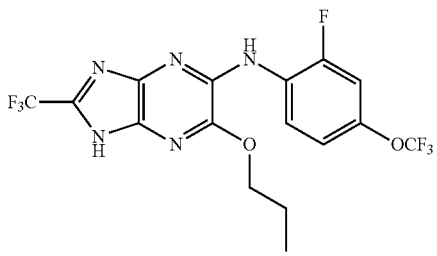 [SMILES: CCCOc1nc2[nH]c(C(F)(F)F)nc2nc1Nc1ccc(OC(F)(F)F)cc1F]

Compound 2-39 was synthesized by procedure 2A with N-(2-fluoro-4-(trifluoromethoxy)phenyl)-6-propoxy-[1,2,5]oxadiazolo[3,4-b]pyrazin-5-amine (1-201) to yield 2-39 in 59% as a light yellow solid. $^1$H NMR (500 MHz, Acetone-$d_6$) δ 8.58 (t, 1H, J=9.0 Hz), 8.02 (brs, 1H), 7.36 (dd, 1H, J=11.4, 2.7 Hz), 7.27 (d, 1H, J=9.0 Hz), 4.50 (t, 2H, J=6.6 Hz), 1.93 (h, 2H, J=7.3 Hz), 1.10 (t, 3H, J=7.4 Hz); $^{13}$C NMR (125 MHz, Acetone-$d_6$) δ 154.1 (d, J=246.8 Hz), 148.6, 144.3 (d, J=10.0 Hz), 141.2, 136.5 (q, J=40.9 Hz), 128.1 (d, J=10.1 Hz), 123.3, 121.4 (q, J=255.9 Hz), 120.1 (q, J=268.7 Hz), 118.2 (q, J=3.8 Hz), 110.2 (d, J=23.5 Hz), 69.9, 22.6, 10.7; $^{19}$F NMR (376 MHz, Acetone-$d_6$) δ −59.14 (s, 3F), −64.54 (s, 3F), −126.01 (s, 1F); HRMS (ESI): Calc'd. for $C_{16}H_{13}F_7N_5O_2^+$ [M+H]$^+$: 440.0952, Observed: 440.0956.

Example 40. Synthesis of 6-methoxy-2-(trifluoromethyl)-5-(4-(trifluoromethyl)phenoxy)-1H-imidazo[4,5-b]pyrazine (2-40)

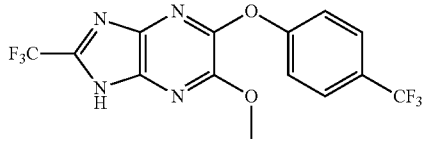 [SMILES: COc1nc2[nH]c(C(F)(F)F)nc2nc1Oc1ccc(C(F)(F)F)cc1]

Compound 2-40 was synthesized by procedure 2A with 5-methoxy-6-(4-(trifluoromethyl)phenoxy)-[1,2,5]oxadiazolo[3,4-b]pyrazine (1-199) to yield 2-40 in 70% as a light yellow solid. $^1$H NMR (500 MHz, Acetone-$d_6$) δ 7.84 (d, 2H, J=8.4 Hz), 7.51 (d, 2H, J=8.4 Hz), 4.12 (s, 3H); $^{13}$C NMR (125 MHz, Acetone-$d_6$) δ 157.6, 151.0, 148.3, 139.1 (q, J=41.1 Hz), 127.9 (q, J=3.9 Hz), 127.4 (q, J=32.6 Hz), 125.2 (q, J=271.1 Hz), 122.6, 119.8 (q, J=269.2 Hz), 55.0; $^{19}$F NMR (376 MHz, Acetone-$d_6$) δ −62.52 (s, 3F), −65.03 (s, 3F); HRMS (ESI): Calc'd. for $C_{14}H_9F_6N_4O^+$ [M+H]$^+$: 379.0624, Observed: 379.0623.

Example 41. Synthesis of N-(2-iodo-4-(trifluoromethoxy)phenyl)-6-methoxy-2-(trifluoromethyl)-1H-imidazo[4,5-b]pyrazin-5-amine (2-41)

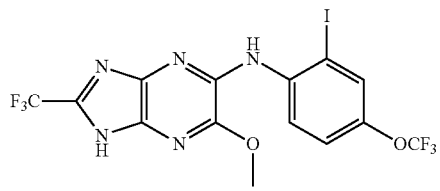 [SMILES: COc1nc2[nH]c(C(F)(F)F)nc2nc1Nc1ccc(OC(F)(F)F)cc1I]

Compound 2-41 was synthesized by procedure 2A with N-(2-Iodo-4-(trifluoromethoxy)phenyl)-6-methoxy-[1,2,5]oxadiazolo[3,4-b]pyrazin-5-amine (1-171) to yield 2-41 in 46% as a light yellow solid. $^1$H NMR ((CD$_3$)$_2$CO, 400 MHz) δ 12.91 (bs, 1H), 8.67 (d, 1H, J=9.1 Hz), 7.98 (s, 1H), 7.80 (s, 1H), 7.37 (d, 1H, J=9.1 Hz), 4.15 (s, 3H); $^{13}$C NMR ((CD$_3$)$_2$CO, 100 MHz) δ 148.84, 144.22 (q, J=1.9 Hz), 140.77, 140.14, 136.83 (q, J=41.3 Hz), 134.80, 134.53, 132.46, 122.61, 121.37 (q, J=256.1 Hz), 120.75, 120.03 (q, J=268.2 Hz), 89.99, 55.36; $^{19}$F NMR ((CD$_3$)$_2$CO, 376 MHz) δ −58.99 (s, 3F), −64.48 (s, 3F); HRMS (ESI): Calc'd. for $C_{14}H_9F_6IN_5O_2^+$ [M+H]$^+$: 519.9705, Observed: 519.9714.

Example 42. Synthesis of N-(2-chloro-4-(trifluoromethoxy)phenyl)-6-methoxy-2-(trifluoromethyl)-1H-imidazo[4,5-b]pyrazin-5-amine (2-42)

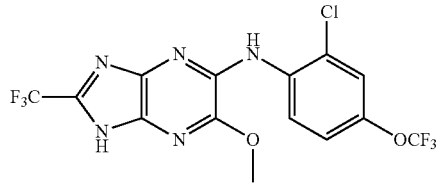 [SMILES: COc1nc2[nH]c(C(F)(F)F)nc2nc1Nc1ccc(OC(F)(F)F)cc1Cl]

Compound 2-42 was synthesized by procedure 2A with N-(2-Chloro-4-(trifluoromethoxy)phenyl)-6-methoxy-[1,2,5]oxadiazolo[3,4-b]pyrazin-5-amine (1-172) to yield 2-42 in 72% as a light yellow solid. $^1$H NMR ((CD$_3$)$_2$CO, 400 MHz) δ 12.84 (bs, 1H), 8.70 (d, 1H, J=9.1 Hz), 7.82 (s, 1H), 7.34 (s, 1H), 7.16 (d, 1H, J=9.1 Hz), 4.05 (s, 3H); $^{13}$C NMR ((CD$_3$)$_2$CO, 100 MHz) δ 148.38, 143.30 (q, J=1.9 Hz), 139.76, 136.75 (q, J=41.2 Hz), 135.70, 134.29, 122.82, 122.60, 121.13 (q, J=256.7 Hz), 120.99, 120.13, 119.76 (q, J=269.4 Hz), 55.03; $^{19}$F NMR ((CD$_3$)$_2$CO, 376 MHz) δ −59.12 (s, 3F), −64.50 (s, 3F); HRMS (ESI): Calc'd. for C$_{14}$H$_9$F$_6$ClN$_5$O$_2$$^+$ [M+H]$^+$: 428.0349, Observed: 428.0357.

Example 43. Synthesis of N-(3-chloro-4-(trifluoromethoxy)phenyl)-6-methoxy-2-(trifluoromethyl)-1H-imidazo[4,5-b]pyrazin-5-amine (2-43)

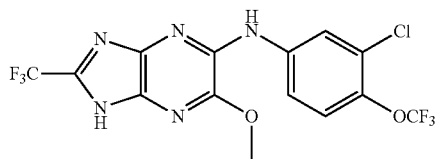 [SMILES: COc1nc2[nH]c(C(F)(F)F)nc2nc1Nc1ccc(OC(F)(F)F)c(Cl)c1]

Compound 2-43 was synthesized by procedure 2A with N-(3-Chloro-4-(trifluoromethoxy)phenyl)-6-methoxy-[1,2,5]oxadiazolo[3,4-b]pyrazin-5-amine (1-173) to yield 2-43 in 42% as a light yellow solid. $^1$H NMR ((CD$_3$)$_2$CO, 400 MHz) δ 12.84 (bs, 1H), 8.64 (s, 1H), 8.40 (s, 1H), 7.86 (d, 1H, J=9.1 Hz), 7.37 (d, 1H, J=9.1 Hz), 4.04 (s, 3H); $^{13}$C NMR ((CD$_3$)$_2$CO, 100 MHz) δ 148.79, 140.87, 140.85, 139.67 (q, J=2.0 Hz), 136.41 (q, J=41.2 Hz), 134.71, 134.12, 127.44, 123.79, 121.42 (q, J=257.4 Hz), 120.98, 119.96 (q, J=267.3 Hz), 119.53, 54.68; $^{19}$F NMR ((CD$_3$)$_2$CO, 376 MHz) δ −58.98 (s, 3F), −64.41 (s, 3F); HRMS (ESI): Calc'd. for C$_{14}$H$_9$F$_6$ClN$_5$O$_2$$^+$ [M+H]$^+$: 428.0349, Observed: 428.0350.

Example 44. Synthesis of N-(3-bromo-4-(trifluoromethoxy)phenyl)-6-methoxy-2-(trifluoromethyl)-1H-imidazo[4,5-b]pyrazin-5-amine (2-44)

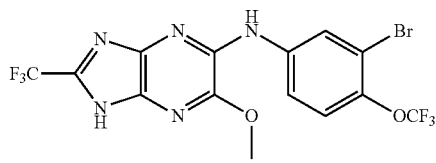 [SMILES: COc1nc2[nH]c(C(F)(F)F)nc2nc1Nc1ccc(OC(F)(F)F)c(Br)c1]

Compound 2-44 was synthesized by procedure 2A with 1-174 to yield 2-44 in 51% as a light yellow solid. $^1$H NMR ((CD$_3$)$_2$CO, 400 MHz) δ 13.03 (bs, 1H), 8.61 (s, 1H), 8.52 (d, 1H, J=2.7 Hz), 7.91 (dd, 1H, J=9.1 Hz), 7.35 (dq, 1H, J=9.1 Hz), 4.03 (s, 3H); $^{13}$C NMR ((CD$_3$)$_2$CO, 100 MHz) δ 148.57, 140.85 (q, J=1.9 Hz), 140.69, 140.64, 136.22 (q, J=41.0 Hz), 134.46, 134.01, 123.79, 123.13, 121.21 (q, J=257.4 Hz), 119.93, 119.80 (q, J=268.5 Hz), 116.05, 54.51; $^{19}$F NMR ((CD$_3$)$_2$CO, 376 MHz) δ −58.61 (s, 3F), −64.38 (s, 3F); HRMS (ESI): Calc'd. for C$_{14}$H$_9$F$_6$BrN$_5$O$_2$$^+$ [M+H]$^+$: 471.9844, Observed: 471.9845.

Example 45. Synthesis of 5-isopropoxy-2-(trifluoromethyl)-N-(4-(trifluoromethyl)phenyl)-1H-imidazo[4,5-b]pyrazin-6-amine (2-45)

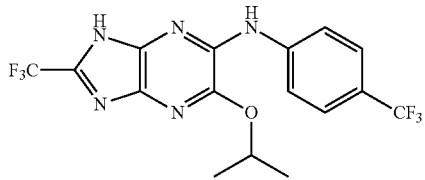 [SMILES: CC(C)Oc1nc2nc(C(F)(F)F)[nH]c2nc1Nc1ccc(C(F)(F)F)cc1]

Compound 2-45 was synthesized by procedure 2A with 6-Isopropoxy-N-(4-(trifluoromethyl)phenyl)-[1,2,5]oxadiazolo[3,4-b]pyrazin-5-amine 1-183 to yield 2-45 in 67% as a light yellow solid. $^1$H NMR ((CD$_3$)$_2$CO, 400 MHz) δ 13.04 (bs, 1H), 8.70 (brs, 1H), 8.16 (d, 2H, J=8.4 Hz), 7.66 (d, 2H, J=8.4 Hz), 5.49 (h, 1H, J=6.2 Hz), 1.45 (h, 6H, J=6.2 Hz); $^{19}$F NMR ((CD$_3$)$_2$CO, 376 MHz) δ −62.16 (s, 3H), −64.49 (s, 3H); HRMS (ESI): Calc'd. for C$_{16}$H$_{13}$F$_6$N$_5$O$^+$ [M+H]$^+$: 405.1019, Observed: 405.0999.

Example 46. Synthesis of 5-(2-fluorophenoxy)-2-(trifluoromethyl)-N-(4-(trifluoromethyl)phenyl)-1H-imidazo[4,5-b]pyrazin-6-amine (2-46)

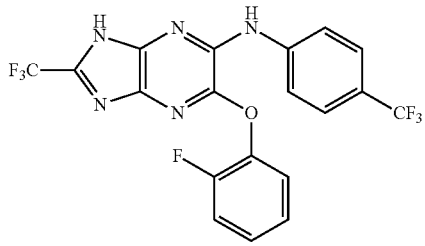 [SMILES: Fc1ccccc1Oc1nc2nc(C(F)(F)F)[nH]c2nc1Nc1ccc(C(F)(F)F)cc1]

Compound 2-46 was synthesized by procedure 2A with 6-(2-Fluorophenoxy)-N-(4-(trifluoromethyl)phenyl)-[1,2,5]oxadiazolo[3,4-b]pyrazin-5-amine (1-184) to yield 2-46 in 21% as a light yellow solid. $^1$H NMR ((CD$_3$)$_2$CO, 400 MHz) δ 13.11 (brs, 1H), 9.19 (brs, 1H), 8.28 (d, 2H, J=8.6 Hz), 7.71 (d, 2H, J=8.6 Hz), 7.47 (td, 1H, J=8.0, 1.3 Hz), 7.44–7.31 (m, 3H); $^{19}$F NMR ((CD$_3$)$_2$CO, 376 MHz) δ −62.18 (s, 3F), −64.82 (s, 3F), −129.73–−129.82 (m, 1F); HRMS (ESI): Calc'd. for C$_{19}$H$_{11}$F$_7$N$_5$O$^+$ [M+H]$^+$: 458.0846, Observed: 458.0846.

Example 47. Synthesis of 2-(trifluoromethyl)-5-(4-(trifluoromethyl)phenoxy)-N-(4-(trifluoromethyl)phenyl)-1H-imidazo[4,5-b]pyrazin-6-amine (2-47)

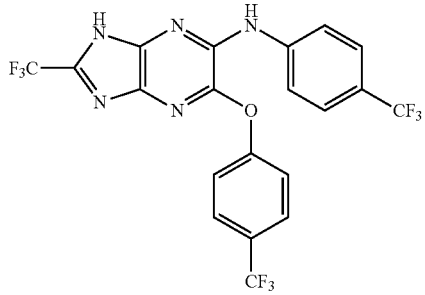 [SMILES: FC(F)(F)c1ccc(Nc2nc3[nH]c(C(F)(F)F)nc3nc2Oc2ccc(C(F)(F)F)cc2)cc1]

Compound 2-47 was synthesized by procedure 2A with 6-(4-(Trifluoromethyl)phenoxy)-N-(4-(trifluoromethyl)phenyl)-[1,2,5]oxadiazolo[3,4-b]pyrazin-5-amine (1-185) to yield 2-47 in 17% as a light yellow solid. $^1$H NMR ((CD$_3$)$_2$CO, 400 MHz) δ 13.19 (bs, 1H), 9.20 (brs, 1H), 8.25 (d, 2H, J=8.5 Hz), 7.88 (d, 2H, J=8.5 Hz), 7.71 (d, 2H, J=8.5 Hz), 7.62 (d, 2H, J=8.5 Hz); $^{19}$F NMR (376 MHz, Acetone-d$_6$) δ −62.19 (s, 3F), −62.53 (s, 3F), −64.84 (s, 3F); HRMS (ESI): Calc'd. for C$_{20}$H$_{11}$F$_9$N$_5$O$^+$ [M+H]$^+$: 508.0814, Observed: 508.0816.

Example 49. Synthesis of 5-methoxy-N-methyl-2-(trifluoromethyl)-N-(4-(trifluoromethyl)phenyl)-1H-imidazo[4,5-b]pyrazin-6-amine (2-49)

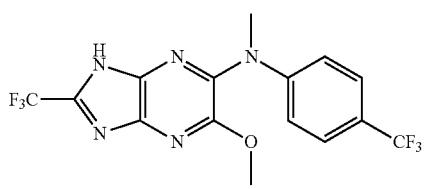 [SMILES: COc1nc2nc(C(F)(F)F)[nH]c2nc1N(C)c1ccc(C(F)(F)F)cc1]

Compound 2-49 was synthesized by procedure 2A with 6-Methoxy-N-methyl-N-(4-(trifluoromethyl)phenyl)-[1,2,5]oxadiazolo[3,4-b]pyrazin-5-amine (1-177) to yield 2-49 in 32% as a light yellow solid. $^1$H NMR (400 MHz, Acetone-d$_6$) δ 13.17 (brs, 1H), 7.57 (d, 2H, J=8.4 Hz), 7.13 (d, 2H, J=8.4 Hz), 3.85 (s, 3H), 3.53 (s, 3H); $^{13}$C NMR (100 MHz, Acetone-d$_6$) δ 153.68, 151.85, 143.75, 139.38 (q, J=41.2 Hz), 137.84, 136.65, 126.67 (q, J=3.9 Hz), 125.80 (q, J=271.3 Hz), 123.51 (q, J=32.5 Hz), 120.00 (q, J=269.1 Hz), 119.93, 54.48, 39.87; $^{19}$F NMR (376 MHz, Acetone-d$_6$) δ −62.06 (s, 3F), −64.95 (s, 3F); HRMS (ESI): Calc'd. for C$_{15}$H$_{12}$F$_6$N$_5$O$^+$ [M+H]$^+$: 392.0941, Observed: 392.0930.

Example 50. Synthesis of 5-methoxy-N-(4-(trifluoromethyl)phenyl)-1H-imidazo[4,5-b]pyrazin-6-amine (2-50)

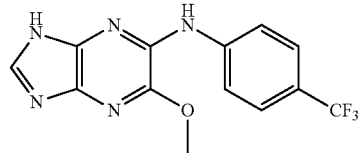 [SMILES: COc1nc2nc[nH]c2nc1Nc1ccc(C(F)(F)F)cc1]

Compound 2-50 was synthesized by procedure 2D with 6-Methoxy-N-(4-(trifluoromethyl)phenyl)-[1,2,5]oxadiazolo[3,4-b]pyrazin-5-amine (1-165) to yield 2-50 in 58% as a light yellow solid. $^1$H NMR (400 MHz, Acetone-d$_6$) δ 11.97 (brs, 1H), 8.50 (brs, 1H), 8.19 (d, 2H, J=8.3 Hz), 8.14 (s, 1H), 7.63 (d, 2H, J=8.6 Hz), 4.06 (s, 3H); $^{19}$F NMR (376 MHz, Acetone-d$_6$) δ −61.99 (s, 3F); HRMS (ESI): Calc'd. for C$_{13}$H$_{11}$F$_3$N$_5$O$^+$ [M+H]$^+$: 310.0910, Observed: 310.0900.

Example 51. Synthesis of 5-methoxy-2-methyl-N-(4-(trifluoromethyl)phenyl)-1H-imidazo[4,5-b]pyrazin-6-amine (2-51)

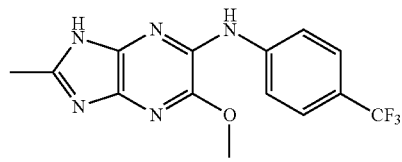 [SMILES: COc1nc2nc(C)[nH]c2nc1Nc1ccc(C(F)(F)F)cc1]

Compound 2-51 was synthesized by procedure 2D with 6-Methoxy-N-(4-(trifluoromethyl)phenyl)-[1,2,5]oxadiazolo[3,4-b]pyrazin-5-amine (1-165) to yield 2-51 in 39% as a light yellow solid. $^1$H NMR (400 MHz, Acetone-d$_6$) δ 11.76 (brs, 1H), 8.34 (brs, 1H), 8.14 (d, 2H, J=8.5 Hz), 7.60 (d, 2H, J=8.5 Hz), 4.02 (s, 3H), 2.60 (s, 3H); $^{13}$C NMR (100 MHz, Acetone-d$_6$) δ 149.88, 146.80, 145.47 (q, J=1.2 Hz), 144.75, 137.76, 126.67 (q, J=3.8 Hz), 125.89 (q, J=269.9 Hz), 122.67 (q, J=32.4 Hz), 119.33, 118.72, 54.41, 15.61 $^{19}$F NMR (376 MHz, Acetone-d$_6$) δ −61.93 (s, 3F)

Example 52. Synthesis of 5-((4-(trifluoromethoxy)phenyl)amino)-2-(trifluoromethyl)-1H-imidazo[4,5-b]pyrazin-6-ol (2-52)

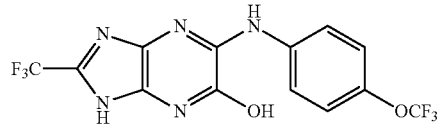 [SMILES: Oc1nc2[nH]c(C(F)(F)F)nc2nc1Nc1ccc(OC(F)(F)F)cc1]

Compound 2-52 was synthesized by procedure 2B with 2-1 to yield 2-52 in 60% as a light yellow solid. $^1$H NMR (500 MHz, Acetone-d$_6$)<59.01 (brs, 1H), 8.17 (d, 2H, J=9.1 Hz), 7.33 (d, 2H, J=8.9 Hz); $^{13}$C NMR (125 MHz, Acetone-d$_6$) δ 152.9, 147.8, 144.8 (d, J=2.3 Hz), 139.5, 130.7 (q, J=41.8 Hz), 127.5, 126.1, 122.4, 121.54 (q, J=254.7 Hz), 121.50, 120.6, 120.2 (q, J=267.3 Hz); $^{19}$F NMR (376 MHz, Acetone-$d_6$) δ −58.88 (s, 3F), −63.49 (s, 3F); HRMS (ESI): Calc'd. for $C_{13}H_8F_6N_5O_2^+$ [M+H]$^+$: 380.0582, Observed: 380.0593.

Example 53. Synthesis of 5-((2-fluoro-4-(trifluoromethoxy)phenyl)amino)-2-(trifluoromethyl)-1H-imidazo[4,5-b]pyrazin-6-ol (2-53)

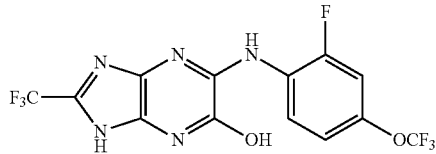 [SMILES: Oc1nc2[nH]c(C(F)(F)F)nc2nc1Nc1ccc(OC(F)(F)F)cc1F]

Compound 2-53 was synthesized by procedure 2B with 2-21 to yield 2-53 in 55% as a light yellow solid. $^1$H NMR (500 MHz, Acetone-$d_6$) δ 8.72 (t, 1H, J=9.1 Hz), 7.37 (dd, 1H, J=11.5, 2.7 Hz), 7.25 (d, 1H, J=9.1 Hz); $^{13}$C NMR (125 MHz, Acetone-$d_6$) δ 153.5 (d, J=247.0 Hz), 152.9, 147.3, 144.3 (dd, J=10.7, 2.3 Hz), 131.3 (q, J=41.5 Hz), 128.0, 127.8 (d, J=10.0 Hz), 126.1, 121.8 (d, J=2.1 Hz), 121.4 (q, J=255.9 Hz), 120.1 (q, J=267.5 Hz), 118.2 (d, J=3.5 Hz), 110.2 (d, J=23.2 Hz); $^{19}$F NMR (376 MHz, Acetone-$d_6$) δ −59.14 (s, 3F), −63.61 (s, 3F), −127.66 (t, 1F, J=10.1 Hz); HRMS (ESI): Calc'd. for $C_{13}H_7F_7N_5O_2^+$ [M+H]$^+$: 398.0488, Observed: 398.0502.

Example 54. Synthesis of 5-((2-fluoro-3-(trifluoromethyl)phenyl)amino)-2-(trifluoromethyl)-1H-imidazo[4,5-b]pyrazin-6-ol (2-54)

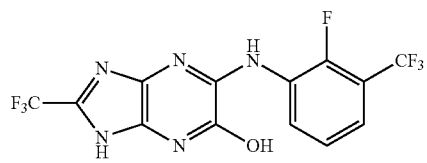 [SMILES: Oc1nc2[nH]c(C(F)(F)F)nc2nc1Nc1cccc(C(F)(F)F)c1F]

Compound 2-54 was synthesized by procedure 2B with 2-6 to yield 2-54 in 51% as a light yellow solid. $^1$H NMR (500 MHz, Acetone-$d_6$) δ 8.90 (brs, 1H), 8.82 (brs, 1H), 7.42 (m, 1H); $^{13}$C NMR (125 MHz, Acetone-$d_6$) δ 152.9, 150.9 (d, J=253.3 Hz), 147.3, 131.5 (q, J=41.6 Hz), 129.6 (d, J=9.0 Hz), 128.2, 125.6 (d, J=4.6 Hz), 125.4, 123.7 (q, J=271.5 Hz), 120.7 (q, J=4.8 Hz), 120.1 (q, J=267.8 Hz), 118.4 (dd, J=32.8, 10.4 Hz); $^{19}$F NMR (376 MHz, Acetone-$d_6$) δ −61.69 (s, 3F), −61.71 (d, 3F, J=13.0 Hz), −134.24 (m, 1F); HRMS (ESI): Calc'd. for $C_{13}H_7F_7N_5O^+$ [M+H]$^+$: 382.0539, Observed: 382.0532.

Example 55. Synthesis of 5-((4-(trifluoromethyl)phenyl)amino)-2-(trifluoromethyl)-1H-imidazo[4,5-b]pyrazin-6-ol (2-55)

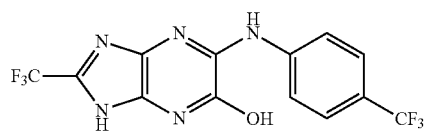 [SMILES: Oc1nc2[nH]c(C(F)(F)F)nc2nc1Nc1ccc(C(F)(F)F)cc1]

Compound 2-55 was synthesized by procedure 2B with 2-22 to yield 2-55 in 62% as a light yellow solid. $^1$H NMR (500 MHz, Acetone-$d_6$) δ 13.10 (brs, 1H), 12.02 (brs, 1H), 9.16 (brs, 1H), 8.27 (d, 2H, J=8.5 Hz), 7.69 (d, 2H, J=8.5 Hz); $^{13}$C NMR (125 MHz, Acetone-$d_6$) δ 152.9, 147.6, 143.7, 131.0 (q, J=41.6 Hz), 126.7 (q, J=3.8 Hz), 125.5 (q, J=270.4 Hz), 124.5 (q, J=32.3 Hz), 120.1 (q, J=267.4 Hz), 120.0; $^{19}$F NMR (376 MHz, Acetone-$d_6$) δ −62.25 (s, 3F), −63.59 (s, 3F); HRMS (ESI): Calc'd. for $C_{13}H_7F_6N_5O^+$ [M+H]$^+$: 363.0549, Observed: 363.0547.

Example 56. Synthesis of 5-((4-(tert-butyl)phenyl)amino)-2-(trifluoromethyl)-1H-imidazo[4,5-b]pyrazin-6-ol (2-56)

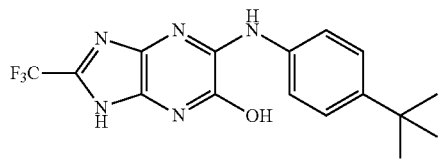 [SMILES: CC(C)(C)c1ccc(Nc2nc3nc(C(F)(F)F)[nH]c3nc2O)cc1]

Compound 2-56 was synthesized by procedure 2B with 2-19 to yield 2-56 in 61% as a light yellow solid. $^1$H NMR (500 MHz, Acetone-$d_6$) δ 8.79 (brs, 1H), 7.94 (d, 2H, J=8.7 Hz), 7.41 (d, 2H, J=8.7 Hz), 1.32 (s, 9H); $^{13}$C NMR (125 MHz, Acetone-$d_6$) δ 153.0, 147.9, 146.5, 137.6, 130.0 (q, J=41.4 Hz), 126.9, 126.5, 126.3, 125.8, 122.8, 118.6, 120.2 (q, J=267.1 Hz), 120.1, 34.8, 31.7; $^{19}$F NMR (376 MHz, Acetone-$d_6$) δ −63.38 (s, 3F); HRMS (ESI): Calc'd. for $C_{16}H_{17}F_3N_5O^+$ [M+H]$^+$: 352.1380, Observed: 352.13%.

Example 57. Synthesis of 6-methoxy-1-methyl-2-(trifluoromethyl)-N-(4-(trifluoromethyl)phenyl)-1H-imidazo[4,5-b]pyrazin-5-amine (2-57)

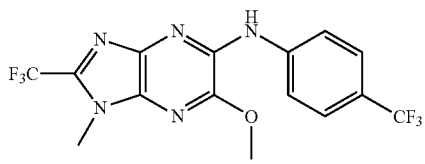 [SMILES: COc1nc2c(nc1Nc1ccc(C(F)(F)F)cc1)nc(C(F)(F)F)n2C]

Compound 2-57 was synthesized by procedure 2C with 2-22 to yield 2-57 in 34% as a light yellow solid. $^1$H NMR (500 MHz, Acetone-$d_6$) δ 8.73 (brs, 1H), 8.24 (d, 2H, J=8.5 Hz), 7.67 (d, 2H, J=8.5 Hz), 4.17 (s, 3H), 3.99 (s, 3H); HRMS (ESI): Calc'd. for $C_{14}H_{10}F_6N_5O^+$ [M+H]$^+$: 392.0941, Observed: 392.0932.

Example 58. Synthesis of 5-methoxy-1-methyl-2-(trifluoromethyl)-N-(4-(trifluoromethyl)phenyl)-1H-imidazo[4,5-b]pyrazin-6-amine (2-58)

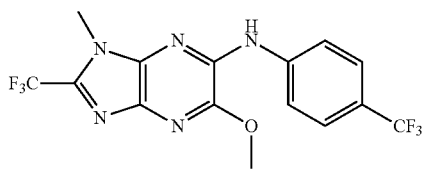 [SMILES: COc1nc2nc(C(F)(F)F)n(C)c2nc1Nc1ccc(C(F)(F)F)cc1]

Compound 2-58 was synthesized by procedure 2C with 2-22 to yield 2-58 in 34% as a light yellow solid. ¹H NMR (500 MHz, Acetone-d₆) δ 8.84 (brs, 1H), 8.25 (d, 2H, J=8.5 Hz), 7.69 (d, 2H, J=8.5 Hz), 4.06 (s, 3H), 4.00 (s, 3H); HRMS (ESI): Calc'd. for $C_{15}H_{12}F_6N_5O^+$ [M+H]⁺: 392.0941, Observed: 392.0934.

Example 59. Synthesis 1-methyl-2-(trifluoromethyl)-6-((4-(trifluoromethyl)phenyl)amino)-1H-imidazo[4,5-b]pyrazin-5-ol (2-59)

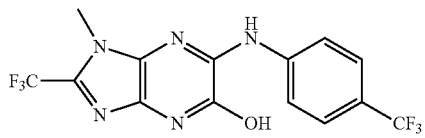

Compound 2-59 was synthesized by procedure 2B with 2-58 to yield 2-59 in 78% as a light yellow solid. ¹H NMR (500 MHz, Acetone-d₆) δ 11.75 (brs, 1H), 8.19 (brs, 1H), 8.37 (d, 2H, J=8.5 Hz), 7.73 (d, 2H, J=8.5 Hz), 4.01 (s, 3H); ¹³C NMR (125 MHz, Acetone-d₆) δ 153.0, 147.5, 143.6, 130.8 (q, J=39.7 Hz), 126.9 (q, J=3.9 Hz), 125.6 (q, J=269.9 Hz), 124.6 (q, J=32.3 Hz), 120.4 (q, J=267.9 Hz), 120.2; ¹⁹F NMR (376 MHz, Acetone-d₆) δ −62.16 (s, 3F), −62.31 (s, 3F); HRMS (ESI): Calc'd. for $C_{14}H_{10}F_6N_5O^+$ [M+H]⁺: 378.0784, Observed: 378.0786.

Example 60. Synthesis of 6-methoxy-2-phenyl-N-(4-(trifluoromethoxy)phenyl)-1H-imidazo[4,5-b]pyrazin-5-amine (2-60)

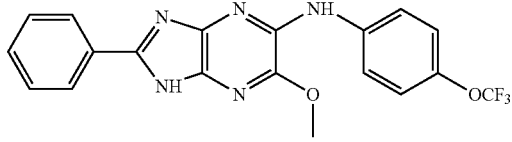 [SMILES: COc1nc2[nH]c(-c3ccccc3)nc2nc1Nc1ccc(OC(F)(F)F)cc1]

Compound 2-60 was synthesized by procedure 2D with 1-156 to yield 2-60; ¹⁹F NMR (376 MHz, Acetone-d₆) δ −58.83 (s, 3F); HRMS (ESI): Calc'd. for $C_{19}H_{15}F_3N_5O_2^+$ [M+H]⁺: 402.1172, Observed: 402.1174.

Example 61. Synthesis of 5-methoxy-N-(4-(trifluoromethoxy)phenyl)-2-(trifluoromethyl)-1H-imidazo[4,5-b]pyridin-6-amine (2-61)

Step. 1 Synthesis of 5,6-dichloro-3-nitropyridin-2-amine, 2-61-a

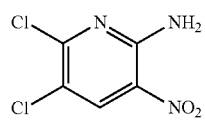

To a suspension of 6-chloro-3-nitropyridin-2-amine (20 g, 115 mmol) in acetic acid (100 mL) was added N-chlorosuccinimide (16.157 g, 121 mmol), and the obtained reaction mixture was stirred at 100° C. for one hour. The reaction mixture was allowed to cool to room temperature, and N-chlorosuccinimide (2.0 g) was added thereto. The obtained reaction mixture was stirred at 100° C. for 1 h. The obtained reaction mixture was allowed to cool to r.t. and acetic acid was removed via distillation. The residue was suspended in water, added sat. sodium bicarbonate aq. until pH=8 and the solid residue was filtered. The solid was then washed twice with water. The solid was collected, dissolved in acetone and precipitated with water, and filtered to afford 2-61-a as a pure yellow solid (11 g, 46%). ¹H NMR (400 MHz, DMSO-d₆) δ 8.59 (s, 1H), 8.34 (s, 2H).

Step 2. Synthesis of 5,6-dichloro-[1,2,5]oxadiazolo[3,4-b]pyridine 1-oxide, 2-61-b

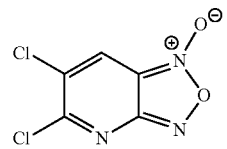 [SMILES: [O-][n+]1onc2nc(Cl)c(Cl)cc21]

2-61-a (4.50 g, 21.64 mmol) and iodobenzene diacetate (17.421 g, 54.087 mmol) were added to a sealed tube and stirred in Acetone (100 mL) at 80° C. for 16 h. The reaction was then concentrated reduced pressure to remove the solvent, and then acetic acid was removed via distillation at 110° C. under reduced pressure. The resulting crude product was purified by silica gel chromatography (0-100% ethyl acetate/hexanes) to afford 2-61-b as a yellow solid (2.00 g, 45%). ¹H NMR (400 MHz, Acetone-d6) δ 8.52 (s, 1H).

Step 3. Synthesis of 5,6-dichloro-[1,2,5]oxadiazolo[3,4-b]pyridine (2-61-c)

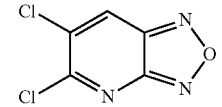

In a dry flask, 2-61-b (1.000 g, 14.56 mmol) was dissolved in dry DCM (50 mL) and triphenylphosphine (3.82 g, 14.56 mmol) was added slowly at 0° C. under argon. The mixture was stirred at 35° C. for 24 hours. The reaction was concentrated under reduced pressure and extracted with saturated sodium bicarbonate and Ethyl acetate 3×. All organic fractions were combined, dried over anhydrous sodium sulfate, concentrated and purified via silica gel chromatography (hexanes:Ethyl acetate 0-5%) to afford 2-61-c as off white solid (1.00 g, 54%). ¹H NMR (500 MHz, Acetone-d₆) δ 8.90 (s, 1H). ¹³C NMR (126 MHz, Acetone-d₆) δ 158.79, 157.25, 144.06, 134.70, 127.03.

Step 4. Synthesis of 6-chloro-5-methoxy-[1,2,5]oxadiazolo[3,4-b]pyridine (2-61-d)

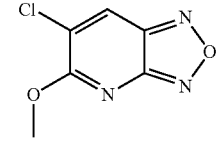

In a flame dried flask, NaH (0.13 g, 3.16 mmol 60% w/w dispersion) was added to dry THF (10 mL) and allowed to stir under argon for 1 min. Methanol (141 µL, 3.47 mmol) in dry THF (3 mL) was added dropwise over a minute, and the mixture was allowed to stir for 10 min. 5-3 (600 mg, 3.16 mmol) in dry THF (3 mL) was then added dropwise over 1 min. and the mixture was allowed to stir at r.t. for 30 min. The mixture was then reduced under pressure, and purified via Silica gel chromotography (hexanes:Ethyl acetate 0-3%) to afford 2-26-d as a white crystalline solid (338 mg, 92%). $^1$H NMR (500 MHz, Acetone-d$_6$) δ 8.57 (s, 1H), 4.21 (s, 3H).

Step 5. Synthesis of N-(2-fluorophenyl)-5-methoxy-2-(trifluoromethyl)-1H-imidazo[4,5-b]pyridin-6-amine

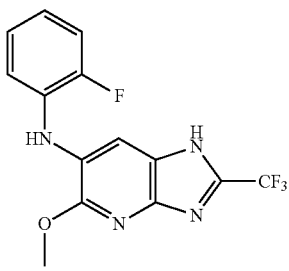 [SMILES: COc1nc2nc(C(F)(F)F)[nH]c2cc1Nc1ccccc1F]

Using procedure 2-D, 2-61 was afforded as a white solid (22 mg, 46%). $^1$H NMR (400 MHz, Acetone-d$_6$) δ 12.62 (s, 1H), 7.57 (d, J=1.4 Hz, 1H), 7.41 (td, J=8.3, 1.7 Hz, 1H), 7.27–7.12 (m, 2H), 7.09–6.98 (m, 1H), 6.77 (s, 1H), 4.06 (s, 3H). $^{19}$F NMR (376 MHz, Acetone-d$_6$) δ −64.49, −128.65. $^{13}$C NMR (126 MHz, Acetone-d$_6$) δ 154.39 (d, J=243.2 Hz), 153.62, 137.51 (q, J=40.5 Hz), 130.32 (d, J=12.5 Hz), 126.72, 124.77 (d, J=3.7 Hz), 122.78 (d, J=8.5 Hz), 120.60, 119.29 (d, J=268.8 Hz), 115.76 (d, J=19.6 Hz), 53.63. HRMS (ESP) m/z calcd for $C_{14}H_{11}F_4N_4O+$ (M+H)$^+$ 327.0864, found 327.0868.

Example 62. 5-methoxy-N-(4-(trifluoromethoxy)phenyl)-2-(trifluoromethyl)-1H-imidazo[4,5-b]pyridin-6-amine (2-62)

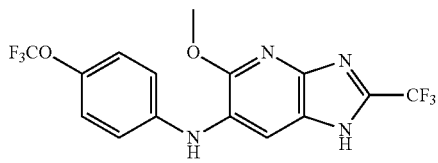 [SMILES: COc1nc2nc(C(F)(F)F)[nH]c2cc1Nc1ccc(OC(F)(F)F)cc1]

Using procedure 2-D, 2-62 was afforded as a beige solid (53 mg, 45%). $^1$H NMR (500 MHz, Acetone-d6) δ 7.83 (s, 1H), 7.38–7.17 (m, 5H), 4.03 (s, 3H). (NH not visible) 13C NMR (126 MHz, Chloroform-d) δ 154.98, 143.47 (d, J=2.3 Hz), 143.22, 138.58 (q, J=40.4 Hz), 127.29, 123.15, 121.60 (q, J=253.8 Hz), 120.19 (q, J=268.3 Hz), 119.73, 54.42. HRMS (ESI$^+$) m/z calcd for $C_{15}H_{11}F_6N_4O_2$ (M+H)$^+$ 393.0781, found 393.0784.

Example 63. 5-methoxy-N-(3-(trifluoromethoxy)phenyl)-2-(trifluoromethyl)-1H-imidazo[4,5-b]pyridin-6-amine (2-63)

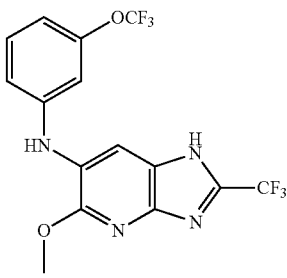 [SMILES: COc1nc2nc(C(F)(F)F)[nH]c2cc1Nc1cccc(OC(F)(F)F)c1]

Using procedure 2-D, 2-63 was afforded as a brown solid (21 mg, 17%). $^1$H NMR (500 MHz, Acetone-d6) δ 7.91 (s, 1H), 7.43–7.35 (m, 2H), 7.25–7.18 (m, 1H), 7.16–7.11 (m, 1H), 6.86-6.79 (m, 1H), 4.02 (s, 3H). 13C NMR (126 MHz, Acetone-d6) δ 155.44, 150.91 (d, J=2.1 Hz), 146.26, 138.94 (q, J=40.6 Hz), 131.51, 126.21, 122.48 (q, J=255.2 Hz), 120.17 (d, J=266.4 Hz), 116.38, 113.09, 110.24, 54.43. HRMS (ESP) m/z calcd for $C_{15}H_{11}F_6N_4O_2$ (M+H)$^+$ 393.0781, found 393.0783.

Example 64. 5-methoxy-2-(trifluoromethyl)-N-(4-(trifluoromethyl)phenyl)-1H-imidazo[4,5-b]pyridin-6-amine (2-64)

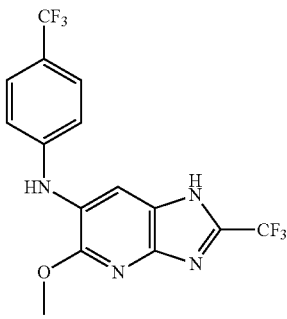 [SMILES: COc1nc2nc(C(F)(F)F)[nH]c2cc1Nc1ccc(C(F)(F)F)cc1]

Using procedure 2-D, 2-64 was afforded as a beige solid (21 mg, 35%). $^1$H NMR (400 MHz, Acetone-d$_6$) δ 12.81 (s, 1H), 8.00 (s, 1H), 7.61–7.50 (m, 3H), 7.30 (d, J=8.4 Hz, 2H), 4.01 (s, 3H). HRMS (ESP) m/z calcd for $C_{15}H_{11}F_6N_4O+$ (M+H)$^+$ 377.0832, found 377.0829.

Example 65. 5-methoxy-2-(trifluoromethyl)-N-(3-(trifluoromethyl)phenyl)-1H-imidazo[4,5-b]pyridin-6-amine (2-65)

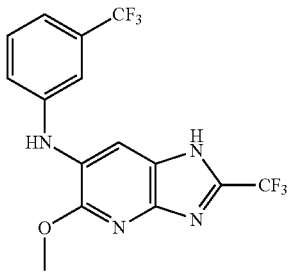

Using procedure 2-D, 2-65 was afforded as a beige solid (24 mg, 49%). $^1$H NMR (500 MHz, Acetone-$d_6$) δ 12.72 (s, 1H), 7.92 (s, 1H), 7.57–7.34 (m, 4H), 7.20 (dt, J=6.2, 1.7 Hz, 1H), 4.02 (s, 3H). HRMS (ESI$^+$) m/z calcd for $C_{15}H_{11}F_6N_4O^+$ (M+H)$^+$ 377.0832, found 377.0828.

Example 66. N-(2-fluoro-4-(trifluoromethoxy)phenyl)-5-methoxy-2-(trifluoromethyl)-1H-imidazo[4,5-b]pyridin-6-amine (2-66)

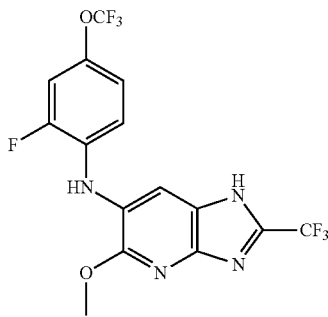 [SMILES: COc1nc2nc(C(F)(F)F)[nH]c2cc1Nc1ccc(OC(F)(F)F)cc1F]

Using procedure 2-D, 2-66 was afforded as a white solid (23 mg, 39%). $^1$H NMR (400 MHz, Acetone-$d_6$) δ 12.67 (s, 1H), 7.40 (t, J=9.1 Hz, 1H), 7.28 (ddq, J=11.4, 2.7, 0.9 Hz, 1H), 7.17-7.11 (m, 1H), 6.92 (s, 1H), 4.03 (s, 3H). HRMS (ESP) m/z calcd for $C_{15}H_{10}F_7N_4O_2+$ (M+H)$^+$411.0686, found 411.0688.

Example 67. N-(3-fluorophenyl)-5-methoxy-2-(trifluoromethyl)-3H-imidazo[4,5-b]pyridin-6-amine (2-67)

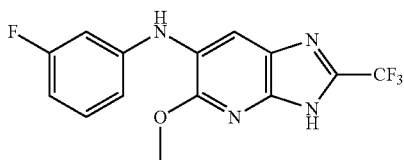 [SMILES: COc1nc2[nH]c(C(F)(F)F)nc2cc1Nc1cccc(F)c1]

Using procedure 2-D, 2-67 was afforded as a beige solid (41 mg, 65%). $^1$H NMR (400 MHz, Acetone-$d_6$) δ 12.96 (s, 1H), 7.88 (d, J=53.6 Hz, 1H), 7.47–7.13 (m, 1H), 7.00 (ddd, J=44.4, 27.7, 9.9 Hz, 2H), 6.63 (dt, J=30.6, 8.7 Hz, 1H), 4.00 (s, 3H); $^{13}$C NMR (126 MHz, Acetone-$d_6$) δ 164.67, 155.35, 145.97, 137.80 (q, J=41.0 Hz), 130.65, 129.25, 126.75, 124.88, 121.74, 116.72, 113.91, 112.37, 105.55, 53.56 (d, J=37.2 Hz); $^{19}$F NMR (376 MHz, Acetone-$d_6$) δ −64.50 (d, J=50.4 Hz), −113.82 (dd, J=105.3, 9.4 Hz). HRMS (ESP) =calcd for $C_{14}H_{11}F_4N_4O+$ [M+H]$^+$ 327.0791; found 327.0865.

Example 68. N-(2,3-Difluorophenyl)-5-methoxy-2-(trifluoromethyl)-3H-imidazo[4,5-b]pyridin-6-amine (2-68)

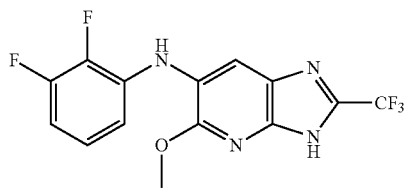 [SMILES: COc1nc2[nH]c(C(F)(F)F)nc2cc1Nc1cccc(F)c1F]

Using procedure 2-D, 2-68 was afforded as a beige solid (43 mg, 70%). $^1$H NMR (400 MHz, Acetone-$d_6$) δ 12.77 (s, 1H), 7.69 (s, 1H), 7.15–7.04 (m, 2H), 6.95 (s, 1H), 6.88 (qd, J=6.4, 5.9, 2.9 Hz, 1H), 4.02 (s, 3H); $^{13}$C NMR (101 MHz, Acetone-$d_6$) δ 152.34 (d, J=10.8 Hz), 149.91 (d, J=11.0 Hz), 137.95 (q, J=40.4 Hz), 124.37, 124.32, 124.28, 124.23, 123.22, 120.55, 117.87, 115.20, 114.57, 109.09, 53.62; $^{19}$F NMR (376 MHz, Acetone-$d_6$) δ −64.56, −140.27. HRMS (ESI$^+$)=calcd for $C_{14}H_{10}F_5N_4O+$ [M+H]$^+$ 345.0697; found 344.0772.

Example 69. 5-methoxy-N-(4-methoxyphenyl)-2-(trifluoromethyl)-3H-imidazo[4,5-b]pyridin-6-amine (2-69)

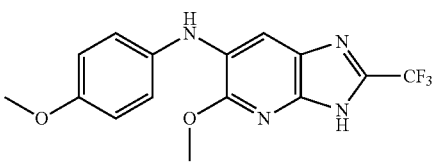 [SMILES: COc1ccc(Nc2cc3nc(C(F)(F)F)[nH]c3nc2OC)cc1]

Using procedure 2-D, 2-69 was afforded as a dark pink solid (13 mg, 21%). $^1$H NMR (400 MHz, Acetone-$d_6$) δ 12.50 (s, 1H), 7.54 (s, 1H), 7.34 (s, 1H), 7.25 (d, J=8.3 Hz, 2H), 6.94 (d, J=8.8 Hz, 2H), 4.03 (s, 3H), 3.78 (s, 3H); $^{13}$C NMR (126 MHz, Acetone-$d_6$) δ 156.05, 152.00, 143.11, 136.54 (q), 134.32, 130.53, 129.64, 128.95, 123.46, 122.29, 122.20, 114.61, 109.29, 99.98, 54.84; $^{19}$F NMR (376 MHz, Acetone-$d_6$) δ −64.32 (d, J=62.6 Hz). HRMS (ESP)=calcd for $C_{15}H_{14}F_3N_4O_2+$ [M+H]$^+$ 339.0991; found 339.1060.

Example 70. N-(3-(tert-butyl)phenyl)-5-methoxy-2-(trifluoromethyl)-3H-imidazo[4,5-b]pyridin-6-amine (2-70)

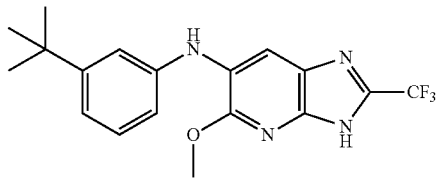 [SMILES: COc1nc2[nH]c(C(F)(F)F)nc2cc1Nc1cccc(C(C)(C)C)c1]

Using procedure 2-D, 2-70 was afforded as an orange solid (32 mg, 52%). $^1$H NMR (400 MHz, Acetone-d$_6$) δ 12.40 (s, 1H), 7.72 (s, 1H), 7.34 (s, 1H), 7.24 (t, J=7.9 Hz, 1H), 7.11 (d, J=7.8 Hz, 1H), 7.03 (d, J=6.5 Hz, 1H), 4.03 (s, 3H), 1.30 (s, 9H); $^{13}$C NMR (126 MHz, Acetone-d$_6$) δ 152.34, 137.19, 128.92, 120.46, 118.90, 118.32, 116.32, 101.92, 53.48, 34.39, 30.72; $^{19}$F NMR (376 MHz, Acetone-d$_6$) δ −64.35. HRMS (ESP)=calcd for C$_{18}$H$_{20}$F$_3$N$_4$O+ [M+H]$^+$ 365.1545; found 365.1587.

Example 71. N-(2-fluoro-3-(trifluoromethyl)phenyl)-5-methoxy-2-(trifluoromethyl)-3H-imidazo[4,5-b]pyridin-6-amine (2-71)

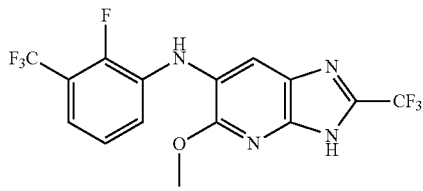 [SMILES: COc1nc2[nH]c(C(F)(F)F)nc2cc1Nc1cccc(C(F)(F)F)c1F]

Using procedure 2-D, 2-71 was afforded as a yellow solid (21 mg, 35%). $^1$H NMR (400 MHz, Acetone-d$_6$) δ 12.83 (s, 1H), 7.78 (s, 1H), 7.48 (s, 1H), 7.35−7.16 (m, 2H), 7.09 (s, 1H), 4.02 (s, 3H); $^{19}$F NMR (376 MHz, Acetone-d$_6$) δ −61.70, −61.74, −64.66. HRMS (ESI$^+$)=calcd for C$_{15}$H$_{10}$F$_7$N$_4$O+ [M+H]$^+$395.0698; found 395.0738.

Example 72. N-(3,5-bis(trifluoromethyl)phenyl)-5-methoxy-2-(trifluoromethyl)-3H-imidazo[4,5-b]pyridin-6-amine (2-72)

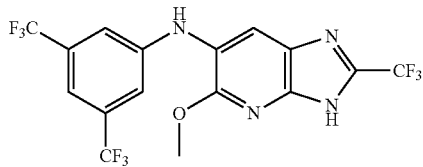 [SMILES: COc1nc2[nH]c(C(F)(F)F)nc2cc1Nc1cc(C(F)(F)F)cc(C(F)(F)F)c1]

Using procedure 2-D, 2-72 was afforded as a white solid (32 mg, 54%). $^1$H NMR (400 MHz, Acetone-d$_6$) δ 12.94 (s, 2H), 8.06 (s, 1H), 7.85 (s, 1H), 7.60 (s, 3H), 7.38 (s, 1H), 4.00 (s, 3H); $^{19}$F NMR (376 MHz, Acetone-d$_6$) δ−63.74, −64.75. HRMS (ESP)=calcd for C$_{16}$H$_{10}$F$_9$N$_4$O+ [M+H]$^+$ 445.0666; found 445.0707.

Example 73. 5-methoxy-N-(p-tolyl)-2-(trifluoromethyl)-3H-imidazo[4,5-b]pyridin-6-amine (2-73)

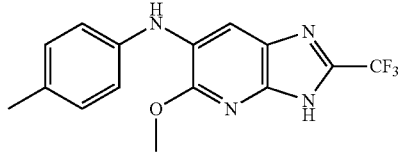 [SMILES: COc1nc2[nH]c(C(F)(F)F)nc2cc1Nc1ccc(C)cc1]

Using procedure 2-D, 2-73 was afforded as a golden-like solid (30 mg, 48%). $^1$H NMR (400 MHz, Acetone-d$_6$) δ 12.83 (s, 1H), 7.74 (s, 1H), 7.20 (d, J=9.6 Hz, 2H), 7.14 (d, J=8.2 Hz, 2H), 7.04 (s, 1H), 4.02 (s, 3H), 2.27 (s, 3H); $^{13}$C NMR (101 MHz, Acetone-d$_6$) δ 152.34, 139.12, 137.92−135.67 (m), 131.66, 130.62, 129.75 (d, J=4.2 Hz), 129.10, 127.39, 122.00, 120.31, 118.98, 111.30, 101.36, 53.30, 19.84 (d, J=4.2 Hz); $^{19}$F NMR (376 MHz, Acetone-d$_6$) δ −64.37 (d, J=61.5 Hz). HRMS (ESP)=calcd for C$_{15}$H$_{11}$F$_3$N$_4$O+ [M+H]$^+$ 323.1075; found 323.1116.

Example 74. 5-methoxy-N-(2-methyl-4-(trifluoromethoxy)phenyl)-2-(trifluoromethyl)-3H-imidazo[4,5-b]pyridin-6-amine (2-74)

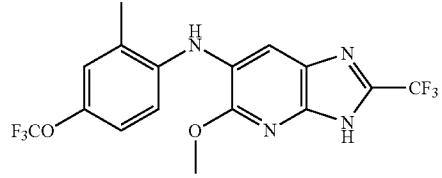 [SMILES: COc1nc2[nH]c(C(F)(F)F)nc2cc1Nc1ccc(OC(F)(F)F)cc1C]

Using procedure 2-D, 2-74 was afforded as a beige solid (8 mg, 20%). $^1$H NMR (400 MHz, Acetone-d$_6$) δ 12.88 (s, 1H), 7.48−7.35 (m, 1H), 7.31−7.08 (m, 3H), 4.05 (s, 3H), 2.31 (s, 3H); $^{13}$C NMR (101 MHz, Acetone-d$_6$) δ 154.50, 152.41, 144.84, 140.42, 139.19, 133.99, 131.55, 129.30, 127.01, 120.57, 119.44 (d, J=5.1 Hz), 114.00, 102.62, 53.57, 17.06; $^{19}$F NMR (376 MHz, Acetone-d$_6$) δ −58.77 (d, J=13.8 Hz), −64.47 (d, J=62.0 Hz). HRMS (ESI$^+$)=calcd for C$_{16}$H$_{13}$F$_6$N$_4$O$_2$+ [M+H]$^+$ 407.0898; found 407.0936.

Example 75. 5-methoxy-2-(trifluoromethyl)-N-(4-(6-(trifluoromethyl)pyridin-3-yl)phenyl)-1H-imidazo[4,5-b]pyridin-6-amine (2-75)

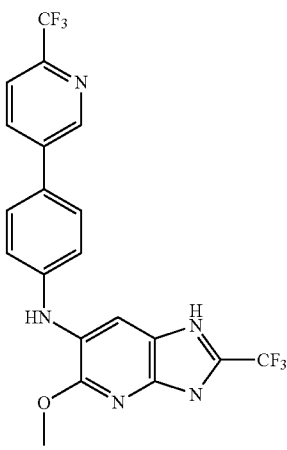

Using procedure 2-D, 2-75 was afforded as a white solid (36 mg, 62%). $^1$H NMR (500 MHz, Acetone-$d_6$) δ 12.77 (s, 1H), 9.03 (d, J=2.2 Hz, 1H), 8.28 (dd, J=8.2, 2.3 Hz, 1H), 7.96 (s, 1H), 7.88 (d, J=8.2 Hz, 1H), 7.80–7.72 (m, 2H), 7.50–7.19 (m, 3H), 4.05 (s, 3H). $^{13}$C NMR (126 MHz, Acetone-$d_6$) δ 155.18, 148.50, 145.95 (q, J=34.4 Hz), 145.08, 139.93, 138.66 (q, J=40.5 Hz), 135.43, 129.12, 128.86, 126.69, 123.03 (q, J=273.0 Hz), 121.40 (q, J=3.1 Hz), 120.78, 120.17 (q, J=271.4 Hz), 118.71, 54.46. HRMS (ESP) m/z calcd for $C_{20}H_{14}F_6N_5O^+$ (M+H)$^+$ 454.1097, found 454.1099.

OXAZOLE ANALOGS

General Procedure 4-a 6-bromopyrazin-2-amine (5.00 g 1.0 equiv.) was dissolved in dry THF (15 mL) at 0° C., NBS (20 g 2.2 equiv.) was added and stirred for 5 min. The reaction was allowed to warm to room temperature and stirred for 12 h. The solvent was evaporated under reduced pressure and the residue was extracted with ethyl acetate and sodium thiosulfate. The organic layer was then washed with water and brine. The combined organic layer was dried over sodium sulfate, filtered and concentrated. The product was purified via silica gel chromatography (ethyl acetate:hexanes).

General Procedure 4-B

In a mixture of 3,5,6-tribromopyrazin-2-amine (146 mg, 0.5 mmol), triethylamine (202 mg, 2 mmol), and catalytic amount of DMAP (5 mol %) in dry $CH_2Cl_2$ (S mL) was added 3-fluorobenzoylchloride (176 mg, 1 mmol) at room temperature. The mixture was stirred at room temperature overnight, and concentrated under reduced pressure. The residue was then dissolved in MeOH (3 mL) and $K_2CO_3$ (100 mg) was added. The mixture was stirred at 60° C. for 1 h. The mixture was then reduced down and the product purified via silica chromatography (ethyl acetate:hexanes).

General Procedure 4-C

General procedure for pyrazine-oxazole synthesis via intramolecular O-arylation: To a 10 mL sealed tube was added CuI (0.03 mmol), phenanthroline (0.1 mmol), specific benzamide (0.3 mmol), $K_3PO_4$ (1.0 mmol) and anhydrous DMF (1 mL). The tube was then sealed without inert atmosphere and heated at 83° C. for 3 h. The reaction mixture was cooled to room temperature, diluted with 10 mL water and extracted with ethyl acetate (3×20 mL). The combined organic phase was washed with water and brine, dried over anhydrous $Na_2SO_4$, and concentrated under reduced pressure. The residue was purified by silica gel chromatography (ethyl acetate:hexanes).

General Procedure 4-D

General procedure for mono/bis Buchwald Animation: Pressure vial was charged with 3,6-dibromo-2-(3-fluorophenyl)oxazolo[4,3-b]pyrazine (1 equiv.), $Pd_2dba_3$ (10 mol %), Xantphos (10 mol %), 2-fluoroaniline (2.3 equiv.), and $K_2CO_3$ (2.3 equiv.). The flask was then evacuated and backfilled with argon 3×. Dry, degassed 1,4-Dioxane (4 mL) was added through the septum and the mixture was stirred at 110° C. for 16 h. The reaction was cooled to room temperature, and the mixture was diluted with ethyl acetate, filtered through Celite, and then concentrated under reduced pressure. The residue was purified by silica gel chromotography (ethyl acetate:hexane).

Example 76. Synthesis of N5,N6-bis(2-fluorophenyl)-2-(3-fluorophenyl)oxazolo[4,5-b]pyrazine-5,6-diamine (4-1)

Step 1. Synthesis of 3,5,6-tribromopyrazin-2-amine

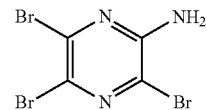

Synthesis by general procedure 4-A to yield 4-1-a yellow solid. (87% Yield). $^1$H NMR (400 MHz, Chloroform-d) δ 5.24 (s, 2H). $^{13}$C NMR (101 MHz, Chloroform-d) δ 151.18, 138.87, 125.23, 121.60.

Step 2. Synthesis of 3-fluoro-N-(3,5,6-tribromopyrazin-2-yl)benzamide

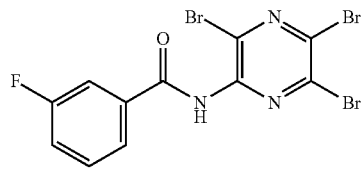 [SMILES: O=C(Nc1nc(Br)c(Br)nc1Br)c1cccc(F)c1]

Synthesis by general procedure 4-B to yield 4-1-b white solid. (57% Yield). $^1$H NMR (400 MHz, Acetone-$d_6$) δ 10.18 (s, 1H), 7.99–7.88 (m, 1H), 7.84–7.77 (m, 1H), 7.70–7.58 (m, 1H), 7.52–7.39 (m, 1H). $^{19}$F NMR (376 MHz, Acetone-$d_6$) δ −113.45 (td, J=9.1, 5.7 Hz). $^{13}$C NMR (101 MHz, DMSO-$d_6$) δ 165.58 (d, J=3.8 Hz), 162.35 (dd, J=1266.3, 246.0 Hz), 150.91, 147.92, 137.17, 134.65, 132.15 (d, J=8.4 Hz), 127.02 (d, J=8.8 Hz), 124.65 (d, J=3.4 Hz), 121.21 (d, J=21.5 Hz), 114.82 (d, J=24.4 Hz).

Step 3. Synthesis of 5,6-dibromo-2-(3-fluorophenyl)oxazolo[4,5-b]pyrazine

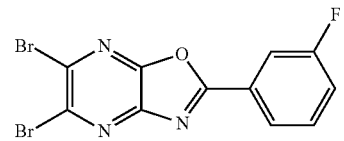 [SMILES: Fc1cccc(-c2nc3nc(Br)c(Br)nc3o2)c1]

Synthesis by general procedure 4-C to yield 4-1-c Yellow solid. (55% Yield). $^1$H NMR (400 MHz, DMSO-$d_6$) δ 8.19–8.11 (m, 1H), 8.10–8.04 (m, 1H), 7.81–7.72 (m, 1H), 7.70–7.62 (m, 1H). $^{19}$F NMR (376 MHz, DMSO-$d_6$) δ −110.77--110.97 (m, 1F). $^{13}$C NMR (101 MHz, DMSO-$d_6$) δ 170.33, 165.58 (d, J=3.8 Hz), 163.57, 161.12, 150.91, 147.92, 135.91 (d, J=252.6, 239.2 Hz), 132.15 (d, J=8.4 Hz), 127.02 (d, J=8.8 Hz), 124.65 (d, J=3.4 Hz), 121.21 (d, J=21.5 Hz), 114.82 (d, J=24.4 Hz).

Step 5. Synthesis of N5,N6-bis(2-fluorophenyl)-2-(3-fluorophenyl)oxazolo[4,5-b]pyrazine-5,6-diamine (4-1)

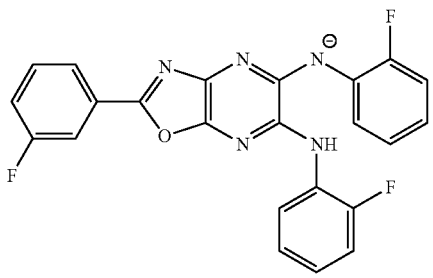 [SMILES: Fc1cccc(-c2nc3nc([N-]c4ccccc4F)c(Nc4ccccc4F)nc3o2)c1]

Synthesis by general procedure 4-D to yield 4-1 off yellow solid. (49% Yield). $^1$H NMR (500 MHz, DMSO-$d_6$) δ 8.93 (d, J=5.5 Hz, 1H), 8.57 (d, J=5.9 Hz, 1H), 7.92 (d, J=7.8 Hz, 1H), 7.86–7.79 (m, 1H), 7.76–7.66 (m, 2H), 7.65–7.56 (m, 1H), 7.42 (td, J=8.6, 2.6 Hz, 1H), 7.38–7.14 (m, 7H). $^{19}$F NMR (376 MHz, DMSO-$d_6$) δ −111.51−−111.92 (m, 1F), −120.99, −121.82. $^{13}$C NMR (126 MHz, DMSO-$d_6$) δ 162.36 (d, J=244.7 Hz), 157.57 (d, J=3.5 Hz), 155.39 (d, J=246.4 Hz), 154.96 (d, J=245.1 Hz), 145.01, 140.41, 139.51, 135.81, 131.63, 131.57, 127.16, 127.07, 125.67, 125.61, 125.40 (d, J=1.9 Hz), 124.83–124.53 (m), 124.47 (d, J=3.3 Hz), 122.49 (d, J=2.7 Hz), 118.30, 118.13, 115.94 (d, J=22.8 Hz), 115.79 (d, J=22.7 Hz), 112.86 (dt, J=27.6, 24.3, 21.9 Hz). HRMS (ESI$^-$): Calcd for $C_{23}H_{13}F_3N_5O-$ [M−H]−: 432.1078 Found: 432.1073.

HYDROXY-OXAZOLES

General Procedure 4-E

To anhydrous DMF was added sodium hydride (1.2 equiv., 60% dispersion) and allowed to stir for 1 min. To this stirred mixture was added portion wise a solution of benzyl alcohol (1.2 equiv.) in anhydrous DMF (0.1 M). The mixture was stirred at room temperature for 30 min and then a solution of 6-chloropyrazin-2-amine in anhydrous DMF (0.1 M) was added. The reaction was allowed to stir at 100° C. for 16 h and upon completion was quenched slowly with isopropanol. The reaction was then partitioned between ethyl acetate and water. The organic layer was washed with water 3×, brine 3×, and then dried over sodium sulfate. The combined organic layers were concentrated under reduced pressure and the product purified via silica gel chromatography.

General Procedure 4-F

The subsequent aniline/benzyl ether pyrazine oxazole (1.0 equiv.) was added HPLC Methanol (4 mL). The roundbottom was purged and bubbled with nitrogen gas for 5 min. After 5 min, Pd/C 10% was added under positive nitrogen pressure. The mixture was then allowed to stir under a hydrogen balloon for 1.5 h at room temperature. The reaction was then filtered through a Celite plug washing with ethyl acetate, concentrated under reduced pressure, and purified via silica gel chromatography (Methanol/DCM) to afford the product as a light sensitive highly unstable solid.

Example 77. Synthesis of 6-(benzyloxy)-N-(2-fluorophenyl)-2-(3-fluorophenyl)oxazolo[4,5-b]pyrazin-5-amine (4-2)

Step 1. Synthesis of 5-(benzyloxy)-N-(3,5-bis(trifluoromethyl)phenyl)-2-(3-fluorophenyl)oxazolo[4,5-b]pyrazin-6-amine (4-2-a)

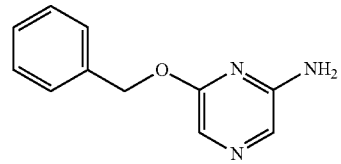 [SMILES: Nc1cncc(OCc2ccccc2)n1]

Synthesis by general procedure 4-E to yield 4-2-a Yellow solid. (19% Yield). $^1$H NMR (400 MHz, Acetone-$d_6$) δ 7.54 (s, 1H), 7.48–7.44 (m, 2H), 7.42 (t, J=0.4 Hz, 1H), 7.40–7.28 (m, 3H), 5.76 (s, 2H), 5.29 (s, 2H). $^{13}$C NMR (101 MHz, Acetone-$d_6$) δ 158.87, 154.08, 137.45, 128.28, 128.01, 127.70, 122.65, 120.40, 66.64.

Step 2. Synthesis of 6-(benzyloxy)-3,5-dibromopyrazin-2-amine (4-2-b)

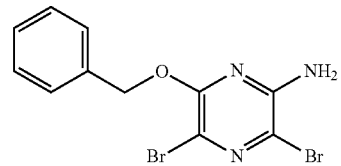 [SMILES: Nc1nc(OCc2ccccc2)c(Br)nc1Br]

Synthesis by general procedure 4-A to yield 4-2-b Yellow solid. (47% Yield). $^1$H NMR (400 MHz, Acetone-$d_6$) δ 7.53–7.46 (m, 2H), 7.43–7.31 (m, 3H), 6.29 (s, 2H), 5.37 (s, 2H). $^{13}$C NMR (101 MHz, Acetone-$d_6$) δ 156.13, 152.15, 137.32, 129.30, 128.93, 128.87, 111.11, 108.84, 69.65.

Step 3. N-(6-(benzyloxy)-3,5-dibromopyrazin-2-yl)-3-fluorobenzamide (4-2-c)

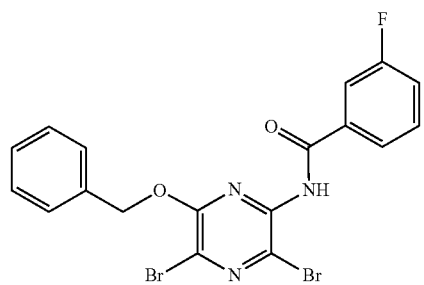 [SMILES: O=C(Nc1nc(OCc2ccccc2)c(Br)nc1Br)c1cccc(F)c1]

Synthesis by general procedure 4-B to yield 4-2-c Yellow solid. (66% Yield). $^1$H NMR (400 MHz, Chloroform-d) δ 8.34 (s, 1H), 7.72–7.62 (m, 2H), 7.57–7.49 (m, 3H), 7.43–7.29 (m, 4H), 5.47 (s, 2H). $^{19}$F NMR (376 MHz, Chloroform-d) δ −110.39−−110.50 (m, 1F).

Step 4. Synthesis of 5-(benzyloxy)-6-bromo-2-(3-fluorophenyl)oxazolo[4,5-b]pyrazine (4-2-d)

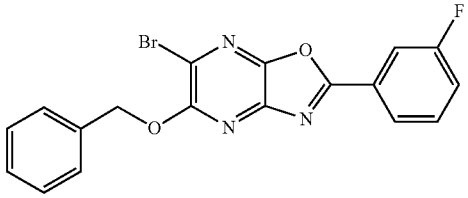 [SMILES: Fc1cccc(-c2nc3nc(OCc4ccccc4)c(Br)nc3o2)c1]

Synthesis by general procedure 4-C to yield 4-2-d Yellow solid. (9% Yield). $^1$H NMR (400 MHz, Acetone-$d_6$) δ 8.15–8.10 (m, 1H), 8.03–7.95 (m, 1H), 7.77–7.68 (m, 1H), 7.62–7.56 (m, 2H), 7.53–7.47 (m, 1H), 7.46–7.40 (m, 2H), 7.40–7.34 (m, 1H), 5.60 (s, 2H). $^{19}$F NMR (376 MHz, Acetone-$d_6$) δ −112.76 (s, 1F). $^{13}$C NMR (101 MHz, Acetone-$d_6$) δ 164.17, 162.90 (d, J=246.0 Hz), 156.02, 146.69, 144.44, 136.18, 131.64 (d, J=8.4 Hz), 128.48, 128.30 (d, J=8.7 Hz), 128.12, 127.87, 123.83 (d, J=3.3 Hz), 122.08, 119.91 (d, J=21.6 Hz), 114.25 (d, J=24.5 Hz), 69.73.

Step 5. Synthesis of 6-(benzyloxy)-N-(2-fluorophenyl)-2-(3-fluorophenyl)oxazolo[4,5-b]pyrazin-5-amine (4-2)

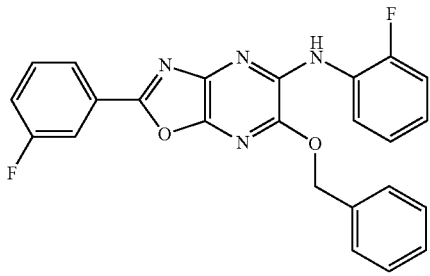 [SMILES: Fc1cccc(-c2nc3nc(Nc4ccccc4F)c(OCc4ccccc4)nc3o2)c1]

Synthesis by general procedure 4-D to 4-9 yield yellow solid. (53% Yield). $^1$H NMR (400 MHz, Chloroform-d) δ 8.63 (td, J=8.3, 1.6 Hz, 1H), 8.05–7.97 (m, 1H), 7.95–7.87 (m, 1H), 7.70 (d, J=3.8 Hz, 1H), 7.60–7.34 (m, 6H), 7.26–7.11 (m, 3H), 7.08–7.00 (m, 1H), 5.65 (s, 2H). $^{19}$F NMR (376 MHz, Chloroform-d) δ −108.22–−116.82 (m, 1F), −131.72 (ddd, J=12.6, 8.1, 4.4 Hz, 1F). $^{13}$C NMR (101 MHz, Chloroform-d) δ 164.36, 163.11 (d, J=246.8 Hz), 159.11 (d, J=3.5 Hz), 152.84 (d, J=243.5 Hz), 147.50, 145.98, 138.83, 135.83, 134.87, 130.83 (d, J=8.4 Hz), 129.30 (d, J=8.8 Hz), 128.87, 128.69, 128.53, 127.49 (d, J=10.0 Hz), 124.79 (d, J=3.9 Hz), 123.22 (d, J=7.7 Hz), 122.70 (d, J=3.4 Hz), 120.26, 118.37 (d, J=21.5 Hz), 114.95 (d, J=19.1 Hz), 113.90 (d, J=24.5 Hz), 69.72. HRMS (ESI$^+$): Calcd for $C_{24}H_{17}F_2N_4O_2$+ [M+H]+: 431.1314 Found: 431.1316.

Example 78. 2-(3-fluorophenyl)-6-((2-fluorophenyl)amino)oxazolo[4,5-b]pyrazin-5-ol (4-3)

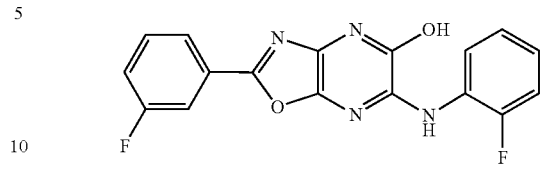

Synthesis by general procedure 4-F to yield 4-10 off yellow solid. (70% Yield). $^1$H NMR (500 MHz, DMSO-$d_6$) δ 13.35 (s, 1H), 9.00 (s, 1H), 8.17 (t, J=8.0 Hz, 1H), 7.84 (d, J=7.8 Hz, 1H), 7.73 (d, J=9.7 Hz, 1H), 7.60 (q, J=7.4 Hz, 1H), 7.33 (ddd, J=37.0, 15.6, 8.1 Hz, 3H), 7.19 (q, J=7.1 Hz, 1H). $^{19}$F NMR (376 MHz, DMSO-$d_6$) δ −111.72 (td, J=9.4, 6.1 Hz, 1F). $^{13}$C NMR (126 MHz, DMSO-$d_6$) δ 162.40 (d, J=244.5 Hz), 153.86 (d, J=244.8 Hz), 131.64, 131.57 (d, J=10.3 Hz), 128.73 (d, J=8.9 Hz), 126.44 (d, J=10.9 Hz), 125.08–124.80 (m), 124.71 (d, J=4.2 Hz), 122.88–122.58 (m), 121.75 (d, J=3.5 Hz), 117.50 (dq, J=29.7, 21.6, 21.2, 20.9 Hz), 115.50, 115.34 (tdd, J=21.8, 19.1, 11.6 Hz), 112.08 (d, J=24.8 Hz). HRMS (ESI$^-$): Calcd for $C_{17}H_9F_2N_4O_2$— [M−H]−: 339.0699 Found: 339.0695.

Example 79. 5-(benzyloxy)-N-(3,5-bis(trifluoromethyl)phenyl)-2-(3-fluorophenyl)oxazolo[4,5-b]pyrazin-6-amine (4-4)

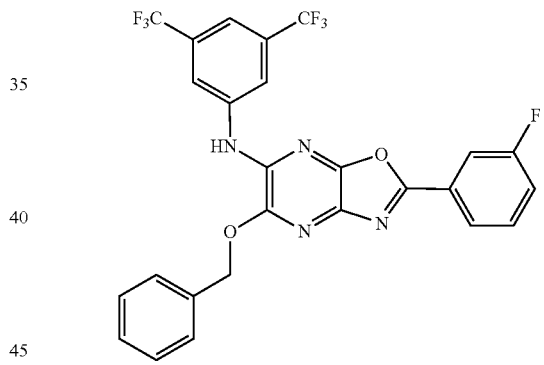

Synthesis by general procedure 4-D to yield 4-3 off yellow solid. (32% Yield). $^1$H NMR (400 MHz, Chloroform-d) δ 8.26 (s, 2H), 8.04 (d, J=7.8 Hz, 1H), 7.94 (dt, J=9.3, 2.1 Hz, 1H), 7.62-7.36 (m, 7H), 7.32–7.06 (m, 4H), 5.63 (s, 2H). $^{19}$F NMR (376 MHz, Chloroform-d) δ −62.94.

Example 80. Synthesis of 6-((3,5-bis(trifluoromethyl)phenyl)amino)-2-(3-fluorophenyl)oxazolo[4,5-b]pyrazin-5-ol (4-5)

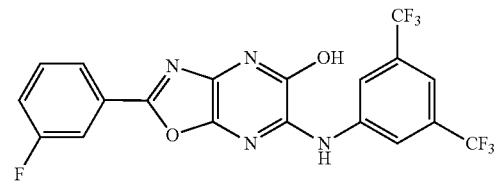 [SMILES: Oc1nc2nc(-c3cccc(F)c3)oc2nc1Nc1cc(C(F)(F)F)cc(C(F)(F)F)c1]

Synthesis by general procedure 4-F to yield 4-12 off-yellow solid. (32% Yield). $^1$H NMR (400 MHz, Acetone-$d_6$) δ 9.50 (s, 1H), 8.82 (dq, J=1.4, 0.7 Hz, 2H), 7.93 (ddd, J=7.8, 1.5, 0.9 Hz, 1H), 7.81–7.74 (m, 1H), 7.73–7.70 (m, 1H), 7.67–7.56 (m, 1H), 7.40–7.25 (m, 1H). $^{19}$F NMR (376 MHz, Acetone-$d_6$) δ −63.50 (s, 6F), −113.31--113.39 (m, 1F).

Starting Materials

Example 81. Preparation of Starting Materials for Examples 1-60

General Procedures for the Preparation of Starting Material Compounds by Nucleophilic Aromatic Substitution General Procedure 1-C. 5-Chloro-6-alkoxy-[1,2,5]oxadiazolo[3,4-b]pyrazine was taken and dissolved in anhydrous THF (0.1 M-0.2 M) and added to a sealed tube under argon atmosphere. The corresponding aniline (2.2 equiv.) was added and the reaction was stirred at 65° C. for 16 h. The solvent was then removed under reduced pressure and purified by chromatography on $SiO_2$ with a solvent system of EtOAc/hexanes to yield the desired product, a 5-amino-6-alkoxy-[1,2,5]oxadiazolo[3,4-b]pyrazine. Scheme 3 illustrates general procedure 1-C.

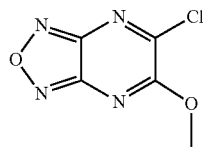

Compound 1-138. Synthesis of 5-chloro-6-methoxy-[1,2,5]oxadiazolo[3,4-b]pyrazine (1-138)

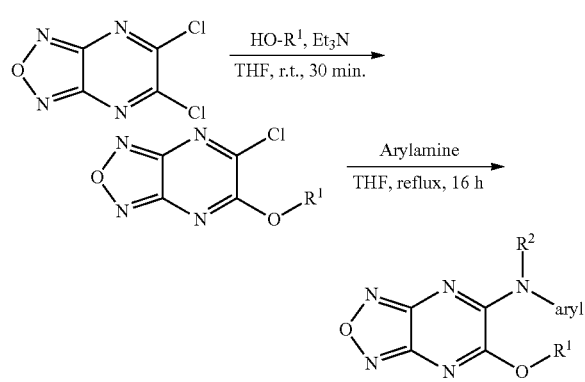

Scheme 3.

5,6-Dichloro-[1,2,5]oxadiazolo[3,4-b]pyrazine (1-2) (2.00 g) was dissolved in anhydrous THF (25 mL) and $Et_3N$ (1.46 mL, 1 equiv.) was added. The solution was mixed and MeOH (0.9 equiv.) was added dropwise over a few minutes. The solution evolved into a slurry and was allowed to stir at room temperature for 30 min. The solvent was then removed under reduced pressure and purified by chromatography on $SiO_2$ (gradient: 5-15% EtOAc/hexanes) to yield 1-138 (68%) as a colorless solid.

Compound 1-139. Synthesis of N-(3,5-bis(trifluoromethyl)phenyl)-6-methoxy-[1,2,5]oxadiazolo[3,4-b]pyrazin-5-amine (1-139)

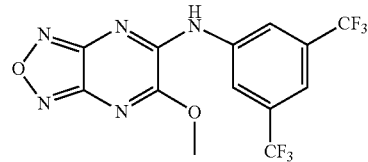 [SMILES: COc1nc2nonc2nc1Nc1cc(C(F)(F)F)cc(C(F)(F)F)c1]

Compound 1-139 was synthesized by procedure 1-C using 1-138 to yield 1-139 in 89% as an off-white solid: $^1$H NMR (500 MHz, Acetone-$d_6$) δ 10.02 (s, 1H), 8.76 (d, J=1.5 Hz, 2H), 7.93-7.75 (m, 1H), 4.27 (s, 3H); $^{19}$F NMR (376 MHz, Acetone-$d_6$) δ −63.57 (s 6F); $^{13}$C NMR (126 MHz, Acetone-$d_6$) δ 156.22, 151.28, 150.61, 147.92, 140.78, 132.63 (q, J=33.3 Hz), 124.30 (d, J=272.7 Hz), 122.30 (q, J=4.7 Hz), 118.56 (h, J=4.2 Hz), 56.75; HRMS (ESI$^+$) m/z calc'd. for $C_{13}H_8F_6N_5O_2$ [M+H]$^+$ 380.0577, found 380.0578.

Compound 1-140. Synthesis of N-(2-fluoro-3-(trifluoromethyl)phenyl)-6-methoxy-[1.2.5]oxadiazolo[3,4-b]pyrazin-5-amine (1-140)

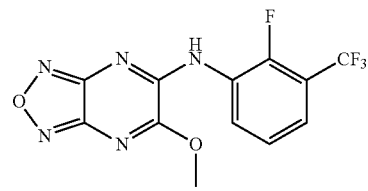 [SMILES: COc1nc2nonc2nc1Nc1cccc(C(F)(F)F)c1F]

Compound 1-140 was synthesized by procedure 1-C using 1-138 to yield 1-140 in 80% as a beige solid: $^1$H NMR (400 MHz, Acetone-$d_6$) δ 9.38–9.25 (m, 1H), 8.54–8.42 (m, 1H), 7.66 (dddd, J=8.2, 6.6, 1.7, 0.8 Hz, 1H), 7.53 (tt, J=8.0, 1.1 Hz, 1H), 4.30 (s, 3H); $^{19}$F NMR (376 MHz, Acetone-$d_6$) δ −61.75 (d, J=13.0 Hz 3F), −126.91--127.08 (m 1F); $^{13}$C NMR (101 MHz, Acetone-$d_6$) δ 156.23, 152.35 (dq, J=256 Hz, 2.4, Hz), 151.59, 150.82, 148.32, 130.95 (d, J=1.8 Hz), 127.41 (d, J=10.6 Hz), 125.69 (d, J=5.0 Hz), 124.68 (q, J=4.8, 1.3 Hz), 123.58 (q, J=272.9 Hz), 56.81; HRMS (ESI$^+$) m/z calc'd. for $C_{12}H_8F_4N_5O_2$ [M+H]$^+$ 330.0609, found 330.0655.

Compound 1-141. Synthesis of 6-methoxy-N-(3-(trifluoromethoxy)phenyl)-[1,2,5]oxadiazolo[3,4-b]pyrazin-5-amine (1-141)

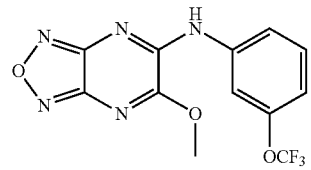 [SMILES: COc1nc2nonc2nc1Nc1cccc(OC(F)(F)F)c1]

Compound 1-141 was synthesized by procedure 1-C using 1-138 to yield 1-141 in 95% as a yellow solid: ¹H NMR (500 MHz, Acetone-d₆) δ 9.73 (s, 1H), 8.17 (td, J=2.2, 1.1 Hz, 1H), 8.08–7.95 (m, 1H), 7.56 (t, J=8.2 Hz, 1H), 7.17 (ddt, J=8.3, 2.3, 1.1 Hz, 1H), 4.23 (s, 3H); ¹⁹F NMR (376 MHz, Acetone-d₆) δ −58.50 (s 3F); ¹³C NMR (126 MHz, Acetone-d₆) δ 156.30, 151.57, 150.54, 149.99 (q, J=2.2 Hz), 147.70, 140.38, 131.22, 121.44 (q, J=257.9 Hz), 120.99, 117.84, 114.87, 56.56; HRMS (ESI⁺) m/z calc'd. for C₁₂H₉F₃N₅O₃ [M+H]⁺ 328.0652, found 328.0666.

Compound 1-142. Synthesis of 6-methoxy-N-(2-methyl-5-(trifluoromethyl)phenyl)-[1,2,5]oxadiazolo[3,4-b]pyrazin-5-amine (1-142)

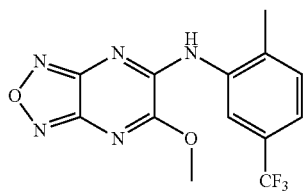 [SMILES: COc1nc2nonc2nc1Nc1cc(C(F)(F)F)ccc1C]

Compound 1-142 was synthesized by procedure 1-C using 1-138 to yield 1-142 in 93% as an off-white solid: ¹H NMR (500 MHz, Acetone-d₆) δ 9.28 (s, 1H), 8.09 (s, 1H), 7.58 (d, J=1.2 Hz, 2H), 4.28 (s, 3H), 2.45 (d, J=1.1 Hz, 3H); ¹⁹F NMR (376 MHz, Acetone-d₆) δ −62.80 (s 3F); ¹³C NMR (126 MHz, Acetone-d₆) δ 156.55, 151.95, 150.83, 148.91, 139.26 (d, $J_{CF}$=1.6 Hz), 137.13, 132.43, 129.07 (d, $J_{CF}$=32.4 Hz), 125.50 (d, $J_{CF}$=272.0 Hz), 124.08 (q, $J_{CF}$=4.0 Hz), 123.60 (q, $J_{CF}$=4.3 Hz), 56.65, 18.17; HRMS (ESI⁺) m/z calc'd. for C₁₃H₁₁F₃N₅O₂ [M+H]⁺ 326.0859, found 326.0906.

Compound 1-143. Synthesis of N-(3-fluorophenyl)-6-methoxy-[1,2,5]oxadiazolo[3,4-b]pyrazin-5-amine (1-143)

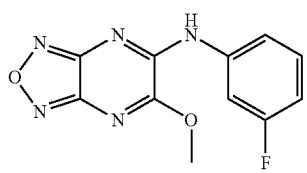 [SMILES: COc1nc2nonc2nc1Nc1cccc(F)c1]

Compound 1-143 was synthesized by procedure 1-C using 1-138 to yield 1-143 in 74% as a yellow solid: ¹H NMR (500 MHz, Acetone-d₆) δ 9.64 (s, 1H), 8.03 (dt, J=11.5, 2.3 Hz, 1H), 7.79–7.70 (m, 1H), 7.44 (td, J=8.3, 6.7 Hz, 1H), 6.97 (tt, J=8.5, 1.6 Hz, 1H), 4.21 (s, 3H); ¹⁹F NMR (376 MHz, Acetone-d₆) δ −113.03−−113.17 (m, 1F); ¹³C NMR (126 MHz, Acetone-d₆) δ 163.47 (d, $J_{CF}$=242.0 Hz), 156.24, 151.58, 150.46, 147.54, 140.37 (d, $J_{CF}$=11.3 Hz), 131.14 (d, $J_{CF}$=9.6 Hz), 118.07 (d, $J_{CF}$=3.5 Hz), 112.23 (d, $J_{CF}$=21.5 Hz), 109.28 (d, $J_{CF}$=27.1 Hz), 56.52; HRMS (ESI⁺) m/z calc'd. for C₁₁H₉FN₅O₂ [M+H]⁺ 262.0735, found 262.0774.

Synthesis of 6-methoxy-N-(p-tolyl)-[1,2,5]oxadiazolo[3,4-b]pyrazin-5-amine (1-144)

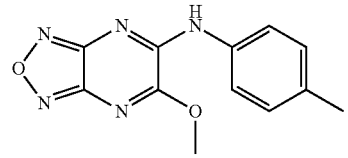 [SMILES: COc1nc2nonc2nc1Nc1ccc(C)cc1]

Compound 1-144 was synthesized by procedure 1-C using 1-138 to yield 1-144 in 89% as a yellow solid: ¹H NMR (500 MHz, Acetone-d₆) δ 8.85 (s, 1H), 7.87–7.78 (m, 2H), 7.42–7.29 (m, 2H), 4.31 (s, 3H), 2.45 (s, 3H); ¹³C NMR (126 MHz, Acetone-d₆) δ 185.23, 180.64, 179.30, 176.38, 164.91, 164.16, 158.88, 151.37, 146.81, 85.25, 49.52; HRMS (ESI⁺) m/z calc'd. for C₁₂H₁₂N₅O₂ [M+H]⁺ 258.0986, found 258.0990.

Compound 1-145. Synthesis of 6-methoxy-N-(4-methoxyphenyl)-[1,2,5]oxadiazolo[3,4-b]pyrazin-5-amine (1-145)

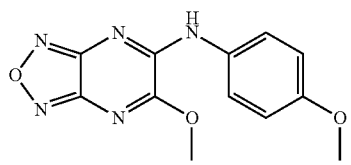 [SMILES: COc1ccc(Nc2nc3nonc3nc2OC)cc1]

Compound 1-145 was synthesized by procedure 1-C using 1-138 to yield 1-145 in 90% as a yellow solid: ¹H NMR (500 MHz, Acetone-d₆) δ 8.83 (s, 1H), 7.88–7.81 (m, 2H), 7.13–7.06 (m, 2H), 4.31 (s, 3H), 3.92 (s, 3H); ¹³C NMR (126 MHz, Acetone-d₆) δ 186.85, 185.32, 180.74, 179.36, 176.41, 159.58, 153.17, 146.82, 143.53, 85.23, 84.64; HRMS (ESI⁺) m/z calc'd. for C₁₂H₁₂N₅O₃ [M+H]⁺ 274.0935, found 274.0940.

Compound 1-146. Synthesis of 6-methoxy-N-phenyl-[1,2,5]oxadiazolo[3,4-b]pyrazin-5-amine (1-146)

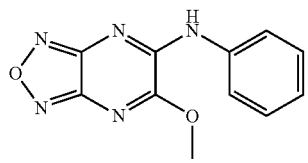 [SMILES: COc1nc2nonc2nc1Nc1ccccc1]

Compound 1-146 was synthesized by procedure 1-C using 1-138 to yield 1-146 in 94% as a beige solid: ¹H NMR (500 MHz, Acetone-d₆) δ 8.90 (s, 1H), 8.00–7.94 (m, 2H), 7.59–7.51 (m, 2H), 7.38–7.32 (m, 1H), 4.32 (s, 3H); carbon; HRMS (ESI⁺) m/z calc'd. for C₁₁H₁₀N₅O₂ [M+H]⁺ 244.0829, found 244.0834.

Compound 1-147. Synthesis of N-(2,3-difluorophenyl)-6-methoxy-[1,2,5]oxadiazolo[3,4-b]pyrazin-5-amine (1-147)

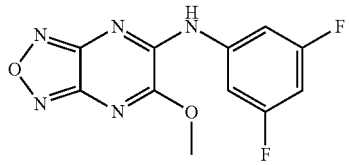 [SMILES: COc1nc2nonc2nc1Nc1cc(F)cc(F)c1]

Compound 1-147 was synthesized by procedure 1-C using 1-138 to yield 1-147 in 90% as an off-white solid: $^1$H NMR (500 MHz, Acetone-d$_6$) δ 9.78 (s, 1H), 7.90–7.76 (m, 2H), 6.87 (tt, J=9.1, 2.3 Hz, 1H), 4.23 (s, 3H); $^{19}$F NMR (376 MHz, Acetone-d$_6$) δ −110.31−−110.43 (m 2F); $^{13}$C NMR (126 MHz, Acetone-d$_6$) δ 163.85 (dd, J=244.2, 14.9 Hz), 156.20, 151.42, 150.52, 147.71, 141.32 (t, J=13.8 Hz), 105.62–104.84 (m), 100.62 (t, J=26.2 Hz), 56.62; HRMS (ESI$^+$) m/z calc'd. for C$_{11}$H$_8$F$_2$N$_5$O$_2$ [M+H]$^+$ 280.0641, found 280.0645.

Compound 1-148. Synthesis of N-(3,5-difluorophenyl)-6-methoxy-[1,2,5]oxadiazolo[3,4-b]pyrazin-5-amine (1-148)

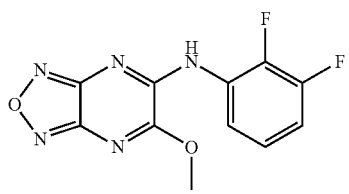 [SMILES: COc1nc2nonc2nc1Nc1cccc(F)c1F]

Compound 1-148 was synthesized by procedure 1-C using 1-138 to yield 1-148 in 98% as an off-white solid: $^1$H NMR (500 MHz, Acetone-d$_6$) δ 9.09 (s, 1H), 7.93–7.85 (m, 1H), 7.34–7.19 (m, 2H), 4.27 (s, 3H); $^{19}$F NMR (376 MHz, Acetone-d$_6$) δ −139.41−−139.55 (m, 1F), −148.52−−148.79 (m, 1F); $^{13}$C NMR (126 MHz, Acetone-d$_6$) δ 156.24, 151.66, 151.41 (dd, J=245.7, 11.2 Hz), 150.80, 148.32, 144.85 (dd, J=249.2, 14.4 Hz), 127.59 (dd, J=8.7, 1.9 Hz), 125.11 (dd, J=7.9, 5.0 Hz), 121.81 (d, J=3.5 Hz), 117.78, 115.38 (d, J=17.1 Hz), 56.75; HRMS (ESI$^+$) m/z calc'd. for C$_{11}$H$_8$N$_5$O$_2$ [M+H]$^+$ 280.0641, found 280.0654.

Compound 1-149. Synthesis of N-(4-chlorophenyl)-6-methoxy-[1,2,5]oxadiazolo[3,4-b]pyrazin-5-amine (1-149)

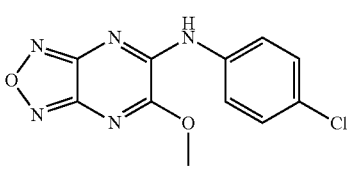 [SMILES: COc1nc2nonc2nc1Nc1ccc(Cl)cc1]

Compound 1-149 was synthesized by procedure 1-C using 1-138 to yield 1-149 in 96% as a beige solid: $^1$H NMR (500 MHz, Acetone-d$_6$) δ 9.62 (s, 1H), 8.11–8.00 (m, 2H), 7.53–7.40 (m, 2H), 4.22 (s, 3H); $^{13}$C NMR (126 MHz, Acetone-d$_6$) δ 156.37, 151.72, 150.56, 147.58, 137.61, 130.37, 129.62, 124.03, 56.50; HRMS (ESI$^+$) m/z calc'd. for C$_{11}$H$_9$ClN$_5$O$_2$ [M+H]$^+$ 278.0439, found 278.0455.

Compound 1-151. Synthesis of N-(3-fluoro-4-(trifluoromethoxy)phenyl)-6-methoxy-[1,2,5]oxadiazolo[3,4-b]pyrazin-5-amine (1-151)

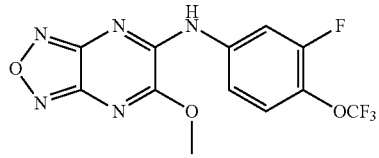 [SMILES: COc1nc2nonc2nc1Nc1ccc(OC(F)(F)F)c(F)c1]

Compound 1-151 was synthesized by procedure 1-C using 1-138 to yield 1-151 in 97% as a beige solid: $^1$H NMR (500 MHz, Acetone-d$_6$) δ 9.83 (s, 1H), 8.42–8.11 (m, 1H), 8.05–7.69 (m, 1H), 7.67–7.32 (m, 1H), 4.23 (s, 3H); $^{19}$F NMR (376 MHz, Acetone-d$_6$) δ −59.87 (d, J=5.2 Hz, 3F), −128.91 (s, 1F); $^{13}$C NMR (126 MHz, Acetone-d$_6$) δ 156.28 (d, J$_{CF}$=4.7 Hz), 154.88 (d, J$_{CF}$=248.8 Hz), 151.48 (d, J$_{CF}$=3.6 Hz), 150.58 (d, J$_{CF}$=3.7 Hz), 147.70 (d, J$_{CF}$=5.4 Hz), 139.50–139.12 (m), 133.31–132.85 (m), 125.10 (d, J$_{CF}$=2.4 Hz), 121.48 (d, J$_{CF}$=256.8 Hz), 118.81, 111.56–110.66 (m), 56.61; HRMS (ESI$^+$) m/z calc'd. for C$_{12}$H$_8$F$_4$N$_5$O$_3$ [M+H]$^+$ 346.0558, found 346.0568.

Compound 1-152. Synthesis of 6-methoxy-N-(naphthalen-2-yl)-[1,2,5]oxadiazolo[3,4-b]pyrazin-5-amine (1-152)

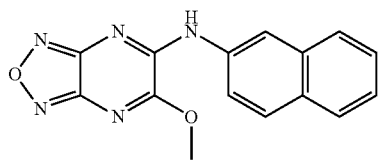 [SMILES: COc1nc2nonc2nc1Nc1ccc2ccccc2c1]

Compound 1-152 was synthesized by procedure 1-C using 1-138 to yield 1-152 in 97% as a yellow solid: $^1$H NMR (400 MHz, Acetone-d$_6$) δ 9.69 (s, 1H), 8.81–8.77 (m, 1H), 8.00–7.86 (m, 4H), 7.58–7.44 (m, 2H), 4.26 (app d, J=0.5 Hz, 3H); $^{13}$C NMR (101 MHz, Acetone-d$_6$) δ 156.51, 151.91, 150.62, 147.68, 136.27, 134.59, 131.98, 129.40, 128.70, 128.47, 127.54, 126.42, 122.24, 119.47, 56.50; HRMS (ESI$^+$) m/z calc'd. for C$_{15}$H$_{12}$N$_5$O$_2$ [M+H]$^+$ 294.0986, found 294.0992.

Compound 1-153. Synthesis of N-(4-ethylphenyl)-6-methoxy-[1,2,5]oxadiazolo[3,4-b]pyrazin-5-amine (1-153)

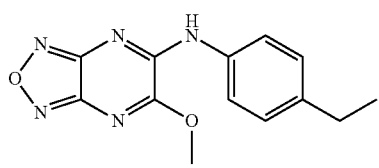 [SMILES: CCc1ccc(Nc2nc3nonc3nc2OC)cc1]

Compound 1-153 was synthesized by procedure 1-C using 1-138 to yield 1-153 in 57% as a yellow solid: $^1$H NMR (500 MHz, Acetone-d$_6$) δ 9.46 (s, 1H), 7.96–7.85 (m, 2H), 7.36–7.20 (m, 2H), 4.23 (s, 3H), 2.66 (q, J=7.6 Hz, 2H), 1.24 (t, J=7.6 Hz, 3H); $^{13}$C NMR (126 MHz, Acetone-d$_6$) δ 156.43, 151.94, 150.52, 147.46, 142.04, 136.31, 128.93, 122.60, 56.41, 28.90, 16.01; HRMS (ESI$^+$) m/z calc'd. for C$_{13}$H$_{14}$N$_5$O$_2$ [M+H]$^+$ 272.1142, found 272.1158.

Compound 1-154. N-(3-fluoro-4-pentylphenyl)-6-methoxy-[1,2,5]oxadiazolo[3,4-b]pyrazin-5-amine (1-154)

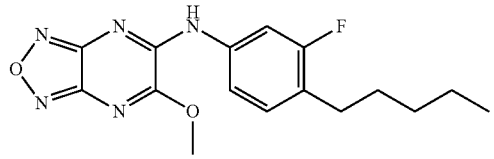 [SMILES: CCCCCc1ccc(Nc2nc3nonc3nc2OC)cc1F]

Compound 1-154 was synthesized by procedure 1-C using 1-138 to yield 1-154 in 68% as a yellow solid: $^1$H NMR (500 MHz, Acetone-d$_6$) δ 9.61 (s, 1H), 7.99 (dd, J=12.4, 2.2 Hz, 1H), 7.71 (dd, J=8.3, 2.2 Hz, 1H), 7.33 (t, J=8.5 Hz, 1H), 4.24 (s, 3H), 2.66 (t, J=7.7 Hz, 2H), 1.72–1.53 (m, 2H), 1.43–1.31 (m, 4H), 1.00–0.88 (m, 3H); $^{19}$F NMR (376 MHz, Acetone-d$_6$) δ −118.57−−118.67 (m, 1F); $^{13}$C NMR (126 MHz, Acetone-d$_6$) δ 161.43 (d, J$_{CF}$=241.7 Hz), 156.34, 151.73, 150.52, 147.50, 138.02 (d, J$_{CF}$=11.3 Hz), 131.57 (d, J$_{CF}$=6.6 Hz), 126.77 (d, J$_{CF}$=16.7 Hz), 118.06 (d, J$_{CF}$=3.6 Hz), 109.32 (d, J$_{CF}$=28.3 Hz), 56.49, 32.17, 29.53, 29.10, 23.10, 14.27; HRMS (ESI$^+$) m/z calc'd. for C$_{16}$H$_{19}$FN$_5$O$_2$ [M+H]$^+$ 332.1517, found 332.1533.

Compound 1-155. Synthesis of N-(2-fluoro-4-pentylphenyl)-6-methoxy-[1,2,5]oxadiazolo[3,4-b]pyrazin-5-amine (1-155)

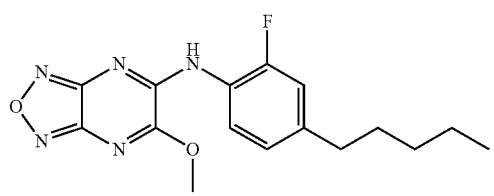 [SMILES: CCCCCc1ccc(Nc2nc3nonc3nc2OC)c(F)c1]

Compound 1-155 was synthesized by procedure 1-C using 1-138 to yield 1-155 in 90% as a yellow solid: $^1$H NMR (500 MHz, Acetone-d$_6$) δ 9.08 (s, 1H), 8.08 (t, J=8.3 Hz, 1H), 7.25–7.03 (m, 2H), 4.28 (s, 3H), 2.74–2.59 (m, 2H), 1.74–1.51 (m, 2H), 1.46–1.19 (m, 4H), 0.91 (t, J=6.8 Hz, 3H); $^{19}$F NMR (376 MHz, Acetone-d$_6$) δ −126.34 (dd, J=11.6, 8.2 Hz); $^{13}$C NMR (126 MHz, Acetone-d$_6$) δ 156.25, 155.81 (d, J$_{CF}$=246.6 Hz), 151.82, 150.68, 148.02, 143.68 (d, J$_{CF}$=7.3 Hz), 125.90 (d, J$_{CF}$=1.4 Hz), 125.16 (d, J$_{CF}$=3.6 Hz), 123.28 (d, J$_{CF}$=11.7 Hz), 116.08 (d, J$_{CF}$=19.2 Hz), 56.68, 35.80 (d, J$_{CF}$=1.8 Hz), 32.08, 31.65, 23.11, 14.29; HRMS (ESI$^+$) m/z calc'd. for C$_{16}$H$_{19}$FN$_5$O$_2$ [M+H]$^+$ 332.1517, found 332.1527.

Compound 1-156. Synthesis of 6-methoxy-N-(4-(trifluoromethoxy)phenyl)-[1,2,5]oxadiazolo[3,4-b]pyrazin-5-amine (1-156)

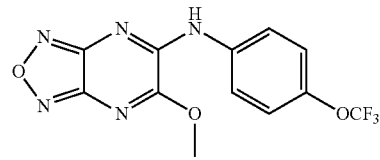 [SMILES: COc1nc2nonc2nc1Nc1ccc(OC(F)(F)F)cc1]

Compound 1-156 was synthesized by procedure 1-C using 1-138 to yield 1-156 in 66% as a yellow solid: $^1$H NMR (400 MHz, Acetone-d$_6$) δ 9.70 (brs, 1H), 8.18–8.13 (m, 2H), 7.44–7.39 (m, 2H), 4.23 (s, 3H); $^{13}$C NMR (100 MHz, Acetone-d$_6$) δ 156.48, 151.79, 150.68, 147.77, 146.48 (q, J=1.9 Hz), 137.88, 124.16, 122.51 (q, J=255.13 Hz), 56.61; $^{19}$F NMR (376 MHz, Acetone-d$_6$) δ −58.78 (s, 3F); HRMS (ESI): Calc'd. for C$_{12}$H$_9$F$_3$N$_5$O$_3$$^+$ [M+H]$^+$: 328.0652, Observed: 328.0667.

Compound 1-157. Synthesis of N-(4-butylphenyl)-6-methoxy-[1,2,5]oxadiazolo[3,4-b]pyrazin-5-amine (1-157)

Compound 1-157 was synthesized by procedure 1-C using 1-138 to yield 1-157 in 66% as a yellow solid: $^1$H NMR (400 MHz, Acetone-d$_6$) δ 9.47 (brs, 1H), 7.94–7.90 (m, 2H), 7.30–7.25 (m, 2H), 4.22 (s, 3H), 2.63 (t, 2H, J=7.6 Hz), 1.61 (q, 2H, J=7.8 Hz), 1.37 (h, 2H, J=7.8), 0.93 (t, 3H, J=7.3 Hz); $^{13}$C NMR (100 MHz, Acetone-d$_6$) δ 155.59, 151.08, 149.66, 146.61, 139.77, 135.44, 128.61, 121.65, 55.52, 34.78, 33.58, 22.05, 13.29; HRMS (ESI): Calc'd. for C$_{15}$H$_{18}$N$_5$O$_2$$^+$ [M+H]$^+$: 300.1455, Observed: 300.1443.

Compound 1-158. Synthesis of N-(-fluoro-5-(trifluoromethyl)phenyl)-6-methoxy-[1,2,5]oxadiazolo[3,4-b]pyrazin-5-amine (1-158)

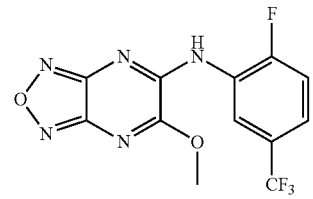 [SMILES: COc1nc2nonc2nc1Nc1cc(C(F)(F)F)ccc1F]

Compound 1-158 was synthesized by procedure 1-C using 1-138 to yield 1-158 in 83% as a yellow solid: $^1$H NMR (400 MHz, Acetone-d$_6$) δ 9.26 (brs, 1H), 8.64 (d, 1H, J=7.0 Hz), 7.74–7.68 (m, 1H), 7.61–7.53 (m, 1H), 4.30 (s, 3H); $^{13}$C NMR (100 MHz, Acetone-d$_6$) δ 157.93 (d, J=254

Hz), 156.26, 151.58, 150.85, 148.27, 127.34 (q, J=34 Hz), 127.08 (d, J=12 Hz), 125.17 (h, J=5 Hz), 124.76 (q, J=272 Hz), 123.37 (m, J=2 Hz), 117.70 (d, J=21 Hz), 56.91; $^{19}$F NMR (376 MHz, Acetone-d$_6$) δ −62.62 (s, 3F), −119.21−−119.31 (m, 1F); HRMS (ESI): Calc'd. for $C_{12}H_8F_4N_5O_2^+$ [M+H]$^+$: 330.0609, Observed: 330.0611.

Compound 1-159. Synthesis of N-(2-fluorophenyl)-6-methoxy-[1,2,5]oxadiazolo[3,4-b]pyrazin-5-amine (1-159)

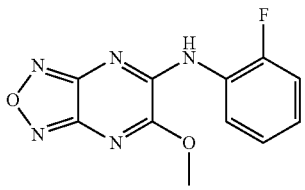 [SMILES: COc1nc2nonc2nc1Nc1ccccc1F]

Compound 1-159 was synthesized by procedure 1-C using 1-138 to yield 1-159 in 95% as a yellow solid: $^1$H NMR (400 MHz, Acetone-d$_6$) δ 9.14 (brs, 1H), 8.26−8.18 (m, 1H), 7.38−7.26 (m, 3H), 4.29 (s, 3H); $^{13}$C NMR (100 MHz, Acetone-d$_6$) δ 156.44 (d, J=246 Hz), 156.11, 151.93, 150.88, 148.28, 128.10 (d, J=8 Hz), 126.31, 126.12 (d, J=11 Hz), 125.55 (d, J=4 Hz), 116.53 (d, J=20 Hz), 56.85; $^{19}$F NMR (376 MHz, Acetone-d$_6$) δ −125.90−−126.04 (m, 1F); HRMS (ESI): Calc'd. for $C_{11}H_9FN_5O_2^+$[M+H]$^+$: 262.0735, Observed: 262.0741.

Compound 1-160. Synthesis of 6-methoxy-N-(2-(trifluoromethyl)phenyl)-[1,2,5]oxadiazolo[3,4-b]pyrazin-5-amine (1-160)

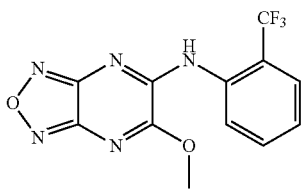 [SMILES: COc1nc2nonc2nc1Nc1ccccc1C(F)(F)F]

Compound 1-160 was synthesized by procedure 1-C using 1-138 to yield 1-160 in 90% as a yellow solid: $^1$H NMR (400 MHz, Acetone-d$_6$) δ 9.15 (brs, 1H), 8.14 (d, 1H, J=8.2 Hz), 7.89−7.78 (m, 1H), 7.60−7.53 (m, 1H), 4.31 (s, 3H); $^{13}$C NMR (100 MHz, Acetone-d$_6$) δ 156.34, 151.83, 150.85, 149.32, 135.75 (q, J=2 Hz), 134.27 (q, J=1 Hz), 129.33, 128.12, 127.60 (q, J=5 Hz), 125.39 (q, J=30 Hz), 124.86 (q, J=274 Hz), 56.97; $^{19}$F NMR (376 MHz, Acetone-d$_6$) δ −61.16 (s, 1F); HRMS (ESI): Calc'd. for $C_{12}H_9F_3N_5O_2^+$ [M+H]$^+$: 312.0703, Observed: 312.0700.

Compound 1-161. Synthesis of N-([1,1'-biphenyl]-4-yl)-6-methoxy-[1,2,5]oxadiazolo[3,4-b]pyrazin-5-amine (1-161)

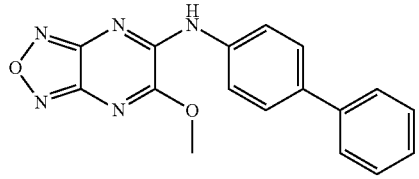 [SMILES: COc1nc2nonc2nc1Nc1ccc(-c2ccccc2)cc1]

Compound 1-161 was synthesized by procedure 1-C using 1-138 to yield 1-161 in 70% as a yellow solid: $^1$H NMR (400 MHz, Acetone-d$_6$) δ 9.63 (brs, 1H), 8.15 (d, 2H, J=8.6 Hz), 7.76 (d, 2H, J=8.6 Hz), 7.71 (d, 2H, J=7.6 Hz), 7.48 (t, 2H, J=7.5 Hz), 7.36 (t, 1H, J=7.3 Hz), 4.25 (s, 3H); $^{13}$C NMR (100 MHz, Acetone-d$_6$) δ HRMS (ESI): Calc'd. for $C_{17}H_{14}N_5O_2^+$ [M+H]$^+$: 320.1142, Observed: 320.1127.

Compound 1-162. Synthesis of N-(4-(tert-butyl)phenyl)-6-methoxy-[1,2,5]oxadiazolo[3,4-b]pyrazin-5-amine (1-162)

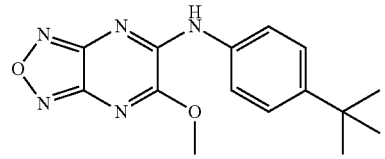 [SMILES: COc1nc2nonc2nc1Nc1ccc(C(C)(C)C)cc1]

Compound 1-162 was synthesized by procedure 1-C using 1-138 to yield 1-162 in 98% as a yellow solid: $^1$H NMR (400 MHz, Acetone-d$_6$) δ 9.49 (brs, 1H), 7.95−7.90 (m, 2H), 7.50−7.45 (m, 2H), 4.21 (s, 3H), 1.33 (m, 9H); $^{13}$C NMR (100 MHz, Acetone-d$_6$) δ 156.57, 152.06, 150.65, 148.91, 147.61, 136.18, 126.53, 122.40, 56.52, 35.14, 31.72. HRMS (ESI): Calc'd. for $C_{15}H_{18}N_5O_2^+$ [M+H]$^+$: 300.1455, Observed: 300.1464.

Compound 1-163. Synthesis of N-(2-fluoro-4-(trifluoromethoxy)phenyl)-6-methoxy-[1,2,5]oxadiazolo[3,4-b]pyrazin-5-amine (1-163)

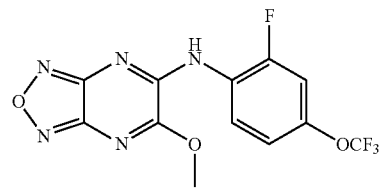

Compound 1-163 was synthesized by procedure 1-C using 1-138 to yield 1-163 in 96% as a yellow solid: $^1$H NMR (400 MHz, Acetone-d$_6$) δ 9.23 (brs, 1H), 8.30 (t, 1H J=8.8 Hz), 7.41 (dd, 1H, J=10.9 Hz), 7.35 (d, 1H, J=9.1 Hz), 4.29 (s, 3H); $^{13}$C NMR (100 MHz, Acetone-d$_6$) δ 156.36, 156.16 (d, J=250 Hz), 151.77, 150.91, 148.36, 147.39 (dq, J=11 Hz), 127.61 (d, J=2 Hz), 125.43 (d, J=12 Hz), 121.41 (q, J=257 Hz), 118.21 (d, J=4 Hz), 110.64 (d, J=24 Hz), 56.86; ¹⁹F NMR (376 MHz, Acetone-d₆) δ −58.97 (s, 3F), −120.20 (t, 1F, J=9.8 Hz); HRMS (ESI): Calc'd. for $C_{12}H_8F_4N_5O_3^+$ [M+H]⁺: 346.0558, Observed: 346.0538.

Compound 1-164. Synthesis of N-(4-isopropylphenyl)-6-methoxy-[1,2,5]oxadiazolo[3,4-b]pyrazin-5-amine (1-164)

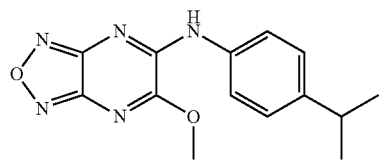 [SMILES: COc1nc2nonc2nc1Nc1ccc(C(C)C)cc1]

Compound 1-164 was synthesized by procedure 1-C using 1-138 to yield 1-164 in 95% as a yellow solid: ¹H NMR (400 MHz, Acetone-d₆) δ 9.48 (brs, 1H), 7.95–7.90 (m, 2H), 7.35–7.30 (m, 2H), 4.22 (s, 3H), 2.94 (h, 1H, J=6.9 Hz), 1.25 (d, 6H, J=6.9 Hz); ¹³C NMR (100 MHz, Acetone-d₆) δ 156.61, 152.09, 150.67, 147.65, 146.77, 136.51, 127.60, 122.78, 56.52, 34.50, 24.40; HRMS (ESI): Calc'd. for $C_{14}H_{16}N_5O_2^+$ [M+H]⁺: 286.1299, Observed: 286.1299.

Compound 1-165. Synthesis of 6-methoxy-N-(4-(trifluoromethyl)phenyl)-[1,2,5]oxadiazolo[3,4-b]pyrazin-5-amine (1-165)

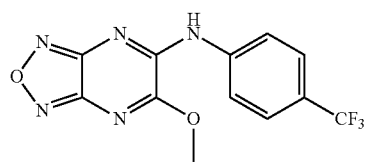 [SMILES: COc1nc2nonc2nc1Nc1ccc(C(F)(F)F)cc1]

Compound 1-165 was synthesized by procedure 1-C using 1-138 to yield 1-165 in 79% as a yellow solid: ¹H NMR (400 MHz, Acetone-d₆) δ 9.82 (brs, 1H), 8.29 (d, 2H, J=8.8 Hz), 7.80 (d, 2H, J=8.8 Hz), 4.24 (s, 3H); ¹⁹F NMR (376 MHz, Acetone-d₆) δ −62.62 (s, 3F); ¹³C NMR (100 MHz, Acetone-d₆) δ HRMS (ESI): Calc'd. for $C_{12}H_9F_3N_5O_2^+$[M+H]⁺: 312.0703, Observed: 312.0710.

Compound 1-166. Synthesis of 6-methoxy-N-(3-(trifluoromethyl)phenyl)-[1,2,5]oxadiazolo[3,4-b]pyrazin-5-amine (1-166)

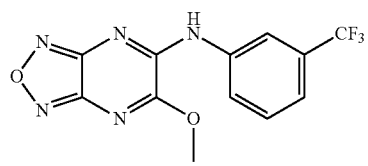 [SMILES: COc1nc2nonc2nc1Nc1cccc(C(F)(F)F)c1]

Compound 1-166 was synthesized by procedure 1-C using 1-138 to yield 1-166 in 79% as a yellow solid: ¹H NMR (400 MHz, Acetone-d₆) δ 9.76 (brs, 1H), 8.43 (brs, 1H), 8.31 (d, 1H, J=8.4 Hz), 7.66 (t, 1H, J=8.1 Hz), 7.53 (d, 1H, J=8.1 Hz), 4.23 (s, 3H); ¹³C NMR (100 MHz, Acetone-d₆) δ 156.24, 151.51, 150.50, 147.69, 139.48, 131.35 (q, J=32 Hz), 130.72, 125.86 (q, J=1 Hz), 125.04 (q, J=272 Hz), 122.10 (q, J=4 Hz), 118.85 (q, J=4 Hz), 56.56; ¹⁹F NMR (376 MHz, Acetone-d₆) δ −63.19 (s, 3F); HRMS (ESI): Calc'd. for $C_{12}H_9F_3N_5O_2^+$[M+H]⁺: 312.0703, Observed: 312.06%.

Compound 1-167. Synthesis of 6-methoxy-N-(4-pentylphenyl)-[1,2,5]oxadiazolo[3,4-b]pyrazin-5-amine (1-167)

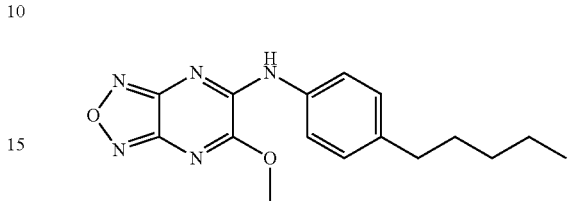

Compound 1-167 was synthesized by procedure 1-C using 1-138 to yield 1-167 in 45% as a yellow solid: ¹H NMR (400 MHz, Acetone-d₆) δ 9.40 (brs, 1H), 7.90 (d, 2H, J=8.6 Hz), 7.24 (d, 2H, J=8.6 Hz), 4.20 (s, 3H), 2.60 (t, 2H, J=7.8 Hz), 1.62 (q, 2H, J=7.7 Hz), 1.40–1.27 (m, 4H), 0.89 (t, 3H, J=6.9 Hz); ¹³C NMR (100 MHz, Acetone-d₆) δ 156.44, 151.97, 150.55, 147.42, 140.71, 136.34, 129.52, 122.51, 56.49, 36.00, 32.25, 32.02, 23.24, 14.40; HRMS (ESI): Calc'd. for $C_{16}H_{20}N_5O_2^+$ [M+H]⁺: 314.1611, Observed: 314.1619.

Compound 1-168. Synthesis of N-(4-(tert-butyl)-2-fluorophenyl)-6-methoxy-[1,2,5]oxadiazolo[3,4-b]pyrazin-5-amine (1-168)

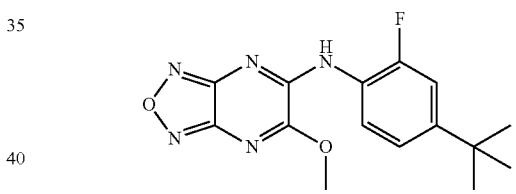

Compound 1-168 was synthesized by procedure 1-C using 1-138 to yield 1-168 in 88% as a yellow solid: ¹H NMR (400 MHz, Acetone-d₆) δ 9.10 (brs, 1H), 8.20 (dd, 1H, J=7.5 Hz), 7.39-7.33 (m, 1H), 7.24–7.17 (m, 1H), 4.29 (s, 3H), 1.35 (s, 9H); ¹³C NMR (100 MHz, Acetone-d₆) δ 156.45, 154.31 (d, J=244 Hz), 151.99, 150.87, 148.58 (d, J=4 Hz), 148.31, 125.03 (d, J=7 Hz), 123.56, 115.89 (d, J=20 Hz), 113.64 (d, J=20 Hz), 56.89, 35.39, 31.83; ¹⁹F NMR (376 MHz, Acetone-d₆) δ −129.41--129.53 (m, 1F); HRMS (ESI): Calc'd. for $C_{15}H_{17}FN_5O_2^+$ [M+H]⁺: 318.1361, Observed: 318.1353.

Compound 1-169. Synthesis of N-(4-iodophenyl)-6-methoxy-[1,2,5]oxadiazolo[3,4-b]pyrazin-5-amine (1-169)

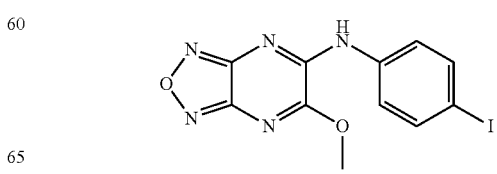

Compound 1-169 was synthesized by procedure 1-C using 1-138 to yield 1-169 in 93% as a yellow solid: ¹H NMR (400 MHz, Acetone-d₆) δ 9.61 (brs, 1H), 7.91–7.87 (m, 2H), 7.82–7.78 (m, 2H), 4.22 (s, 3H); ¹³C NMR (100 MHz, Acetone-d₆) δ 156.53, 151.84, 150.68, 147.72, 138.82, 124.63, 124.53, 89.12, 56.62; HRMS (ESI): Calc'd. for $C_{11}H_9IN_5O_2^+$ [M+H]⁺: 369.9795, Observed: 369.9810.

Compound 1-170. Synthesis of N-(3-iodophenyl)-6-methoxy-[1,2,5]oxadiazolo[3,4-b]pyrazin-5-amine (1-170)

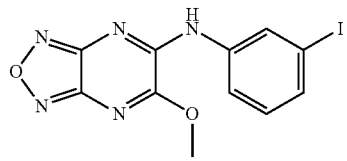 [SMILES: COc1nc2nonc2nc1Nc1cccc(I)c1]

Compound 1-170 was synthesized by procedure 1-C using 1-138 to yield 1-170 in 94% as a yellow solid: ¹H NMR (400 MHz, Acetone-d₆) δ 9.57 (brs, 1H), 8.50 (s, 1H), 8.06 (d, 1H, J=8.3 Hz), 7.59 (d, 1H, J=7.9 Hz), 7.25 (t, 1H, J=8.1 Hz), 4.23 (s, 3H); ¹³C NMR (100 MHz, Acetone-d₆) δ 156.47, 151.78, 150.69, 147.74, 140.18, 134.83, 131.61, 131.08, 121.95, 94.28, 56.65; HRMS (ESI): Calc'd. for $C_{11}H_9IN_5O_2^+$ [M+H]⁺: 369.9795, Observed: 369.9782.

Compound 1-171. Synthesis of N-(2-iodo-4-(trifluoromethoxy)phenyl)-6-methoxy-[1,2,5]oxadiazolo[3,4-b]pyrazin-5-amine (1-171)

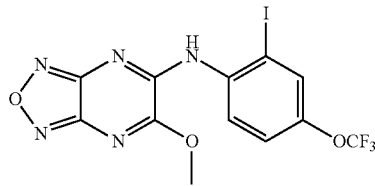 [SMILES: COc1nc2nonc2nc1Nc1ccc(OC(F)(F)F)cc1I]

Compound 1-171 was synthesized by procedure 1-C using 1-138 to yield 1-171 in 67% as a yellow solid: ¹H NMR (400 MHz, Acetone-d₆) δ 9.09 (brs, 1H), 8.39 (d, 1H, J=9.0 Hz), 7.96–7.93 (m, 1H), 7.58–7.53 (m, 1H), 4.33 (s, 3H); ¹³C NMR (100 MHz, Acetone-d₆) δ 156.19, 151.53, 150.66, 148.01, 146.95 (q, J=2 Hz), 138.65, 132.66, 126.22, 122.78, 121.28 (q, J=256 Hz), 94.34, 57.09; ¹⁹F NMR (376 MHz, Acetone-d₆) δ −58.78 (s, 3F); HRMS (ESI): Calc'd. for $C_{12}H_8IF_3N_5O_3^+$ [M+H]⁺: 453.9624, Observed: 453.9636.

Compound 1-172. Synthesis of N-(2-chloro-4-(trifluoromethoxy)phenyl)-6-methoxy-[1,2,5]oxadiazolo[3,4-b]pyrazin-5-amine (1-172)

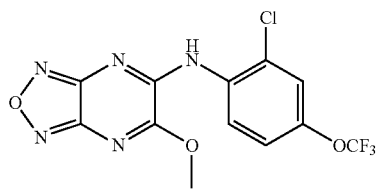

Compound 1-172 was synthesized by procedure 1-C using 1-138 to yield 1-172 in 98% as a yellow solid: ¹H NMR (400 MHz, Acetone-d₆) δ 9.07 (brs, 1H), 8.59 (d, 1H, J=9.1 Hz), 7.61–7.59 (m, 1H), 7.48 (d, 1H, J=9.1 Hz), 4.32 (s, 3H); ¹³C NMR (100 MHz, Acetone-d₆) δ 156.00, 151.33, 150.53, 147.53, 146.60 (q, J=2 Hz), 134.08, 127.66, 125.96, 123.32, 121.49, 121.24 (q, J=256 Hz), 57.10; ¹⁹F NMR (376 MHz, Acetone-d₆) δ −58.87 (s, 3F); HRMS (ESI): Calc'd. for $C_{12}H_8F_3ClN_5O_3^+$ [M+H]⁺: 362.0268, Observed: 362.0265.

Compound 1-173. Synthesis of N-(3-CHLORO-4-(trifluoromethoxy)phenyl)-6-methoxy-[1,2,5]oxadiazolo[3,4-b]pyrazin-5-amine (1-173)

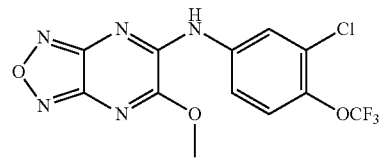 [SMILES: COc1nc2nonc2nc1Nc1ccc(OC(F)(F)F)c(Cl)c1]

Compound 1-173 was synthesized by procedure 1-C using 1-138 to yield 1-173 in 85% as a yellow solid: ¹H NMR (400 MHz, Acetone-d₆) δ 9.68 (brs, 1H), 8.37 (d, 1H, J=2.6 Hz), 8.02 (dd, 1H, J=9.0 Hz). 7.50 (dq, 1H, J=9.0 Hz), 4.20 (s, 3H); ¹³C NMR (100 MHz, Acetone-d₆) δ 155.81, 151.08, 150.18, 147.14, 141.74 (q, J=2 Hz), 138.42, 127.50, 123.84, 123.69, 121.84, 121.21 (q, J=256 Hz), 56.43; ¹⁹F NMR (376 MHz, Acetone-d₆) δ −58.79 (s, 3F); HRMS (ESI): Calc'd. for $C_{12}H_8F_3ClN_5O_3^+$ [M+H]⁺: 362.0268, Observed: 362.0265.

Compound 1-174. Synthesis of N-(3-bromo-4-(trifluoromethoxy)phenyl)-6-methoxy-[1,2,5]oxadiazolo[3,4-b]pyrazin-5-amine (1-174)

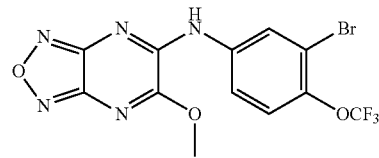

Compound 1-174 was synthesized by procedure 1-C using 1-138 to yield 1-174 in 97% as a yellow solid: ¹H NMR (400 MHz, Acetone-d₆) δ 9.67 (brs, 1H), 8.50 (d, 1H, J=2.6 Hz), 8.08 (dd, 1H, J=9.0 Hz), 7.49 (dq, 1H, J=9.0 Hz), 4.20 (s, 3H); ¹³C NMR (100 MHz, Acetone-d₆) δ 155.85, 151.13, 150.22, 147.17, 143.16 (q, J=2 Hz), 138.51, 126.79, 123.45, 122.56, 121.22 (q, J=257 Hz), 116.21, 56.47; ¹⁹F NMR (376 MHz, Acetone-d₆) δ −58.43 (s, 3F); HRMS (ESI): Calc'd. for $C_{12}H_8F_3BrN_5O_3^+$ [M+H]⁺: 405.9763, Observed: 405.9763.

Compound 1-177. Synthesis of 6-methoxy-N-methyl-N-(4-(trifluoromethyl)phenyl)-[1,2,5]oxadiazolo[3,4-b]pyrazin-5-amine (1-177)

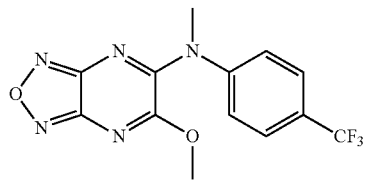 [SMILES: COc1nc2nonc2nc1N(C)c1ccc(C(F)(F)F)cc1]

Compound 1-177 was synthesized by procedure 1-C using 1-138 to yield 1-177 in 72% as a yellow solid: $^1$H NMR (400 MHz, Acetone-d$_6$) δ 7.81 (d, 2H, J=8.3 Hz), 7.62 (d, 2H, J=8.3 Hz), 3.72 (s, 3H), 3.63 (s, 3H); $^{19}$F NMR (376 MHz, Acetone-d$_6$) δ −62.74 (s, 3F); HRMS (ESI): Calc'd. for C$_{13}$H$_{11}$F$_3$N$_5$O$_2$$^+$ [M+H]$^+$: 326.0859, Observed: 326.0845.

Compound 1-178. Synthesis of N-(3-fluoro-4-(trifluoromethyl)phenyl)-6-methoxy-[1,2,5]oxadiazolo[3,4-b]pyrazin-5-amine (1-178)

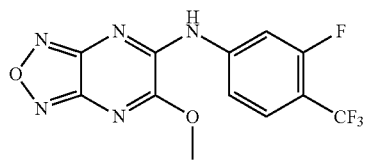 [SMILES: COc1nc2nonc2nc1Nc1ccc(C(F)(F)F)c(F)c1]

Compound 1-178 was synthesized by procedure 1-C using 1-138 to yield 1-178 in 84% as a yellow solid: $^1$H NMR (400 MHz, Acetone-d$_6$) δ 9.91 (s, 1H), 8.36–8.13 (m, 1H), 8.05–7.89 (m, 1H), 7.84–7.70 (m, 1H), 4.23 (s, 3H). $^{19}$F NMR (376 MHz, Acetone-d$_6$) δ −61.28 (d, J=12.3 Hz), −114.52 (td, J=12.7, 8.2 Hz). $^{13}$C NMR (101 MHz, Acetone-d$_6$) δ 160.48 (dq, J=252.0, 2.4 Hz), 156.12, 151.25, 150.48, 147.65, 144.43–144.20 (m), 128.63–128.38 (m), 123.75 (dd, J=269.7, 1.1 Hz), 117.61 (d, J=3.5 Hz), 114.45–113.26 (m), 109.89 (d, J=26.4 Hz), 56.67; HRMS (ESI$^+$): Calc'd. for (C$_{12}$H$_8$F$_4$N$_5$O$_2$+) [M+H]−: 330.0609 Found: 330.0624.

Compound 1-181. Synthesis of 6-butoxy-N-(4-(trifluoromethoxy)phenyl)-[1,2,5]oxadiazolo[3,4-b]pyrazin-5-amine (1-181)

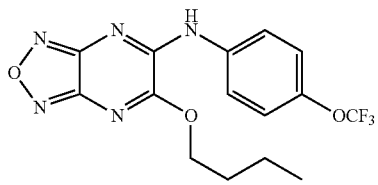 [SMILES: CCCCOc1nc2nonc2nc1Nc1ccc(OC(F)(F)F)cc1]

Compound 1-181 was synthesized by procedure 1-C using 1-179 to yield 1-181 in 63% as an off-white solid: $^1$H NMR (400 MHz, Acetone-d$_6$) δ 9.70–9.52 (m, 1H), 8.19–8.02 (m, 2H), 7.56–7.35 (m, 2H), 4.67 (t, J=6.7 Hz, 2H), 1.97–1.84 (m, 2H), 1.61–1.48 (m, 2H), 0.99 (t, J=7.4 Hz, 3H); $^{19}$F NMR (376 MHz, Acetone-d$_6$) δ −58.78 (s, 3F); $^{13}$C NMR (101 MHz, Acetone-d$_6$) δ 155.93, 151.58, 150.64, 147.80, 146.45 (q, J$_{CF}$=1.9 HZ), 137.63, 124.41, 122.37, 121, 44f (q, J$_{CF}$=255.4 Hz), 70.40, 30.88, 19.68, 14.02; HRMS (ESI$^+$) m/z calc'd. for C$_{15}$H$_{15}$F$_3$N$_5$O$_3$ [M+H]$^+$ 370.1122, found 370.1129.

Compound 1-183. Synthesis of 6-isopropoxy-N-(4-(trifluoromethyl)phenyl)-[1,2,5]oxadiazolo[3,4-b]pyrazin-5-amine (1-183)

Step 1. Synthesis of 5-Chloro-6-isopropoxy-[1,2,5]oxadiazolo[3,4-b]pyrazine (1-183-int))

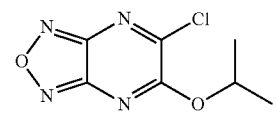

In a 23 ml round bottom flask, 5,6-dichloro-[1,2,5]oxadiazolo[3,4-b]pyrazine (1-2) (0.403 g, 2.11 mmol) and Et$_3$N (0.214 g, 2.11 mmol) were dissolved in 10 mL of anhydrous THF. Isopropanol (0.127 g, 2.11 mmol) was added. The mixture was heated to 43° C. and stirred for 16 h. The mixture was concentrated and purified chromatography on SiO$_2$ to obtain 1-183-int (19%) as a yellow solid: $^1$H NMR (400 MHz, Acetone-d$_6$) δ 5.58 (h, J=6.2 Hz, 1H), 1.53 (d, J=6.2 Hz, 6H); $^{13}$C NMR (100 MHz, Acetone-d$_6$) δ 157.58, 153.76, 152.27, 151.35, 76.09, 21.66.

Step 2. Synthesis of 6-Isopropoxy-N-(4-(trifluoromethyl)phenyl)-[1,2,5]oxadiazolo[3,4-b]pyrazin-5-amine (1-183)

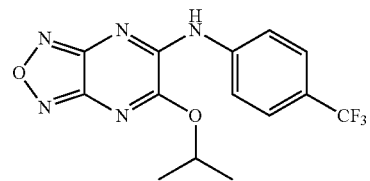 [SMILES: CC(C)Oc1nc2nonc2nc1Nc1ccc(C(F)(F)F)cc1]

In a screw-cap vial, 1-183-int (0.088 g, 0.410 mmol) was dissolved in 3 mL of anhydrous THF, and 4-(trifluoromethyl)aniline (0.145 g, 0.902 mmol) was added. The mixture was heated to reflux and stirred for 16 h. The next day, the mixture was concentrated and purified by chromatography on SiO$_2$ to obtain 1-183 (83%) as a yellow solid: $^1$H NMR (400 MHz, Acetone-d$_6$) δ 9.65 (brs, 1H), 8.21 (d, 2H, J=8.5 Hz), 7.78 (d, 2H, J=8.5 Hz), 5.68 (h, 1H, J=6.2 Hz), 1.52 (d, 6H, J=6.2 Hz); $^{13}$C NMR (100 MHz, Acetone-d$_6$) δ 155.34, 151.48, 150.82, 148.17, 142.30, 126.98 (q, J=3.9 Hz), 126.88 (q, J=32.4 Hz), 125.45 (q, J=272.6 Hz), 122.82, 75.30, 21.76; $^{19}$F NMR (376 MHz, Acetone-d$_6$) δ −62.61 (s, 3F); HRMS (ESI): Calc'd. for C$_{14}$H$_9$F$_6$IN$_5$O$_2$$^+$ [M+H]$^+$: 519.9705, Observed: 519.9714.

Compound 1-184. Synthesis of 6-(2-fluorophenoxy)-N-(4-(trifluoromethyl)phenyl)-[1,2,5]oxadiazolo[3,4-b]pyrazin-5-amine (1-184)

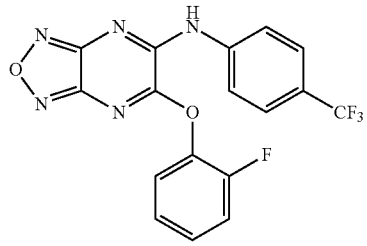 [SMILES: Fc1ccccc1Oc1nc2nonc2nc1Nc1ccc(C(F)(F)F)cc1]

In a screw-cap vial, 1-2 (0.300 g, 1.57 mmol) was dissolved in 8 mL of anhydrous THF at 0° C. In a separate vial, 2-fluorophenol (0.166 g, 1.73 mmol) and sodium tert-butoxide (0.194 g, 1.73 mmol) were mixed in 2 mL of anhydrous THF at 0° C. This mixture was added dropwise to the initial vial while stirring. This was followed by the addition of 4-(trifluoromethyl)aniline (0.506 g, 3.14 mmol). The mixture was refluxed and stirred for 16 h. The next day, the mixture was concentrated and purified chromatography on SiO$_2$ to obtain 1-184 (18%) as a yellow solid: $^1$H NMR (400 MHz, Acetone-d$_6$) δ 10.21 (brs, 1H), 8.38 (d, 2H, J=8.4 Hz), 7.84 (d, 2H, J=8.4 Hz), 7.56 (td, 1H, J=7.8, 1.6 Hz), 7.53–7.36 (m, 3H); $^{19}$F NMR (376 MHz, Acetone-d$_6$) δ −62.57 (s, 3F), −129.41−−129.49 (m, 1F); HRMS (ESI): Calc'd. for $C_{14}H_9F_6IN_5O_2^+$ [M+H]$^+$: 519.9705, Observed: 519.9714.

Compound 1-185. Synthesis of 6-(4-(trifluoromethyl)phenoxy)-N-(4-(trifluoromethyl)phenyl)-[1,2,5]oxadiazolo[3,4-b]pyrazin-5-amine (1-185)

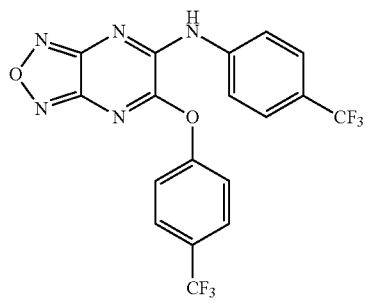 [SMILES: FC(F)(F)c1ccc(Nc2nc3nonc3nc2Oc2ccc(C(F)(F)F)cc2)cc1]

In a screw-cap vial, 1-2 (0.150 g, 0.785 mmol) was dissolved in 3 mL of anhydrous THF at 0° C. In a separate vial, 4-(trifluoromethyl)phenol (0.127 g, 0.785 mmol) and sodium tert-butoxide (0.076 g, 0.785 mmol) were mixed in 2 mL of anhydrous THF at 0° C. This mixture was added dropwise to the initial vial while stirring. This was followed by the addition of 4-(trifluoromethyl)aniline (0.506 g, 3.14 mmol). The mixture was refluxed and stirred for 16 h. The next day, the mixture was concentrated and purified by chromatography on SiO$_2$ to obtain 1-185 (45%) as a yellow solid: $^1$H NMR (400 MHz, Acetone-d$_6$) δ 10.20 (brs, 1H), 8.36 (d, 2H, J=8.4 Hz), 7.97 (d, 2H, J=8.4 Hz), 7.84 (d, 2H, J=8.5 Hz), 7.73 (d, 2H, J=8.5 Hz); $^{19}$F NMR (376 MHz, Acetone-d$_6$) δ −62.62 (s, 3F), −62.72 (s, 3F); HRMS (ESI): Calc'd. for $C_{18}H_{10}F_6N_5O_2^+$ [M+H]$^+$: 442.0733, Observed: 442.0726.

Compound 1-187. Synthesis of N-(2-fluorophenyl)-6-(2,2,2-trifluoroethoxy)-[1,2,5]oxadiazolo[3,4-b]pyrazin-5-amine (1-187)

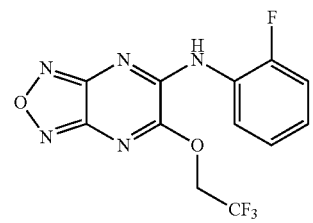 [SMILES: Fc1ccccc1Nc1nc2nonc2nc1OCC(F)(F)F]

A round-bottom flask containing 1-2 (0.21 g, 1.1 mmol) was evacuated and flushed with N$_2$ (3×). Then, under an atmosphere of N$_2$, the solid was cooled in an ice bath and diluted sequentially with dry THF (3 mL), 2-fluoroaniline (0.10 mL, 1.0 mmol), and Et$_3$N (0.15 mL, 1.1 mmol). The resulting red solution, cooled in an ice bath, was stirred for 2.5 h, filtered to remove the salts rinsing with EtOAc, concentrated to remove the solvents, passed through a SiO$_2$ plug (CH$_2$Cl$_2$), and concentrated to a crude yellow/orange solid (0.179 g). The crude solid (0.179 g) in a round-bottom flask was evacuated and refilled with N$_2$ (3×). Then, the solid was diluted sequentially with anhydrous THF (3 mL), 2,2,2-trifluoroethanol (0.13 mL, 2.1 mmol), and Et$_3$N (0.13 mL, 1.1 mmol). The resulting mixture was stirred at rt under an atmosphere of N$_2$ for 17 h, filtered to remove the salts rinsing with EtOAc, and concentrated to a red solid. The solid was purified by chromatography on SiO$_2$ (gradient: 10-13% EtOAc/hexanes) to yield 1-187 (34%) as a light yellow solid: $^1$H NMR ((CD$_3$)$_2$CO, 500 MHz) δ 9.31 (s, 1H), 8.08 (t, J=7.8 Hz, 1H), 7.38–7.30 (m, 3H), 5.32 (q, J=8.5 Hz, 2H); $^{13}$C NMR ((CD$_3$)$_2$CO, 125 MHz) δ 156.5 (d, J$_{CF}$=247 Hz), 154.5, 152.1, 150.2, 147.8, 128.6 (d, J$_{CF}$=8.0 Hz), 126.85, 125.8 (d, J$_{CF}$=11.4 Hz), 125.5 (d, J$_{CF}$=3.8 Hz), 124.1 (q, J$_{CF}$=277 Hz), 116.6 (d, J$_{CF}$=19.6 Hz), 65.12 (q, J$_{CF}$=37.1 Hz). $^{19}$F NMR ((CD$_3$)$_2$CO, 376 MHz) δ−73.7 (t, J=8.5 Hz, 3F), −124.6 to −124.7 (m, 1F); HRMS (ESI$^−$) m/z calc'd. for $C_{12}H_6F_4N_5O_2$ (M−H)$^−$ 328.0463, found 328.0492.

Compound 1-199. Synthesis of 5-methoxy-6-(4-(trifluoromethyl)phenoxy)-[1,2,5]oxadiazolo[3,4-b]pyrazine (1-199)

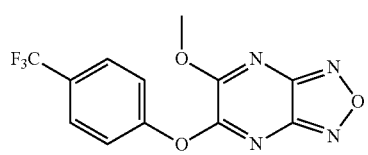 [SMILES: COc1nc2nonc2nc1Oc1ccc(C(F)(F)F)cc1]

In a 6 dram vial, 1-138 (0.295 g, 1.57 mmol) is dissolved in 5 mL dry THF at 0° C. In a separate vial, 4-(trifluoromethyl)phenol (0.140 g, 1.49 mmol) and sodium tert-butoxide (0.143 g, 1.49 mmol) are mixed in 3 mL dry THF at 0° C. This mixture is added dropwise to the initial 6 dram vial while stirring. The final mixture is refluxed and stirred for 0.5 h, followed by concentration and purification via flash chromatography to yield 1-199 (21%) as an off-white solid. ¹H NMR ((CD₃)₂CO, 400 MHz) δ 7.93 (d, 2H, J=8.4 Hz), 7.64 (d, 2H, J=8.4 Hz), 4.29 (s, 3H); ¹³C NMR (100 MHz, Acetone-d₆) δ 157.43, 156.64, 155.53 (q, J=1.5 Hz), 151.70, 150.93, 129.26 (q, J=32.6 Hz), 128.31 (q, J=3.8 Hz), 125.07 (q, J=271.1 Hz), 123.65, 56.92; ¹⁹F NMR (376 MHz, Acetone-d₆) δ −62.76 (s, 3F); HRMS (ESI): Calc'd. for C₁₂H₁₁F₃N₅O₃⁺ [M+NH₄]⁺: 330.0808, Observed: 330.0805.

Compound 1-200. Synthesis of 6-ethoxy-N-(2-fluoro-4-(trifluoromethoxy)phenyl)-[1,2,5]oxadiazolo[3,4-b]pyrazin-5-amine (1-200)

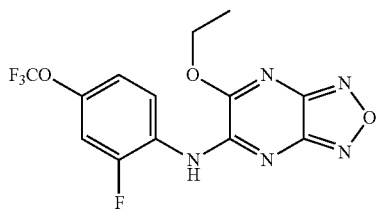 [SMILES: CCOc1nc2nonc2nc1Nc1ccc(OC(F)(F)F)cc1F]

In a 6 dram vial, 1-163 (0.1200 g, 0.348 mmol) was dissolved in 1.70 mL 3:1 ethanol/dioxane. Sodium carbonate (0.1103 g, 1.043 mmol) was added and the mixture was heated to 90° C. and stirred for 16 h. The resulting mixture was concentrated under reduced pressure and purified via flash chromatography (0-13% EtOAc in hexanes) to yield 1-200 in 82% as a yellow solid. ¹H NMR ((CD₃)₂CO, 400 MHz) δ 9.16 (s, 1H), 8.31 (t, 1H, J=8.8 Hz), 7.41–7.36 (m, 1H), 7.35–7.30 (m, 1H), 4.73 (q, 2H, J=1.1 Hz), 1.54 (t, 3H, J=7.1 Hz); ¹³C NMR (100 MHz, Acetone-d₆) δ 155.91 (d, J=250.6 Hz), 155.55, 151.44, 150.74, 148.11, 147.19 (dq, J=10.6, 1.9 Hz), 127.24, 125.29 (d, J=11.3 Hz), 121.27 (q, J=257.0 Hz), 118.04 (d, J=3.8 Hz), 110.42 (dq, J=23.7, 1.2 Hz), 66.84, 14.08; ¹⁹F NMR (376 MHz, Acetone-d₆) δ −58.94 (s, 3F), −120.46--120.55 (m, 1F); HRMS (ESI): Calc'd. for C₁₃H₁₀F₄N₅O₃⁺ [M+H]⁺: 360.0720, Observed: 360.0727.

Compound 1-201. Synthesis of N-(2-fluoro-4-(trifluoromethoxy)phenyl)-6-propoxy-[1,2,5]oxadiazolo[3,4-b]pyrazin-5-amine (1-201)

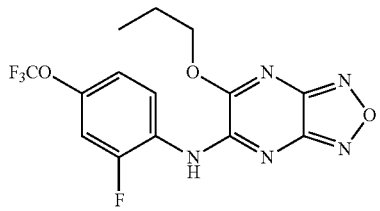 [SMILES: CCCOc1nc2nonc2nc1Nc1ccc(OC(F)(F)F)cc1F]

In a 6 dram vial, 1-163 (0.1000 g, 0.290 mmol) was dissolved in 1.33 mL 3:1 propanol/dioxane. Sodium carbonate (0.0921 g, 0.869 mmol) was added and the mixture was heated to 90° C. and stirred for 16 h. The resulting mixture was concentrated under reduced pressure and purified via flash chromatography (0-15% EtOAc in hexanes) to yield 1-201 in 93% as a yellow solid. ¹H NMR ((CD₃)₂CO, 400 MHz) δ 9.14 (s, 1H), 8.32 (t, 1H, J=8.8 Hz), 7.43–7.37 (m, 1H), 7.37–7.30 (m, 1H), 4.65 (t, 2H, J=6.6 Hz), 1.97 (h, 2H, J=7.4 Hz), 1.11 (t, 3H, J=7.4 Hz); ¹³C NMR (100 MHz, Acetone-d₆) δ 155.76, 151.52, 150.81, 148.19, 147.22 (dq, J=10.7, 2.3 Hz), 127.26 (d, J=1.6 Hz), 125.40 (d, J=11.1 Hz), 121.33 (q, J=256.7 Hz), 118.13 (dd, J=3.9, 1.0 Hz), 110.48 (dd, J=23.7, 1.0 Hz), 72.29, 22.28, 10.64; ¹⁹F NMR (376 MHz, Acetone-d₆) δ −58.98 (s, 3F), −120.8--120.90 (m, 1F); HRMS (ESI): Calc'd. for C₁₄H₁₂F₄N₅O₃⁺ [M+H]⁺: 374.0871, Observed: 374.0870.

Compound 1-202. Synthesis of N-(2-fluoro-4-(trifluoromethyl)phenyl)-6-methoxy-[1,2,5]oxadiazolo[3,4-b]pyrazin-5-amine (1-202)

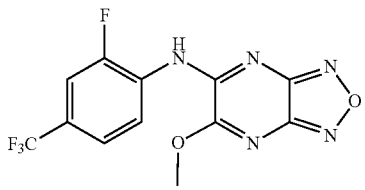 [SMILES: COc1nc2nonc2nc1Nc1ccc(C(F)(F)F)cc1F]

Compound 1-202 was synthesized by procedure 1-C using 1-138 to yield 1-202 in 87% as a yellow solid. ¹H NMR ((CD₃)₂CO, 400 MHz) δ 9.23 (s, 1H), 8.63–8.57 (m, 1H), 7.75–7.67 (m, 2H), 4.31 (s, 3H); ¹⁹F NMR (376 MHz, Acetone-d₆) δ −62.86 (s, 3F), −123.84 (t, 1F, J=9.7 Hz); HRMS (ESI): Calc'd. for C₁₃H₁₂F₄N₅O₃⁺[M+H]⁺:

Compound 1-203. Synthesis of 6-ethoxy-N-(4-(trifluoromethoxy)phenyl)-[1,2,5]oxadiazolo[3,4-b]pyrazin-5-amine (1-203)

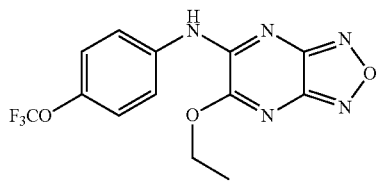 [SMILES: CCOc1nc2nonc2nc1Nc1ccc(OC(F)(F)F)cc1]

In a 6 dram vial, 1-156 (0.1000 g, 0.499 mmol) was dissolved in 1.70 mL 3:1 ethanol/dioxane. Sodium carbonate (0.1600 g, 1.300 mmol) was added and the mixture was heated to 90° C. and stirred for 16 h. The resulting mixture was concentrated under reduced pressure and purified via flash chromatography (0-13% EtOAc in hexanes) to yield 1-203 in 82% as a yellow solid. ¹H NMR (400 MHz, Acetone-d₆) δ 9.65 (s, 1H), 8.16–8.04 (m, 2H), 7.45–7.38 (m, 2H), 4.71 (qd, J=7.0, 1.1 Hz, 2H), 1.51 (qt, J=7.1, 1.0 Hz, 3H). ¹⁹F NMR (376 MHz, Acetone-d₆) δ −58.76 (s 3F). ¹³C NMR (101 MHz, Acetone-d₆) δ 155.80, 151.57, 150.62, 147.77, 146.42 (q, J=2.0 Hz), 137.68, 124.28, 122.37, 121.44 (q, J=255.3 Hz), 66.61, 14.13.

Example 82. Biological Activity of Compounds

Biological activities of the compounds synthesized is determined by determining increase in oxygen consumption rate (OCR).

Oxygen consumption rate (OCR) in whole cells is measured in general accordance with the method of Kenwood B M et al. (Mol. Met. (2014) 3: 114-123).

OCR is measured using a Seahorse XF-24 Flux Analyzer (Seahorse Biosciences, North Billerica, Mass.). NMuLi, C2Cl2, and L6 cells are seeded in a Seahorse 24-well tissue culture plate at a density of $3.5 \times 10^4$ cells/well, isolated cardiomyocytes at a density of $4 \times 10^4$ cells/well, and human primary fibroblasts at a density of $1.1 \times 10^4$ cells/well. The cells are then allowed to adhere for 24 h. Prior to the assay, the media is changed to unbuffered DMEM containing pyruvate and glutamine (Gibco #12800-017, pH=7.4 at 37° C.) and the cells are equilibrated for 30 mins at 37° C. Compounds are injected during the assay and OCR is measured using 2 min measurement periods.

2-3 wells are used per condition and averaged over three plates (n=6-9). Statistical significance is determined by two-way ANOVA with Bonfenoni's posttest.

The activity (increase in OCR) are presented in TABLE 1. Activities are reported as binned $EC_{50}$ values: A=5 µM or less; B=>5 to 20 µM; C=over 20 µM; NA=no effect.

| Compound Number | OCR Activity |
|---|---|
| 2-1 | C |
| 2-2 | B |
| 2-3 | C |
| 2-4 | B |
| 2-5 | B |
| 2-6 | A |
| 2-7 | NA |
| 2-8 | B |
| 2-9 | B |
| 2-10 | NA |
| 2-11 | NA |
| 2-12 | NA |
| 2-13 | B |
| 2-14 | A |
| 2-15 | C |
| 2-16 | B |
| 2-17 | A |
| 2-18 | C |
| 2-19 | B |
| 2-20 | B |
| 2-21 | A |
| 2-22 | B |
| 2-23 | C |
| 2-24 | NA |
| 2-25 | NA |
| 2-26 | B |
| 2-27 | NA |
| 2-28 | NA |
| 2-29 | NA |
| 2-30 | B |
| 2-31 | B |
| 2-32 | B |
| 2-33 | B |
| 2-34 | B |
| 2-35 | C |
| 2-36 | A |
| 2-37 | C |
| 2-38 | B |
| 2-39 | B |
| 2-40 | A |
| 2-41 | B |
| 2-42 | B |
| 2-43 | C |
| 2-44 | C |
| 2-45 | C |
| 2-46 | B |
| 2-47 | A |
| 2-48 | A |
| 2-49 | A |
| 2-50 | NA |
| 2-51 | NA |
| 2-52 | NA |
| 2-53 | NA |
| 2-54 | C |
| 2-55 | C |
| 2-56 | NA |
| 2-57 | NA |
| 2-58 | NA |
| 2-59 | NA |
| 2-60 | C |
| 2-61 | C |
| 2-62 | B |
| 2-63 | C |
| 2-64 | B |
| 2-65 | C |
| 2-66 | A |
| 2-67 | B |
| 2-68 | B |
| 2-69 | A |
| 2-70 | C |
| 2-71 | NA |
| 2-72 | B |
| 2-73 | C |
| 2-74 | A |
| 2-75 | B |
| 4-3 | B |
| 4-5 | B |

Example 83. Diet Induced Obesity Mouse Study

Male C57BL/6J mice aged 3 months were assigned to either normal chow diet (Chow, n=5) or western diet (WD, n=10) for 28 days. After 28 days half of the WD group were switched to WD containing compound 2-21 at a concentration resulting in consumption of ~40 mg/kg/day 1-112 (2-21 40 mpk). Body mass (A), fat mass (measured by EchoMRI (B)), and food intake (C. for the final 14 days) were recorded as indicated. Mice receiving WD containing 2-21 lost body weight and fat mass without a significant change in food intake.

Example 83. ROS Production Assay

Certain compounds of the disclosure also decrease ROS production, which can be measured in this assay. L6 myoblasts are seeded into black-walled clear-bottom 96-well microplates in L6 growth media and grown to confluence. Cells are then washed twice with PBS and co-incubated with 7.5 µM $CM-H_2DCFDA$ and 0.5 ng/µL of each hit compound or vehicle control (DMSO) in KRP buffer (136 mM NaCl, 4.7 mM KCl, 10 mM $NaPO_4$, 0.9 mM $MgSO_4$, 0.9 mM $CaCl_2$, pH 7.4) supplemented with 25 mM D-glucose at 37° C. in 5% $CO_2$/95% air for 1 hr. 100 nM $H_2O_2$ is used as a positive control for ROS production. Following incubation, cells are washed three times with PBS to remove excess probe. Cells are then covered with 100 µL/well PBS and fluorescence intensity is measured by a Tecan Infinite® M200 microplate reader (Tecan Group Ltd., Switzerland) using a top-read configuration and with the excitation and emission Alters set at 495±9 nm and 530±20 nm, respectively. Fluorescence data are recorded on Magellan (version 6.4) software and exported to Microsoft Excel for subsequent analysis. After subtracting the background fluorescence (that emitted from a well which does not receive the $CM-H_2DCFDA$ probe) from each well, ROS production is expressed in terms of percentage fluorescence of the vehicle control for each condition. Compounds which increase ROS levels by greater than 20% are eliminated.

What is claimed is:

1. A compound of Formula I-A or Formula I-B:

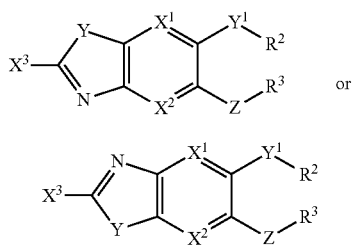

or a pharmaceutically acceptable salt or tautomer thereof, wherein:

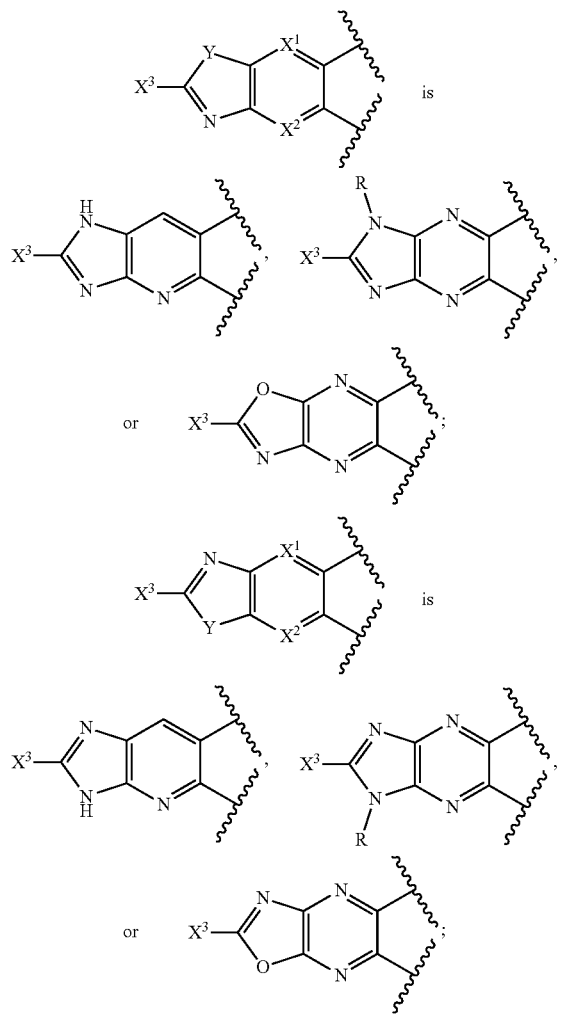

$X^3$ is $C_1$-$C_4$ alkyl, $C_1$-$C_2$ haloalkyl, or phenyl, wherein the phenyl is optionally substituted with one or more independently selected halogen substituents;

$Y^1$ is —$NR^1$— or —O—;

R is H or $CH_3$;

$R^1$ is H, $C_1$-$C_8$ alkyl, $C_2$-$C_8$ alkenyl, or $C_2$-$C_8$ alkynyl;

wherein one or more carbon atoms of the $C_1$-$C_8$ alkyl, $C_2$-$C_8$ alkenyl, or $C_2$-$C_8$ alkynyl is optionally replaced by —C(O)—, —C(O)$NR^{10}$—, —C(O)O—, —$NR^{10}$—, —$NR^{10}$C(O)—, —$NR^{10}$C(O)$NR^{10}$—, —$NR^{10}$S(O)$_n$—, —O—, —OC(O)—, —S(O)$_n$—, or —S(O)$_n NR^{10}$—; and wherein the $C_1$-$C_8$ alkyl, $C_2$-$C_8$ alkenyl, or $C_2$-$C_8$ alkynyl is optionally substituted with one or more independently selected $R^{13}$ substituents;

$R^2$ is $C_1$-$C_8$ alkyl, $C_2$-$C_8$ alkenyl, $C_2$-$C_8$ alkynyl, $C_0$-$C_4$ alkylene-$C_3$-$C_7$ cycloalkyl, $C_0$-$C_4$ alkylene-bridged $C_7$-$C_{12}$ cycloalkyl, $C_0$-$C_4$ alkylene-4- to 7-membered heterocycloalkyl, $C_0$-$C_4$ alkylene-aryl, or $C_0$-$C_4$ alkylene-monocyclic or bicyclic heteroaryl;

wherein one or more carbon atoms of the $C_0$-$C_4$ alkylene, $C_1$-$C_8$ alkyl, $C_2$-$C_8$ alkenyl, or $C_2$-$C_8$ alkynyl is optionally replaced by —C(O)—, —C(O)$NR^{10}$—, —C(O)O—, —$NR^{10}$—, —$NR^{10}$C(O)—, —$NR^{10}$C(O)$NR^{10}$—, —$NR^{10}$S(O)$_n$—, —O—, —OC(O)—, —S(O)$_n$—, or —S(O)$_n NR^{10}$—;

wherein the $C_0$-$C_4$ alkylene, $C_1$-$C_8$ alkyl, $C_2$-$C_8$ alkenyl, or $C_2$-$C_8$ alkynyl is optionally substituted with one or more independently selected $R^{13}$ substituents;

wherein the $C_3$-$C_7$ cycloalkyl, bridged $C_7$-$C_{12}$ cycloalkyl, 4- to 7-membered heterocycloalkyl, aryl, or monocyclic or bicyclic heteroaryl is optionally substituted with one or more independently selected $R^{11}$ substituents; and wherein the $C_3$-$C_7$ cycloalkyl, bridged $C_7$-$C_{12}$ cycloalkyl, 4- to 7-membered heterocycloalkyl, aryl, or monocyclic or bicyclic heteroaryl is optionally substituted with one $R^{12}$ substituent; or $R^1$ and $R^2$, taken together with the nitrogen heteroatom to which they are attached, form a 3- to 7-membered heterocyclyl, wherein one carbon atom of the 3- to 7-membered heterocyclyl is optionally replaced by a heteroatom selected from the group consisting of N, O, and S;

$R^3$ is H, $C_1$-$C_8$ alkyl, $C_2$-$C_8$ alkenyl, $C_2$-$C_8$ alkynyl, $C_0$-$C_4$ alkylene-$C_3$-$C_7$ cycloalkyl, $C_0$-$C_4$ alkylene-aryl, or $C_0$-$C_4$ alkylene-heteroaryl;

wherein one or more carbon atoms of the $C_0$-$C_4$ alkylene, $C_1$-$C_8$ alkyl, $C_2$-$C_8$ alkenyl, or $C_2$-$C_8$ alkynyl is optionally replaced by —C(O)—, —C(O)$NR^{10}$—, —C(O)O—, —$NR^{10}$—, —$NR^{10}$C(O)—, —$NR^{10}$C(O)$NR^{10}$—, —$NR^{10}$S(O)$_n$—, —O—, —OC(O)—, —S(O)$_n$—, or —S(O)$_n NR^{10}$—;

wherein the $C_0$-$C_4$ alkylene, $C_1$-$C_8$ alkyl, $C_2$-$C_8$ alkenyl, or $C_2$-$C_8$ alkynyl is optionally substituted with one or more independently selected $R^{13}$ substituents; and wherein the $C_3$-$C_7$ cycloalkyl, aryl, or heteroaryl is optionally substituted with one or more independently selected $R^{u}$ substituents;

each $R^{10}$ is independently H, $C_1$-$C_6$ alkyl, or $C_0$-$C_2$ alkylene-$C_3$-$C_7$ cycloalkyl;

each $R^{11}$ is independently halogen, CN, $NO_2$, $C_1$-$C_8$ alkyl, $C_2$-$C_8$ alkenyl, $C_2$-$C_8$ alkynyl, C(O)H, C(O)OH, $NH_2$, OH, =O, or halosulfanyl;

wherein one or more carbon atoms of each $C_1$-$C_8$ alkyl, $C_2$-$C_8$ alkenyl, and $C_2$-$C_8$ alkynyl is optionally and independently replaced by —C(O)—, —C(O)$NR^{10}$—, —C(O)O—, —$NR^{10}$—, —$NR^{10}$C(O)—, —O—, —OC(O)—, or —S(O)$_n$—; and wherein each $C_1$-$C_8$ alkyl, $C_2$-$C_8$ alkenyl, or $C_2$-$C_8$ alkynyl is optionally and independently substituted with one or more independently selected $R^{13}$ substituents;

$R^{12}$ is O—$C_0$-$C_4$ alkylene-$C_3$-$C_7$ cycloalkyl, O—$C_0$-$C_4$ alkylene-5- or 6-membered heterocycloalkyl, O—$C_0$-$C_4$ alkylene-aryl, O—$C_0$-$C_4$ alkylene-5- or 6-membered heteroaryl, $C_0$-$C_4$ alkylene-$C_3$-$C_7$ cycloalkyl, $C_0$-$C_4$ alkylene-5- or 6-membered heterocycloalkyl, $C_0$-$C_4$ alkylene-aryl, or $C_0$-$C_4$ alkylene-5- or 6-membered heteroaryl, wherein the $C_3$-$C_7$ cycloalkyl, 5- or 6-membered heterocycloalkyl, aryl, or 5- or 6-membered heteroaryl is optionally substituted with one or more substituents independently selected from the group consisting of halogen, CN, $NO_2$, $C_1$-$C_6$ alkyl, $C_1$-$C_2$ haloalkyl, $C_1$-$C_4$ alkylene-$NHC_1$-$C_6$ alkyl, $C_1$-$C_4$ alkylene-N($C_1$-$C_6$ alkyl)$_2$, $C_2$-$C_6$ alkenyl, $C_2$-$C_6$ alkynyl, C(O)H, C(O)$C_2$-$C_6$ alkyl, C(O)OH, C(O)O$C_1$-$C_6$ alkyl, $NH_2$, $NHC_1$-$C_6$ alkyl, N($C_1$-$C_6$ alkyl)$_2$, OH, O$C_1$-$C_6$ alkyl, O$C_1$-$C_2$ haloalkyl, and =O;

each $R^{13}$ is independently halogen, CN, $NO_2$, C(O)H, C(O)OH, $NH_2$, OH, =O, $C_3$-$C_7$ cycloalkyl, or phenyl;

Z is —O— or —S—; and each n is independently 0, 1, or 2.

2. The compound of claim 1, wherein the compound is of Formula I-A:

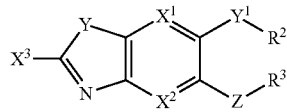

Formula I-A or a pharmaceutically acceptable salt or tautomer thereof, wherein:

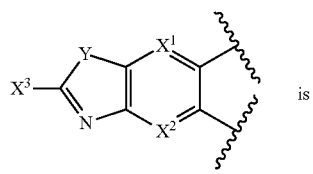 is

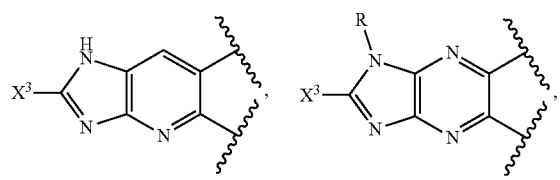

or 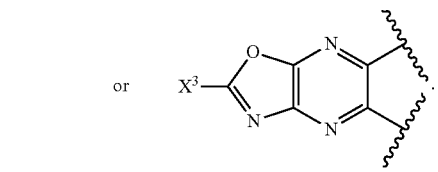

3. The compound of claim 1, wherein the compound is of Formula I-B:

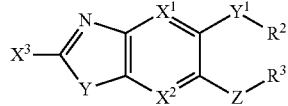

Formula I-B or a pharmaceutically acceptable salt or tautomer thereof, wherein:

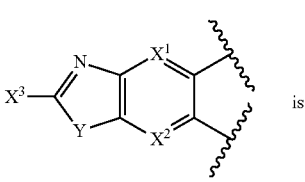 is

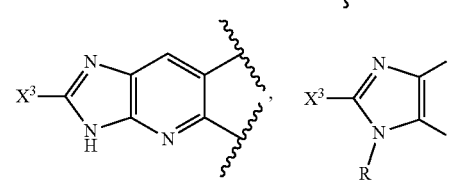

or 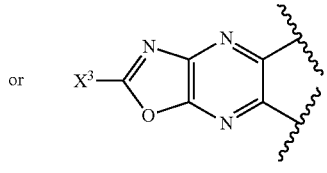

4. The compound of claim 1, or a pharmaceutically acceptable salt thereof, wherein:

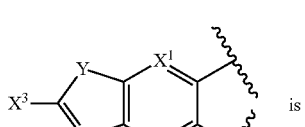 is

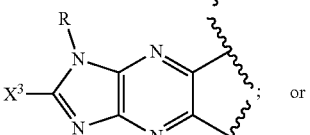;  or

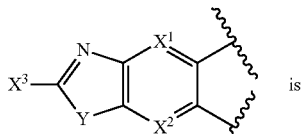 is

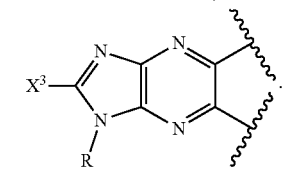.

5. The compound of claim 1, or a pharmaceutically acceptable salt thereof, wherein:

(i)

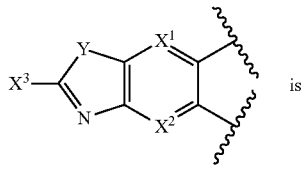

is

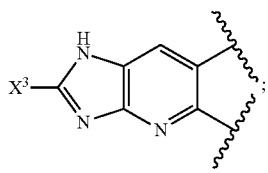

and

Z is —O—; or (ii)

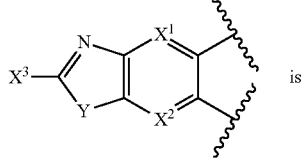

is

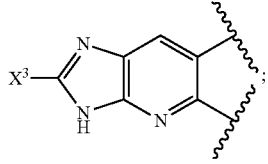

and

Z is —O—.

6. The compound of claim 1, or a pharmaceutically acceptable salt thereof, wherein:

(i)

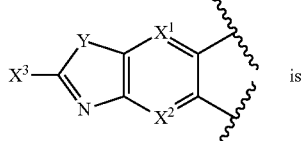

is

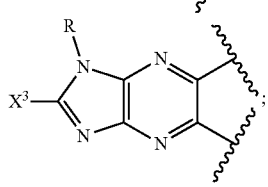

and

Z is —O—; or (ii)

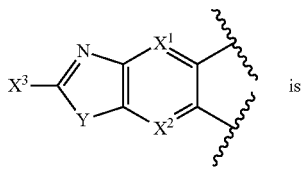

is

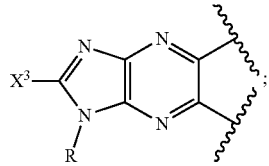

and

Z is —O—.

7. The compound of claim 1, or a pharmaceutically acceptable salt or tautomer thereof, wherein $X^3$ is $CH_3$, $CF_3$, $CF_2CF_3$, or phenyl, wherein the phenyl is optionally substituted with one or more F substituents.

8. The compound of claim 1, or a pharmaceutically acceptable salt or tautomer thereof, wherein:

$Y^1$ is —$NR^1$—; and $R^1$ is H or unsubstituted $C_1$-$C_6$ alkyl.

9. The compound of claim 8, or a pharmaceutically acceptable salt or tautomer thereof, wherein $R^2$ is $C_0$-$C_4$ alkylene-bridged $C_7$-$C_{12}$ cycloalkyl or $C_0$-$C_4$ alkylene-aryl;

wherein one or more carbon atoms of the $C_0$-$C_4$ alkylene is optionally replaced by —C(O)—, —C(O)$NR^{10}$—, —C(O)O—, —$NR^{10}$—, —$NR^{10}$C(O)—, —O—, —OC(O)—, or —S(O)$_n$—;

wherein the $C_0$-$C_4$ alkylene is optionally substituted with one or more independently selected $R^{13}$ substituents;

wherein the bridged $C_7$-$C_{12}$ cycloalkyl or aryl is optionally substituted with one or more independently selected $R^{11}$ substituents; and wherein the bridged $C_7$-$C_{12}$ cycloalkyl or aryl is optionally substituted with one $R^{12}$ substituent; and each n is independently 0, 1, or 2.

10. The compound of claim 1, or a pharmaceutically acceptable salt or tautomer thereof, wherein R is H.

11. The compound of claim 1, or a pharmaceutically acceptable salt or tautomer thereof, wherein $R^2$ is $C_0$-$C_4$ alkylene-$C_3$-$C_7$ cycloalkyl, $C_0$-$C_4$ alkylene-bridged $C_7$-$C_{12}$ cycloalkyl, $C_0$-$C_4$ alkylene-4- to 7-membered heterocycloalkyl, $C_0$-$C_4$ alkylene-aryl, or $C_0$-$C_4$ alkylene-monocyclic or bicyclic heteroaryl;

wherein one or more carbon atoms of the $C_0$-$C_4$ alkylene is optionally replaced by —C(O)—, —C(O)$NR^{10}$—, —C(O)O—, —$NR^{10}$—, —$NR^{10}$C(O)—, —O—, —OC(O)—, or —S(O)$_n$—;

wherein the $C_0$-$C_4$ alkylene is optionally substituted with one or more independently selected $R^{13}$ substituents;

wherein the $C_3$-$C_7$ cycloalkyl, bridged $C_7$-$C_{12}$ cycloalkyl, 4- to 7-membered heterocycloalkyl, aryl, or monocyclic or bicyclic heteroaryl is optionally substituted with one or more independently selected $R^{11}$ substituents; and wherein the $C_3$-$C_7$ cycloalkyl, bridged $C_7$-$C_{12}$ cycloalkyl, 4- to 7-membered heterocycloalkyl, aryl, or monocyclic or bicyclic heteroaryl is optionally substituted with one $R^{12}$ substituent; and each n is independently 0, 1, or 2.

12. The compound of claim 1, or a pharmaceutically acceptable salt or tautomer thereof, wherein:
Y$^1$ is —NR$^1$—; and
R$^1$ is H or CH$_3$;
(i) R$^2$ is phenyl, wherein the phenyl is substituted with one, two, or three substituents independently selected from the group consisting of halogen, C$_1$-C$_6$ alkyl, C$_1$-C$_2$ haloalkyl, OH, OC$_1$-C$_6$ alkyl, and OC$_1$-C$_2$ haloalkyl; or
(ii) R$^2$ is phenyl;
wherein the phenyl is optionally substituted with one or two substituents independently selected from the group consisting of halogen, C$_1$-C$_6$ alkyl, C$_1$-C$_2$ haloalkyl, OH, OC$_1$-C$_6$ alkyl, and OC$_1$-C$_2$ haloalkyl;
wherein the phenyl is substituted with one phenyl substituent; and
wherein the phenyl substituent is optionally substituted with one, two, or three substituents independently selected from the group consisting of halogen, C$_1$-C$_6$ alkyl, C$_1$-C$_2$ haloalkyl, OH, OC$_1$-C$_6$ alkyl, and OC$_1$-C$_2$ haloalkyl; or
(iii) R$^2$ is naphthyl.

13. The compound of claim 1, or a pharmaceutically acceptable salt or tautomer thereof, wherein:
R$^3$ is H, C$_1$-C$_8$ alkyl, C$_2$-C$_8$ alkenyl, or C$_2$-C$_8$ alkynyl;
wherein one or more carbon atoms of the C$_1$-C$_8$ alkyl, C$_2$-C$_8$ alkenyl, or C$_2$-C$_8$ alkynyl is optionally replaced by —C(O)O—, —NR$^{10}$—, —O—, —OC(O)—, or —S(O)$_n$—; and
wherein the C$_1$-C$_8$ alkyl, C$_2$-C$_8$ alkenyl, or C$_2$-C$_8$ alkynyl is optionally substituted with one or more independently selected R$^{13}$ substituents; and
each n is independently 0, 1, or 2.

14. The compound of claim 1, or a pharmaceutically acceptable salt or tautomer thereof, wherein R$^3$ is C$_0$-C$_4$ alkylene-C$_3$-C$_7$ cycloalkyl or C$_0$-C$_4$ alkylene-aryl, wherein the C$_3$-C$_7$ cycloalkyl or aryl is optionally substituted with one or more independently selected R$^{11}$ substituents.

15. The compound of claim 1, or a pharmaceutically acceptable salt thereof, wherein:
(i)

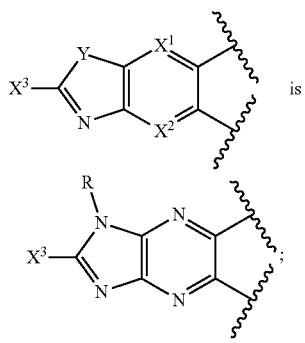

or
(ii)

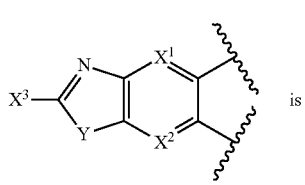

is

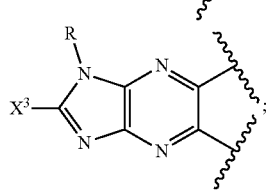

-continued

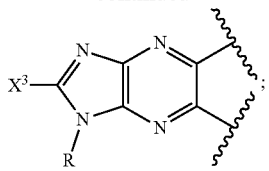

X$^3$ is CH$_3$, CF$_3$, phenyl, or 3-fluorophenyl;
Y$^1$ is —NR$^1$—;
R$^1$ is H, CH$_3$, or CH$_2$CH$_3$;
(iii) R$^2$ is phenyl, wherein the phenyl is substituted with one, two, or three substituents independently selected from the group consisting of halogen, C$_1$-C$_6$ alkyl, C$_1$-C$_2$ haloalkyl, OH, OC$_1$-C$_6$ alkyl, and OC$_1$-C$_2$ haloalkyl; or
(iv) R$^2$ is phenyl;
wherein the phenyl is optionally substituted with one or two substituents independently selected from the group consisting of halogen, C$_1$-C$_6$ alkyl, C$_1$-C$_2$ haloalkyl, OH, OC$_1$-C$_6$ alkyl, and OC$_1$-C$_2$ haloalkyl; and
wherein the phenyl is substituted with one phenyl substituent; and
wherein the phenyl substituent is optionally substituted with one, two, or three substituents independently selected from the group consisting of halogen, C$_1$-C$_6$ alkyl, C$_1$-C$_2$ haloalkyl, OH, OC$_1$-C$_6$ alkyl, and OC$_1$-C$_2$ haloalkyl; or
(iv) R$^2$ is naphthyl;
R$^3$ is H or C$_1$-C$_6$ alkyl, wherein the C$_1$-C$_6$ alkyl is optionally substituted with one or more OH substituents; and
Z is —O—.

16. The compound of claim 1, wherein the compound is selected form the group consisting of:
6-methoxy-N-(4-(trifluoromethoxy)phenyl)-2-(trifluoromethyl)-1H-imidazo[4,5-b]pyrazin-5-amine;
6-methoxy-N-(4-(n-butyl)phenyl)-2-(trifluoromethyl)-1H-imidazo[4,5-b]pyrazin-5-amine;
6-methoxy-N-(2-fluoro-5-(trifluoromethyl)phenyl)-2-(trifluoromethyl)-1H-imidazo[4,5-b]pyrazin-5-amine;
6-methoxy-N-(3-(trifluoromethoxy)phenyl)-2-(trifluoromethyl)-1H-imidazo[4,5-b]pyrazin-5-amine;
6-methoxy-N-(2-methyl-5-(trifluoromethyl)phenyl)-2-(trifluoromethyl)-1H-imidazo[4,5-b]pyrazin-5-amine;
6-methoxy-N-(2-fluoro-3-(trifluoromethyl)phenyl)-2-(trifluoromethyl)-1H-imidazo[4,5-b]pyrazin-5-amine;
6-methoxy-N-(3-fluorophenyl)-2-(trifluoromethyl)-1H-imidazo[4,5-b]pyrazin-5-amine;
6-methoxy-(3,5-bis(trifluoromethyl)phenyl)-2-(trifluoromethyl)-1H-imidazo[4,5-b]pyrazin-5-amine;
6-methoxy-(2-fluorophenyl)-2-(trifluoromethyl)-1H-imidazo[4,5-b]pyrazin-5-amine
6-methoxy-N-(p-tolyl)-2-(trifluoromethyl)-1H-imidazo[4,5-b]pyrazin-5-amine;
6-methoxy-N-phenyl-2-(trifluoromethyl)-1H-imidazo[4,5-b]pyrazin-5-amine;
N-(4-methoxyphenyl)-2-(trifluoromethyl)-1H-imidazo[4,5-b]pyrazin-5-amine;
6-methoxy-N-(3-fluoro-4-(trifluoromethoxy)phenyl)-2-(trifluoromethyl)-1H-imidazo[4,5-b]pyrazin-5-amine;
6-methoxy-N-(2-fluoro-4-(trifluoromethyl)phenyl)-2-(trifluoromethyl)-1H-imidazo[4,5-b]pyrazin-5-amine;
6-methoxy-N-(3,5-difluorophenyl)-2-(trifluoromethyl)-1H-imidazo[4,5-b]pyrazin amine;
6-methoxy-N-(2,3-difluorophenyl)-2-(trifluoromethyl)-1H-imidazo[4,5-b]pyrazin amine;

6-methoxy-N-(2-fluorophenyl)-2-(trifluoromethyl)-1H-imidazo[4,5-b]pyrazin-5-amine;
N-([1,1'-biphenyl]-4-yl)-6-methoxy-2-(trifluoromethyl)-1H-imidazo[4,5-b]pyrazin-5-amine;
6-methoxy-N-(4-(tert-butyl)phenyl)-2-(trifluoromethyl)-1H-imidazo[4,5-b]pyrazin-5-amine;
6-methoxy-N-(naphthalen-2-yl)-2-(trifluoromethyl)-1H-imidazo[4,5-b]pyrazin-5-amine;
6-methoxy-N-(2-fluoro-4-(trifluoromethoxy)phenyl)-2-(trifluoromethyl)-1H-imidazo[4,5-b]pyrazin-5-amine;
6-methoxy-N-(4-(trifluoromethyl)phenyl)-2-(trifluoromethyl)-1H-imidazo[4,5-b]pyrazin-5-amine;
6-methoxy-N-(3-fluoro-4-(trifluoromethyl)phenyl)-2-(trifluoromethyl)-1H-imidazo[4,5-b]pyrazin-5-amine;
6-methoxy-N-(4-ethylphenyl)-2-(trifluoromethyl)-1H-imidazo[4,5-b]pyrazin-5-amine;
6-methoxy-N-(4-isopropylphenyl)-2-(trifluoromethyl)-1H-imidazo[4,5-b]pyrazin-5-amine;
6-methoxy-N-(4-chlorophenyl)-2-(trifluoromethyl)-1H-imidazo[4,5-b]pyrazin-5-amine
6-methoxy-N-(2-fluoro-4-pentylphenyl)-2-(trifluoromethyl)-1H-imidazo[4,5-b]pyrazin-5-amine;
6-methoxy-N-(3-fluoro-4-pentylphenyl)-2-(trifluoromethyl)-1H-imidazo[4,5-b]pyrazin-5-amine;
6-methoxy-N-(4-pentylphenyl)-2-(trifluoromethyl)-1H-imidazo[4,5-b]pyrazin-5-amine; ~
6-methoxy-N-(4-iodophenyl)-2-(trifluoromethyl)-1H-imidazo[4,5-b]pyrazin-5-amine; 2-30
6-methoxy-N-(3-iodophenyl)-2-(trifluoromethyl)-1H-imidazo[4,5-b]pyrazin-5-amine;
6-methoxy-N-(3-(trifluoromethyl)phenyl)-2-(trifluoromethyl)-1H-imidazo[4,5-b]pyrazin-5-amine;
6-methoxy-N-(2-fluoro-4-(tert-butyl)phenyl)-2-(trifluoromethyl)-1H-imidazo[4,5-b]pyrazin-5-amine;
6-methoxy-2-(perfluoroethyl)-N-(4-(trifluoromethoxy)phenyl)-1H-imidazo[4,5-b]pyrazin-5-amine;
6-butoxy-N-(4-(trifluoromethoxy)phenyl)-2-(trifluoromethyl)-1H-imidazo[4,5-b]pyrazin-5-amine;
6-(2,2,2-trifluoroethoxy)-N-(4-(trifluoromethoxy)phenyl)-2-(trifluoromethyl)-1H-imidazo[4,5-b]pyrazin-5-amine;
6-ethoxy-N-(4-(trifluoromethoxy)phenyl)-2-(trifluoromethyl)-1H-imidazo[4,5-b]pyrazin-5-amine; 2-37
6-ethoxy-N-(2-fluoro-4-(trifluoromethoxy)phenyl)-2-(trifluoromethyl)-1H-imidazo[4,5-b]pyrazin-5-amine;
6-propoxy-N-(2-fluoro-4-(trifluoromethoxy)phenyl)-2-(trifluoromethyl)-1H-imidazo[4,5-b]pyrazin-5-amine;
6-methoxy-2-(trifluoromethyl)-5-(4-(trifluoromethyl)phenoxy)-1H-imidazo[4,5-b]pyrazine; 2-40
N-(2-iodo-4-(trifluoromethoxy)phenyl)-6-methoxy-2-(trifluoromethyl)-1H-imidazo[4,5-b]pyrazin-5-amine;
N-(2-chloro-4-(trifluoromethoxy)phenyl)-6-methoxy-2-(trifluoromethyl)-1H-imidazo[4,5-b]pyrazin-5-amine;
N-(3-chloro-4-(trifluoromethoxy)phenyl)-6-methoxy-2-(trifluoromethyl)-1H-imidazo[4,5-b]pyrazin-5-amine;
N-(3-bromo-4-(trifluoromethoxy)phenyl)-6-methoxy-2-(trifluoromethyl)-1H-imidazo[4,5-b]pyrazin-5-amine;
5-isopropoxy-2-(trifluoromethyl)-N-(4-(trifluoromethyl)phenyl)-1H-imidazo[4,5-b]pyrazin-6-amine;
5-(2-fluorophenoxy)-2-(trifluoromethyl)-N-(4-(trifluoromethyl)phenyl)-1H-imidazo[4,5-b]pyrazin-6-amine;
2-(trifluoromethyl)-5-(4-(trifluoromethyl)phenoxy)-N-(4-(trifluoromethyl)phenyl)-1H-imidazo[4,5-b]pyrazin-6-amine;
2-(trifluoromethyl)-5,6-bis(4-(trifluoromethyl)phenoxy)-1H-imidazo[4,5-b]pyrazine;
5-methoxy-N-methyl-2-(trifluoromethyl)-N-(4-(trifluoromethyl)phenyl)-1H-imidazo[4,5-b]pyrazin-6-amine;
5-methoxy-2-methyl-N-(4-(trifluoromethyl)phenyl)-1H-imidazo[4,5-b]pyrazin-6-amine;
5-((4-(trifluoromethoxy)phenyl)amino)-2-(trifluoromethyl)-1H-imidazo[4,5-b]pyrazin-6-ol;
5-((2-fluoro-4-(trifluoromethoxy)phenyl)amino)-2-(trifluoromethyl)-1H-imidazo[4,5-b]pyrazin-6-ol;
of 5-((2-fluoro-3-(trifluoromethyl)phenyl)amino)-2-(trifluoromethyl)-1H-imidazo[4,5-b]pyrazin-6-ol;
5-((4-(trifluoromethyl)phenyl)amino)-2-(trifluoromethyl)-1H-imidazo[4,5-b]pyrazin-6-ol; 2-55
5-((4-(tert-butyl)phenyl)amino)-2-(trifluoromethyl)-1H-imidazo[4,5-b]pyrazin-6-ol;
6-methoxy-1-methyl-2-(trifluoromethyl)-N-(4-(trifluoromethyl)phenyl)-1H-imidazo[4,5-b]pyrazin-5-amine;
5-methoxy-1-methyl-2-(trifluoromethyl)-N-(4-(trifluoromethyl)phenyl)-1H-imidazo[4,5-b]pyrazin-6-amine;
1-methyl-2-(trifluoromethyl)-6-((4-(trifluoromethyl)phenyl)amino)-1H-imidazo[4,5-b]pyrazin-5-ol;
6-methoxy-2-phenyl-N-(4-(trifluoromethoxy)phenyl)-1H-imidazo[4,5-b]pyrazin-5-amine;
2-(3-fluorophenyl)-6-((2-fluorophenyl)amino)oxazolo[4,5-b]pyrazin-5-ol; and
6-((3,5-bis(trifluoromethyl)phenyl)amino)-2-(3-fluorophenyl)oxazolo[4,5-b]pyrazin-5-ol,
or a pharmaceutically acceptable salt thereof.

17. A pharmaceutical composition comprising a pharmaceutically acceptable carrier together with a compound of claim 1, or a pharmaceutically acceptable salt or tautomer thereof.

18. A method for regulating glucose homeostasis in a patient, wherein the method comprises administering to the patient in need thereof a therapeutically effective amount of a compound of claim 1, or a pharmaceutically acceptable salt or tautomer thereof.

19. A method for regulating insulin action in a patient, wherein the method comprises administering to the patient in need thereof a therapeutically effective amount of a compound of claim 1, or a pharmaceutically acceptable salt or tautomer thereof.

20. A method for decreasing the risk of cancer in a patient at risk for cancer, wherein the method comprises administering to the patient in need thereof a therapeutically effective amount of a compound of claim 1, or a pharmaceutically acceptable salt or tautomer thereof.

21. A method for decreasing the risk of developing a condition responsive to mitochondrial uncoupling in a patient, wherein the method comprises administering to the patient in need thereof a therapeutically effective amount of a compound of claim 1, or a pharmaceutically acceptable salt or tautomer thereof;
wherein the condition responsive to mitochondrial uncoupling is selected from the group consisting of Alzheimer's dementia, cancer, fatty liver disease, heart failure, Huntington's disease, insulin resistance, ischemia reperfusion injury, multiple sclerosis, non-alcoholic fatty liver disease (NALFD), non-alcoholic steatohepatitis (NASH), obesity, Parkinson's disease, and type II diabetes.

22. The method of claim 21, wherein the condition responsive to mitochondrial uncoupling is cancer.

23. The method of claim 22, wherein the cancer is selected from the group consisting of an adrenocortical carcinoma, melanoma, primary colon cancer, a cancer having cancerous cells with a beta-catenin mutation, a cancer having cancerous cells with impaired p53 activity, a cancer having cancerous cells with impaired p53 expression, a cancer having cancerous cells with a Ras mutation, and a cancer with metastasis to the liver.

24. A method for treating a condition responsive to mitochondrial uncoupling in a patient, wherein the method comprises administering to the patient in need thereof a therapeutically effective amount of a compound of claim 1, or a pharmaceutically acceptable salt or tautomer thereof;

wherein the condition responsive to mitochondrial uncoupling is selected from the group consisting of Alzheimer's dementia, cancer, fatty liver disease, heart failure, Huntington's disease, insulin resistance, ischemia reperfusion injury, multiple sclerosis, non-alcoholic fatty liver disease (NALFD), non-alcoholic steatohepatitis (NASH), obesity, Parkinson's disease, and type II diabetes.

25. The method of claim 24, wherein the condition responsive to mitochondrial uncoupling is cancer.

26. The method of claim 25, wherein the cancer is selected from the group consisting of an adrenocortical carcinoma, melanoma, primary colon cancer, a cancer having cancerous cells with a beta-catenin mutation, a cancer having cancerous cells with impaired p53 activity, a cancer having cancerous cells with impaired p53 expression, a cancer having cancerous cells with a Ras mutation, and a cancer with metastasis to the liver.

\* \* \* \* \*